(12) United States Patent
Blair et al.

(10) Patent No.: US 12,733,925 B2
(45) Date of Patent: Sep. 15, 2026

(54) LOW PROFILE STAPLE AND METHODS FOR USING THE SAME

(71) Applicant: MedShape, Inc., Atlanta, GA (US)

(72) Inventors: Jeremy Webster Blair, Atlanta, GA (US); Courtney Lynne Kline, Sandy Springs, GA (US)

(73) Assignee: MedShape, Inc., Atlanta, GA (US)

( * ) Notice: Subject to any disclaimer, the term of this patent is extended or adjusted under 35 U.S.C. 154(b) by 208 days.

(21) Appl. No.: 18/477,526

(22) Filed: Sep. 28, 2023

(65) Prior Publication Data

US 2024/0099715 A1 Mar. 28, 2024

Related U.S. Application Data

(60) Provisional application No. 63/377,483, filed on Sep. 28, 2022.

(51) Int. Cl.

| | |
|---|---|
| ***A61B 17/064*** | (2006.01) |
| ***A61B 17/88*** | (2006.01) |
| *A61B 17/00* | (2006.01) |
| *A61B 17/56* | (2006.01) |
| *A61B 17/68* | (2006.01) |

(52) U.S. Cl.

CPC .......... *A61B 17/0642* (2013.01); *A61B 17/88* (2013.01); *A61B 2017/00867* (2013.01); *A61B 2017/0641* (2013.01); *A61B 2017/0645* (2013.01); *A61B 2017/564* (2013.01); *A61B 2017/681* (2013.01)

(58) Field of Classification Search

CPC ........ A61B 2017/0641; A61B 17/0642; A61B 2017/0645; A61B 2017/564; A61B 17/88

See application file for complete search history.

(56) References Cited

U.S. PATENT DOCUMENTS

| | | | | |
|---|---|---|---|---|
| 10,117,647 B2 * | 11/2018 | Cheney | ................ | A61B 17/064 |
| 10,307,156 B1 * | 6/2019 | Blair | .................. | A61B 17/0642 |
| 11,311,289 B1 * | 4/2022 | Ritz | .................. | A61B 17/1615 |
| 2019/0029674 A1 | 1/2019 | Cheney | | |
| 2019/0192140 A1 | 6/2019 | Ducharme et al. | | |
| 2020/0197005 A1 | 6/2020 | Daniel | | |
| 2023/0255623 A1 | 8/2023 | Ritz et al. | | |

* cited by examiner

*Primary Examiner* — Larry E Waggle, Jr.

(74) *Attorney, Agent, or Firm* — Eversheds Sutherland (US) LLP

(57) ABSTRACT

A staple can include a bridge and two pairs of opposed legs that connect to the bridge. A first pair of legs can connect to the bridge toward a first end at a first shoulder and a second shoulder. A second pair of legs, opposed to the first pair legs, can connect to the bridge toward a second end at a third shoulder. The bridge can include a substantially smooth and non-breaking top surface that transitions downwardly at the first end and the second end to outer surfaces of the first pair of legs and the second pair of legs. The bridge can include a substantially constant moment of inertia, which may help improve performance and reduce risk of staple breakage.

20 Claims, 117 Drawing Sheets

LOW PROFILE STAPLE AND METHODS FOR USING THE SAME

CROSS-REFERENCE TO RELATED APPLICATIONS

This application claims the benefit of and priority to, and incorporates herein by reference in its entirety, U.S. Provisional Patent Application No. 63/377,483, filed Sep. 28, 2022, and entitled LOW PROFILE STAPLE AND METHODS FOR USING THE SAME.

TECHNICAL FIELD

The present systems and processes relate generally to compression-fixation systems.

BACKGROUND

Generally, surgical staples are used in some orthopedic indications for holding two bone segments together. Typically, segments of the same bone are separated (e.g., broken, fractured, etc.) and legs of a staple are inserted into each bone segment to compress ends of two (or more) segments of a broken bone together to promote healing of the bone (e.g., such that the bone segments heal back together).

As will be understood, staples can compress bone segments together based on stored strain profiles of the staples. At minimum, such compression can limit the distance between broken bone segments, thereby possibly helping reduce bone healing time by eliminating gaps that need to be filled by the bones/body when healing. Further, such compression may help increase/speed bone growth.

As will also be understood, space within a body is limited and lower profile staples are desirable. However, in creating a low-profile staple (e.g., a staple that has minimum rise above the surface of a bone when the staple is fully inserted), the amount of stored strain (e.g., amount of compression the staple can impart when inserted) may be limited due to certain design constraints. Further, such low-profile staples may include localized strain concentrations (at corners and the like), which may increase risk of fatigue failure or breakage.

Therefore, there exists a need for a low profile surgical staple that has the capacity for high sustained compression and that minimizes localized strain concentrations.

BRIEF SUMMARY OF THE DISCLOSURE

Briefly described, and according to one embodiment, aspects of the present disclosure generally relate to low profile staples that demonstrate constant or substantially constant moment of inertia between a deformed state and a non-deformed state. In various embodiments, the present staples demonstrate high sustained compression and improved fatigue performance (e.g., minimized localized strain concentrations).

In one or more embodiments, a staple includes a bridge and two or more legs that connect to the bridge. For example, the staple may include four legs and each of the four legs connect to the bridge at a transition area, such as a shoulder. In some embodiments, the transition areas transition a top surface of the bridge downwardly to an outer surface of at least one leg. In the same example, the bridge includes a substantially smooth, non-breaking top surface and each shoulder transitions the bridge top surface to an outer surface of the corresponding leg. In at least one embodiment, a substantially smooth surface refers to a surface in which a height deviation at any point along the surface is within two standard deviations of an average height deviation of the total surface. In one or more embodiments, the bridge demonstrates a substantially equal moment of inertia along a length of the bridge. In at least one embodiment, the substantially equal moment of inertia contributes to equal distribution of strain across the bridge, thereby reducing the prevalence of stress concentrations throughout and promoting staple durability. In various embodiments, the shoulders connecting the bridge and legs demonstrate substantially curved and/or arcuate transitions that push stress concentrations away from the points of bridge and staple connection and into the bridge.

According to particular embodiments, bridges of a staple discussed herein demonstrate a substantially constant moment of inertia. In various embodiments, the constant moment of inertia is relative to the x-axis (horizontal axis) along a length of the bridge. In at least one embodiment, the moment of inertia represents the resistance to bending of the bridge in the manner it would be deformed (e.g., from a relaxed state to a deformed state). As one example, three cross-sections are taken: 1) at a right plane through the tangent point between the bridge arc and the radial point of the right shoulder (for the staple shown in FIGS. 9 and 27, the tangent point between the bridge arc and the radial point of the first inline leg or second inline leg may be used); 2) at a left plane through the tangent point between the bridge arc and the radial point of the left shoulder; and 3) through a midpoint of the bridge (e.g., center plane), each cross-section resulting in a relatively constant moment of inertia. This translation of stress and strain away from leg connections and into the bridge and relatively constant resistance to bending further reduces stress concentration prevalence and increases the torsional stability of the staple.

As will be understood, a relatively constant moment of inertia may mean moment of inertia measurements at a right plane, left plane, and/or center plane are within about 0-20%. As will further be understood, a portion of a bridge (e.g., left side or right side) may have a constant moment of inertia. For example, a staple may include a relatively constant moment of inertia between a right plane (or left plane) and a center plane of a bridge, but have an inconstant moment of inertia between the opposite plane and the center plane.

In various embodiments, the staple includes four legs, a bridge, and four shoulders that each connect one of the four legs to the bridge. In one or more embodiments, the bridge includes a substantially rectangular shape and each shoulder connects one of the four legs to a corner of the substantially rectangular shape. In at least one embodiment, the four legs include two pairs of opposing legs. According to one embodiment, an angle between the two pairs of opposing legs measures about 24 degrees. In one or more embodiments, the bridge is curved between a first end at which a pair of the four legs connect to the bridge and a second end, opposite the first end, at which a second pair of the four legs connect. In various embodiments, the bridge curvature defines the angle between the two pairs of opposing legs and measures about 24 degrees. In one or more embodiments, the staple can deform from a first state such that the angle between the two pairs of opposing legs increases. In at least one embodiment, the staple deforms substantially along a length of the bridge (e.g., as opposed to deforming at the shoulders that connect the legs to the bridge). In various embodiments, the staple is biased to return to the first state such that, following initial deformation, the staple undergoes a reverse deformation toward the first state.

In at least one embodiment, the staple provides compression by undergoing reverse deformation toward the first state while inserted to a target site. In one example, the staple, in a deformed state, is inserted to a target site such that a pair of legs lie in a first bony fragment and a second, opposed pair of legs lie in a second bony fragment. In the same example, as the staple undergoes reverse deformation toward the first state, the pair of legs and the opposed pair of legs compress the first and second bony fragments, thereby promoting fixation and fusion of the same. As used herein, a bony fragment may include different bones (e.g., compressing/fusing different bones of the foot) or portions of the same bone (e.g., compressing broken/separated fragments of the same bone).

The present disclosure relates to a staple, according to a first aspect, comprising a bridge between radial tangents of two opposing legs, the bridge comprising: a non-breaking top surface between a first edge and a second edge; an apex of the top surface; a first curved surface between the apex and the first edge; a second curved surface between the apex and the second edge; a first transition area transitioning the top surface of the bridge downwardly to an outer surface of each of two legs proximate a first side of the bridge; a second transition area transitioning the top surface of the bridge downwardly to an outer surface of at least one leg proximate the second side of the bridge, wherein: the staple is deformable from a relaxed position to a deformed position; and strain in the bridge is greater than or equal to strain in each of the two legs or the at least one leg, thereby reducing a risk of breakage of the staple According to a second aspect, the staple of the first aspect or any other aspect, wherein strain in a central region of the bridge is greater than strain in other portions of the bridge.

According to a third aspect, the staple of the second aspect or any other aspect, wherein the strain at the apex of the bridge is greater than strain in the first transition area or second transition area.

According to a fourth aspect, the staple of the third aspect or any other aspect, wherein each of the two legs and the at least one leg are connected to the bridge via a radial transition.

According to a fifth aspect, the staple of the fourth aspect or any other aspect, wherein the bridge comprises: a midpoint; a first thickness at the midpoint; a second thickness at the radial transition to the at least one leg.

According to a sixth aspect, the staple of the fifth aspect or any other aspect, wherein the second thickness is greater than the first thickness.

According to a seventh aspect, the staple of the sixth aspect or any other aspect, wherein a thickness of the bridge decreases linearly from the second thickness to the first thickness.

According to an eighth aspect, the staple of the fourth aspect or any other aspect, wherein each of the two legs, at least one leg, and bridge are integrally formed and manufactured from a single piece of metal.

According to a ninth aspect, the staple of the eighth aspect or any other aspect, wherein the staple comprises nitinol.

According to a tenth aspect, the staple of the nineth aspect or any other aspect, wherein the first curved surface and the second curved surface form a constantly curved surface between the first edge and the second edge.

According to an eleventh aspect, the staple of the nineth aspect or any other aspect, wherein the apex comprises a flat portion between the first curved surface and the second curved surface.

The present disclosure also relates to a method of using a staple. According to a twelfth aspect, the present disclosure relates to a method comprising the steps of inserting a staple into one or more bony fragments of a patient in a deformed position, the staple comprising: a bridge between radial tangents of two opposing legs, the bridge comprising: a non-breaking top surface between a first edge and a second edge; an apex of the top surface; a first curved surface between the apex and the first edge; a second curved surface between the apex and the second edge; a first transition area transitioning the top surface of the bridge downwardly to an outer surface of each of two legs proximate a first side of the bridge; a second transition area transitioning the top surface of the bridge downwardly to an outer surface of the at least one leg proximate the second side of the bridge, wherein: causing the staple to attempt to move from the deformed position to a relaxed position such that the staple compresses the one or more bony fragments of the patient and strain in the bridge is greater than or equal to strain in each of the two legs or the at least one leg, thereby reducing a risk of breakage of the staple.

According to a thirteenth aspect, the method of the twelfth aspect or any other aspect, wherein strain in a central region of the bridge is greater than strain in other portions of the bridge.

According to a fourteenth aspect, the method of the thirteenth aspect or any other aspect, wherein the strain at the apex of the bridge is greater than strain in the first transition area or second transition area.

According to a fifteenth aspect, the method of the fourteenth aspect or any other aspect, wherein each of the two legs and the at least one leg are connected to the bridge via a radial transition.

According to a sixteenth aspect, the method of the fifteenth aspect or any other aspect, wherein the bridge comprises: a midpoint; a first thickness at the midpoint; a second thickness at the radial transition to the at least one leg.

According to a seventeenth aspect, the method of the sixteenth aspect or any other aspect, wherein the second thickness is greater than the first thickness.

According to an eighteenth aspect, the method of the seventeenth aspect or any other aspect, wherein a thickness of the bridge decreases linearly from the second thickness to the first thickness.

According to a nineteenth aspect, the method of the fifteenth aspect or any other aspect, wherein the first curved surface and the second curved surface form a constantly curved surface between the first edge and the second edge.

According to a twentieth aspect, the method of the eighteenth aspect or any other aspect, wherein the apex comprises a flat portion between the first curved surface and the second curved surface.

The present disclosure relates to a staple, according to a twenty-first aspect, comprising a bridge comprising: a top surface between radial tangents of two parallel legs and a radial tangent of a first inline leg, wherein the top surface is substantially non-breaking between a first edge and a second edge; an apex of the top surface along a central axis of the bridge; a first curved surface between the apex and the first edge; a second curved surface between the apex and the second edge; a relatively constant moment of inertia; a first transition area transitioning the top surface downwardly to an outer surface of each of the two parallel legs; the second transition area transitioning the top surface downwardly to an outer surface of a second inline leg, wherein: the first inline leg and the second inline leg are symmetric about the central axis; the staple is deformable from a relaxed position to a deformed position; and in the deformed position, strain at the apex of the bridge is greater than strain in the two parallel legs, the first inline leg, and the second inline leg, thereby reducing a risk of breakage of the staple.

According to a twenty-second aspect, the staple of the twenty-first aspect or any other aspect, wherein strain in a central region of the bridge is greater than strain in other portions of the bridge.

According to a twenty-third aspect, the staple of the twenty-second aspect or any other aspect, wherein the strain at the apex of the bridge is greater than strain in the first transition area or second transition area.

According to a twenty-fourth aspect, the staple of the twenty-third aspect or any other aspect, wherein each of the two parallel legs, the first inline leg, and the second inline leg are connected to the bridge via a radial transition.

According to a twenty-fifth aspect, the staple of the twenty-fourth aspect or any other aspect, wherein the bridge comprises: a midpoint; a first thickness at the midpoint; a second thickness at the radial transition to the at least one leg.

According to a twenty-sixth aspect, the staple of the twenty-fifth aspect or any other aspect, the second thickness is greater than the first thickness.

According to a twenty-seventh aspect, the staple of the twenty-sixth aspect or any other aspect, wherein a thickness of the bridge decreases linearly from the second thickness to the first thickness.

According to a twenty-eighth aspect, the staple of the twenty-seventh aspect or any other aspect, wherein the two parallel legs, first inline leg, second inline leg, and bridge are integrally formed and manufactured from a single piece of metal.

According to a twenty-ninth aspect, the staple of the twenty-eighth aspect or any other aspect, wherein the staple comprises nitinol.

According to a thirtieth aspect, the staple of the twenty-nineth aspect or any other aspect, wherein the first curved surface and the second curved surface form a substantially constantly curved surface between the first edge and the second edge.

According to thirty-first aspect, the staple of the twenty-nineth aspect or any other aspect, wherein the apex comprises a substantially flat portion between the first curved surface and the second curved surface.

According to thirty-second aspect, the staple of the thirtieth aspect or any other aspect, wherein the first transition area comprises a first divot that transitions the top surface of the bridge downwardly to the outer surface of each of the two parallel legs.

According to thirty-third aspect, the staple of the thirty-second aspect or any other aspect, wherein the first divot comprises a semi-circular perimeter.

According to thirty-fourth aspect, the staple of the thirty-third aspect or any other aspect, wherein the bridge comprises a first width proximate the first transition area.

According to thirty-fifth aspect, the staple of the thirty-fourth aspect or any other aspect, wherein the bridge comprises a second width proximate the second transition area; and the second width is less than the first width.

The present also disclosure also relates to a method of using a staple. According to a thirty-sixth aspect, the present disclosure relates to a method comprising the steps of inserting two legs of a staple into a first bony fragment of a patient; inserting at least one leg into at least one additional bony fragment of the patient; causing the staple to compress the first bony fragment and the at one additional bony fragment via strain stored in the staple, wherein: the strain at an apex of the bridge is greater than strain in the two legs or the at least one leg, thereby reducing a risk of breakage of the staple in the patient; the two legs extend from a first transition area adjacent to the bridge; at least one leg extends from a second transition area adjacent to the bridge; the bridge comprises: a top surface comprising the apex, wherein the top surface is substantially non-breaking between a first edge and a second edge; a first curved surface between the apex and the first edge; a second curved surface between the apex and the second edge; a relatively constant moment of inertia along at least a portion of the bridge; the first transition area transiting the top surface of the bridge downwardly to an outer surface of each of the two legs; and the second transition area transiting the top surface of the bridge downwardly to an outer surface of the at least one leg.

The present also disclosure relates to a staple, according to a thirty-seventh aspect, comprising a bridge comprising: a top surface between a first transition area and a second transition area, wherein the top surface is substantially non-breaking between a first edge and a second edge; an apex of the top surface along a central axis of the bridge; a first curved surface between the apex and the first edge; a second curved surface between the apex and the second edge; a relatively constant moment of inertia; the first transition area transitioning the top surface downwardly to an outer surface of a first set of parallel legs; and the second transition area transitioning the top surface downwardly to a second set of parallel legs, wherein: the central axis passes between each of the first set of parallel legs and the second set of parallel legs; the staple is deformable from a relaxed position to a deformed position; and in the deformed position, strain at the apex of the bridge is greater than strain in the first set of parallel legs and the second set of parallel lets, thereby reducing a risk of breakage of the staple.

According to a thirty-eighth aspect, the staple of the thirty-seventh aspect or any other aspect, wherein strain in a central region of the bridge is greater than strain in other portions of the bridge.

According to a thirty-nineth aspect, the staple of the thirty-eighth aspect or any other aspect, wherein the strain at the apex of the bridge is greater than strain in the first transition area or second transition area.

According to a fortieth aspect, the staple of the thirty-nineth aspect or any other aspect, wherein each of the first two parallel legs and the second two parallel legs are connected to the bridge via a radial transition.

According to a forty-first aspect, the staple of the fortieth aspect or any other aspect, wherein the first set of parallel legs, the second set of parallel legs, and bridge are integrally formed and manufactured from a single piece of metal.

According to a forty-second aspect, the staple of the forty-first aspect or any other aspect, wherein the staple comprises nitinol.

According to a forty-third aspect, the staple of the forty-second aspect or any other aspect, wherein the first curved surface and the second curved surface form a substantially constantly curved surface between the first edge and the second edge.

According to a forty-fourth aspect, the staple of the forty-third aspect or any other aspect, wherein the first transition area is substantially similar to the second transition area.

The present disclosure also relates to a staple, according to a forty-fifth aspect, comprising at least three legs connected to a bridge; the bridge comprising a width, a height, and a bridge portion between a first end and a second end, the bridge portion comprising a first edge and a second edge with a smooth, non-breaking surface therebetween, wherein: at least two of the at least three legs are connected to the bridge via a radial transition proximate the first end of the bridge; the bridge portion comprises a constant moment of inertia; the staple is deformable from a relaxed position to a deformed position; and in the deformed position, strain at an apex of the bridge is greater than strain in any of the at least three legs.

The present disclosure also relates to a method, according to a forty-sixth aspect, comprising the steps of inserting a staple held in a deformed position into two boney structures of a patient, the staple comprising: at least three legs connected to a bridge; and the bridge comprising a width, a height, and a bridge portion between a first end and a second end, the bridge portion comprising a first edge and a second edge with a smooth, non-breaking surface therebetween; and releasing the staple from the deformed position, wherein: at least two of the at least three legs are connected to the bridge via a radial transition proximate the first end of the bridge; the bridge portion comprises a constant moment of inertia; releasing the staple from the deformed position causes the staple to exert compressive force on the two boney structures; and strain at an apex of the bridge is greater than strain in any of the at least three legs.

The present disclosure also relates to a staple, according to a forty-seventh aspect, comprising a bridge between radial tangents of two opposing legs, the bridge comprising: a non-breaking top surface between a first edge and a second edge; an apex of the top surface; a first curved surface between the apex and the first edge; a second curved surface between the apex and the second edge; a relatively constant moment of inertia along at least a portion of the bridge; a first transition area transitioning the top surface of the bridge downwardly to an outer surface of each of two legs proximate a first side of the bridge; a second transition area transitioning the top surface of the bridge downwardly to an outer surface of at least one leg proximate the second side of the bridge, wherein: the staple is deformable from a relaxed position to a deformed position; and strain in the bridge is greater than or equal to strain in the two legs or the at least one leg, thereby reducing a risk of breakage of the staple.

The present disclosure also relates to a method, according to a forty-eighth aspect, comprising the steps of inserting a staple into one or more bony fragments of a patient in a deformed position, the staple comprising: a bridge between radial tangents of two opposing legs, the bridge comprising: a non-breaking top surface between a first edge and a second edge; an apex of the top surface; a first curved surface between the apex and the first edge; a second curved surface between the apex and the second edge; a relatively constant moment of inertia along at least a portion of the bridge; a first transition area transitioning the top surface of the bridge downwardly to an outer surface of each of two legs proximate a first side of the bridge; a second transition area transitioning the top surface of the bridge downwardly to an outer surface of the at least one leg proximate the second side of the bridge, wherein: causing the staple to attempt to move from the deformed position to a relaxed position such that the staple compresses the one or more bony fragments of the patient and strain in the bridge is greater than or equal to strain in the two legs or the at least one leg, thereby reducing a risk of breakage of the staple.

These and other aspects, features, and benefits of the claimed invention(s) will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE FIGURES

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein.

DETAILED DESCRIPTION

Figure 1:
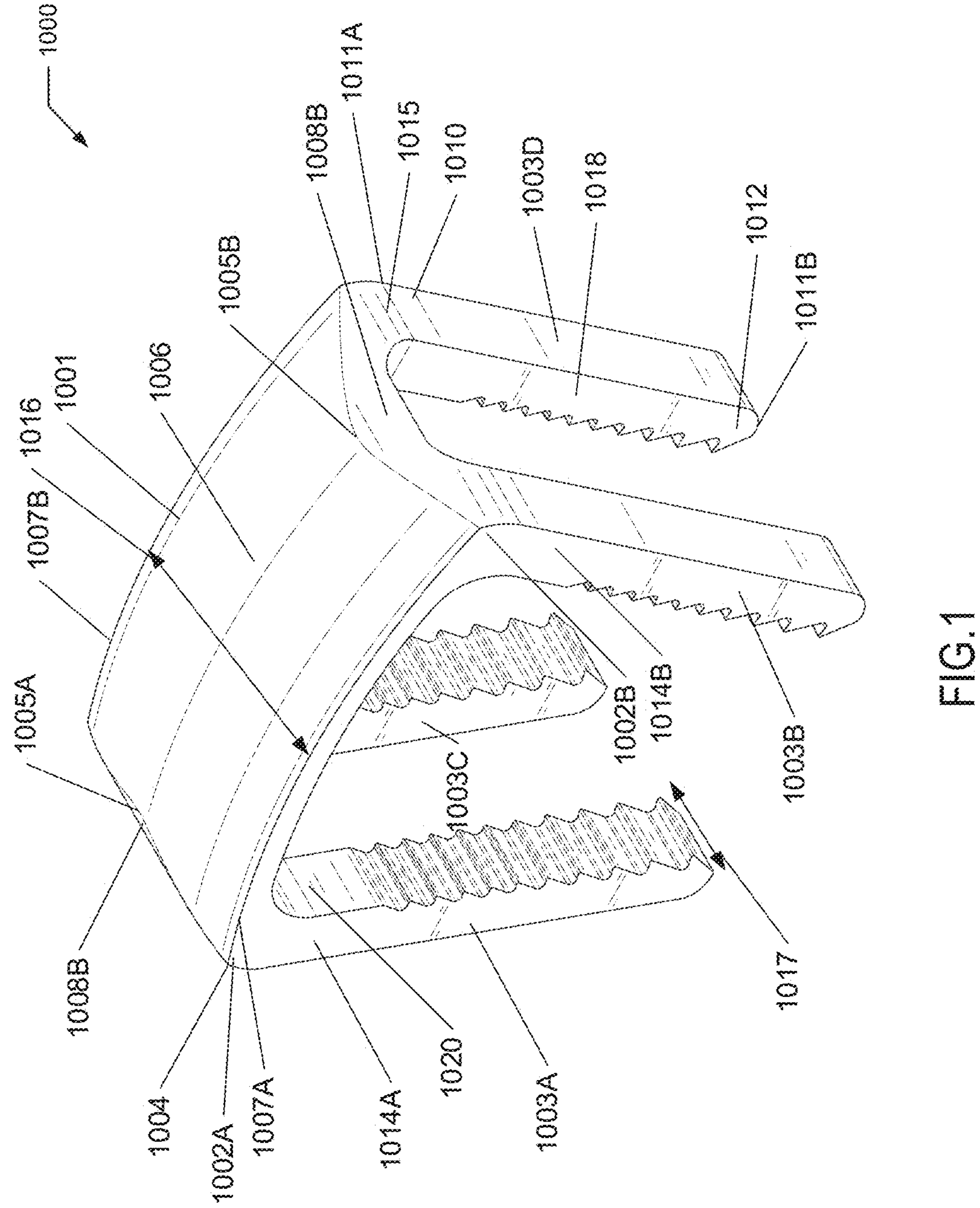
FIG. 1 shows a perspective view of an exemplary staple, according to one embodiment of the present disclosure.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Overview

Aspects of the present disclosure generally relate to compression and fixation systems, such as, for example, staples. In various embodiments, the present compression and fixation systems include one or more materials that demonstrate superelasticity. In at least one embodiment, superelasticity refers to a material's ability to undergo large deformations and immediately return (e.g., or attempt to return) to the material's undeformed shape upon removal of an external load (e.g., that causes deformation of the material from the undeformed shape). In some embodiments, the staple may be formed from any suitable metal, such as stainless steel, titanium/titanium alloys, or cobalt-based alloys, nitinol, or any other suitable material. In various embodiments, a staple of the present disclosure demonstrates superelasticity such that the staple attempts to return to an undeformed shape (e.g., a first state) following deformation to a deformed shape (e.g., a second state). According to one embodiment, the staple is inserted to a target site in the deformed shape such that the reverse deformation of the staple applies compressive and/or fixative forces to the target site. For example, the staple includes opposing pairs of legs connected by a bridge. In this example, while being held in a deformed state by an external force, the staple is inserted into one or more bony fragments such that the first pair of legs lie in a first of the one or more bony fragments and the second, opposing pair of legs lie in a second of the one or more bony fragments. In the same example, the external force is removed and the staple attempts to return to a non-deformed state including substantial bending of the staple bridge that causes the opposing pairs of legs to translate toward each other. In this example, the reverse-deformation of the staple causes the opposing pairs of legs to compress the first bony fragment and the second bony fragment together, thereby promoting healing techniques (e.g., such as bone fusion) via bone resorption and ossification.

Exemplary Embodiments

Referring now to the figures, for the purposes of example and explanation of the fundamental processes and components of the disclosed systems and processes, reference is made to FIG. 1, which illustrates an exemplary staple 1000 according to one embodiment of the present disclosure. As will be understood and appreciated, the exemplary staple 100 shown in FIG. 1 represents merely one approach or embodiment of the present system, and other aspects are used according to various embodiments of the present system.

FIG. 1 shows a perspective view of an exemplary staple 1000. In various embodiments, the staple 1000 includes a bridge 1001 and legs 1003 A-D. According to one embodiment, the staple 1000 size (e.g., bridge 1001 length×leg 1003A-D length) may be greater than, less than or equal to about 18.0 mm×20.0 mm. In various embodiments, the bridge 1001 includes a substantially rectangular shape (e.g., four sides connected at four vertices). In some embodiments, the bridge 1001 includes a shape demonstrating concavity toward a center of the shape (e.g., similar to an hourglass shape).

In at least one embodiment, the bridge 1001 includes substantially curved or radial transitions between the legs 1003A-D, shoulders 1015A-D (FIG. 4), and the bridge 1001 (e.g., at top surface 1006 and/or a bridge bottom surface 4001 (FIG. 4)). In at least one embodiment, the top surface 1006 includes one or more curved surfaces (e.g., at least a first curved surface and a second curved surface). In at least one embodiment, the substantially curved construction of the transitions and the substantially low profile construction of the bridge 1001 results in transfer of stress concentrations from undesirable regions, such as the connections between the staple bridge and staple legs, to more desirable regions, such as throughout the bridge 1001. In various embodiments, the movement of stress concentrations from undesirable to desirable regions advantageously reduces strain at the connections between the staple bridge and the staple legs, and, thus, reduces a likelihood of breakage between the staple bridge and one or more of the staple legs.

As described herein, the staple 1000 is deformable (e.g., bendable) between a first position and a second position (e.g., a deformed position and a relaxed position). Previous staples deform between first and second positions by undergoing bending substantially at the connections between the staple bridge and staple legs; however, this approach results in a large concentration of stress and, as a result, strain at the connections therebetween. The concentration of stress and strain at the transitions between the staple legs and staple bridge may reduce a durability of the staple and increase a likelihood of undesirable staple leg deformation or breakage. In at least one embodiment, the staple 1000 (and other staples described herein, such as the staple 9000 shown in FIG. 9) differ from previous approaches by undergoing bending substantially along the bridge 1001 (e.g., or bridge 9001), thereby moving stress and strain concentrations from the transitions between the bridge 1001 and legs 1003A-D to the bridge 1001 itself. Thus, in one or more embodiments, the staples described herein overcome deficits of previous staples by concentrating staple bending in the staple bridge and providing a substantially non-breaking bridge top surface to distribute strain substantially equally throughout the bridge and to preserve a low profile nature of the staple.

In various embodiments, the legs 1003A, 1003C are substantially parallel and the legs 1003B, 1003D are substantially parallel. In one or more embodiments, the parallel characteristic of legs 1003A, 1003C and of legs 1003B, 1003D is maintained regardless of a deformation state of the staple 1000. For example, the legs 1003A, 1003C remain substantially parallel as the staple 1000 transitions to a deformed state (e.g., via bending substantially along the bridge 1001). In at least one embodiment, each leg 1003A-D transitions to the bridge 1001 at a corner 1002. In one or more embodiments, the corner 1002 is rounded to enhance a low profile feature of the bridge 1001, the roundedness reducing a likelihood of the corner 1002 piercing or lacerating tissue, or becoming caught on an external element (e.g., such as a wound wrapping, clothing, etc.). In at least one embodiment, each corner 1002 defines a radius 1004. In various embodiments, the radius 1004 measures at least about 0.5 mm, or about 0.5-1.0 mm, 1.0-1.5 mm, 1.5 mm, 1.5-2.0 mm, 2.0 mm, 2.0-2.5 mm, 2.5-3.0 mm, or less than about 3.0 mm. In various embodiments, the radius 1004 defines a generally concave profile of each corner 1002.

In at least one embodiment, the bridge 1001 demonstrates a substantially constant moment of inertia across an entire length thereof. In one or more embodiments, the bridge 1001 includes a first end 1005A and a second end 1005B, and the bridge 1001 demonstrates a constant moment of inertia along the length of the bridge 1001 between the first end 1005A and the second end 1005B. According to one embodiment, the substantially constant moment of inertia provides for more equitable distribution of stress concentrations throughout the bridge 1001 as compared to stress concentration distribution of previous staple bridges (e.g., that include discontinuous moments of inertia). In one example, a previous staple bridge demonstrates discontinuous moments of inertia along a length thereof. In this example, the previous staple bridge concentrates stress at bridge regions where moment of inertia undergoes a delta, thereby introducing potential failure points along the length of the staple bridge. In contrast, staple bridges of the present disclosure can demonstrate a continuous moment of inertia across their entire length (e.g., or a substantial portion thereof), and, thereby, reduce a likelihood staple failure by dispersing stress substantially equally throughout entire bridge.

In various embodiments, the bridge 1001 is curved between the first end 1005A and the second end 1005B. In at least one embodiment, the curved and low profile geometry of the bridge 1001 contributes to the improved torsional stability of the bridge staple 1000 by reducing a risk of the bridge 1001 becoming caught on and/or disturbed by external surfaces.

In at least one embodiment, the bridge 1001 includes a substantially smooth top surface 1006 between the first end 1005A and the second end 1005B, and between a first edge 1007A and a second edge 1007B. In one or more embodiments, the top surface 1006 is substantially smooth and non-breaking. According to one embodiment, the non-breaking quality of the top surface 1006 distributes stress substantially equally throughout the bridge 1001, thereby reducing a prevalence of stress concentrations (e.g., as compared to previous staples that demonstrate discontinuous bridge surfaces) and improving durability of the staple 1000. In various embodiments, due to the equal distribution of stress, the bridge 1001 experiences substantially uniform strain and, thus, the bridge 1001 demonstrates a substantially constant moment of inertia. For example, the concentration of stress to and distribution of stress throughout the bridge 1001 causes the bridge 1001 to undergo strain substantially uniformly (e.g., the rate of strain throughout the bridge 1001 in response to an external force is substantially equal at all points within throughout the bridge 1001). In this example, by undergoing strain substantially uniformly, the bridge 1001 maintains a substantially constant moment of inertia.

In at least one embodiment, the bridge 1001 includes side surfaces 1008A, 1008B. In various embodiments, the top surface 1006 transitions to the side surface 1008A at the first end 1005A and to the side surface 1008B at the second end 1005B. The transition between the top surface 1006 and the side surfaces 1008A, 1008B can be non-breaking, thereby, promote the equal distribution of stress throughout the bridge 1001. In at least one embodiment, the side surfaces 1008A, 1008B transition the bridge 1001 to an outer leg surface 1010 of each leg 1003A-D. For example, the side surfaces 1008A, 1008B define radii for transitioning the bridge 1001 to each outer leg surface 1010. In one or more embodiments, the top surface 1006 transitions downwardly to the side surfaces 1008A, 1008B and/or to the outer leg surface 1010 of each leg 1003A-D. In one example, the side surfaces 1008A, 1008B demonstrate a generally concave profile that transitions the top surface 1006 to the outer leg surface 1010. In another example, the top surface 1006 transitions downwardly and directly to the outer leg surface 1010. In the same example, the top surface 1006 can also transition downwardly at the edges 1007A, 1007B to a side surface 1014 of each leg 1003A-D and a side surface 2009 (see FIG. 2) of the bridge 1001.

In at least one embodiment, portions of the bridge 1001 extend past the first and second ends 1005A, 1005B. In various embodiments, the extending portions include a top surface substantially coplanar with the top surface 1006 of the bridge 1001 and a bottom surface substantially coplanar or superior to a bottom surface 4001 (FIG. 4) of the bridge 1001. In one or more embodiments, the extending portions are for increasing ease of deforming the staple 1000 between a first (e.g., deformed) and a second (e.g., relaxed) position described herein by providing surfaces to which deforming forces are applied. According to one embodiment, the coplanar or superior position provides sufficient space for insertion of tools between the extending portions (and other features, as suitable) and a target region, such as a bone surface, thereby allowing for manipulation of the extending portions.

In various embodiments, the legs 1003A-D are integrally formed with the bridge 1001. In at least one embodiment, each leg 1003A-D demonstrates a substantially rectangular cross-section. The legs 1003A-D can demonstrate any suitable shape (e.g., generally cylindrical, serpentine, obround, oval, tubular, etc.). The legs 1003A-D can demonstrate differing shape. For example, the legs 1003A-B can demonstrate a generally rectangular shape and the legs 1003C-D can demonstrate a generally cylindrical shape. In one or more embodiments, each leg 1003 A-D extends from the bridge 1001 between a first end 1011A and a second end 1011B. In various embodiments, the legs 1003A-D are generally straight between the first end 1011A and second end 1011B. In some embodiments, one or more of the legs 1003A-D demonstrate a concave or convex curvature between the first end 1011A and the second end 1011B.

In at least one embodiment, each leg 1003A-D includes a tip 1012. The tip 1012 can define the second end 1011B. According to one embodiment, the tip 1012 includes a wedge-shape for improving ease guiding and inserting the staple 1000 to a target site. In some embodiments, the tip 1012 tapers toward the second end 1011B. In at least one embodiment, the tip 1012 is blunted. For example, the tip 1012 demonstrates a generally rectangular or cylindrical shape of constant dimension (e.g., the tip 1012 is not tapered). The tip 1012 can include any suitable shape (e.g., points, rounded edges, blocked edges, chamfered edges, beveled edges, etc.) or combination of suitable shapes.

In various embodiments, the shoulder 1015 connects each leg 1003A-D to the bridge 1001. In at least one embodiment, the shoulder 1015 transitions a depth 1016 of the bridge 1001 to a depth 1017 of each leg 1003A-D. In one or more embodiments, the depth 1016 measures at least about 8.0 mm, or about 8.0-8.5 mm, 8.5-9.0 mm, 9.0-9.5 mm, 9.5-10.0 mm, 10.0-10.5 mm, 10.5 mm, 10.5-11.0 mm, 11.0-11.5 mm, or 11.5-12.0 mm, or less than about 12.0 mm. In some embodiments, the depth 1016 tapers from a first magnitude at the first end 1005A and the second end 1005B to a second magnitude toward a central bridge portion spanning a length of the bridge 1001 therebetween. In various embodiments, the shoulder 1015 transitions a depth 1016 of the bridge 1001 from a first magnitude to a second magnitude.

In at least one embodiment, the depth 1017 measures at least about 1.0 mm, or about 1.0-4.0 mm, 0.5-1.0 mm, 1.0-1.5 mm, 1.5-2.0 mm, 2.0-2.5 mm, 2.5 mm, 2.5-3.0 mm, 3.0-3.5 mm, or 3.5-4.0 mm, or less than about 4.0 mm. In one or more embodiments, the shoulder 1015 defines a radius 1017 for transitioning the bridge 1001 to each leg 1003A-D. In various embodiments, the radius 1017 measures at least about 1.0 mm, or about 1.0-4.0 mm, 0.5-1.0 mm, 1.0-1.5 mm, 1.5 mm, 1.5-2.0 mm, 2.0-2.5 mm, 2.5 mm, 2.5-3.0 mm, 3.0-3.5 mm, or 3.5-4.0 mm, or less than about 4.0 mm.

According to one embodiment, the shoulder 1015 includes a substantially rectangular shape or a shape substantially similar to a shape of the legs 1003A-D. According to one embodiment, the shoulder 1015 forms a curved transition between the bridge 1001 and a corresponding leg 1003A-D. The curved transition can define a corner 1002. In various embodiments, the curved transitions result in stress concentrations (e.g., that act as structural weak or failure points in previous approaches) at or throughout the bridge 1001. In at least one embodiment, the elimination or substantial reduction of angular transitions between the bridge 1001 and legs 1003A-D minimizes stress concentrations and, in combination with a flat construction (or flat portion) of the bridge 1001, moves a substantial proportion of stress concentrations still present from the connections to the bridge 1001 where they are equally distributed throughout the length thereof. In one or more embodiments, the concentration to and substantially equal distribution of stress throughout the bridge 1001 results in the bridge 1001 demonstrating a substantially constant moment of inertia.

Figure 2:
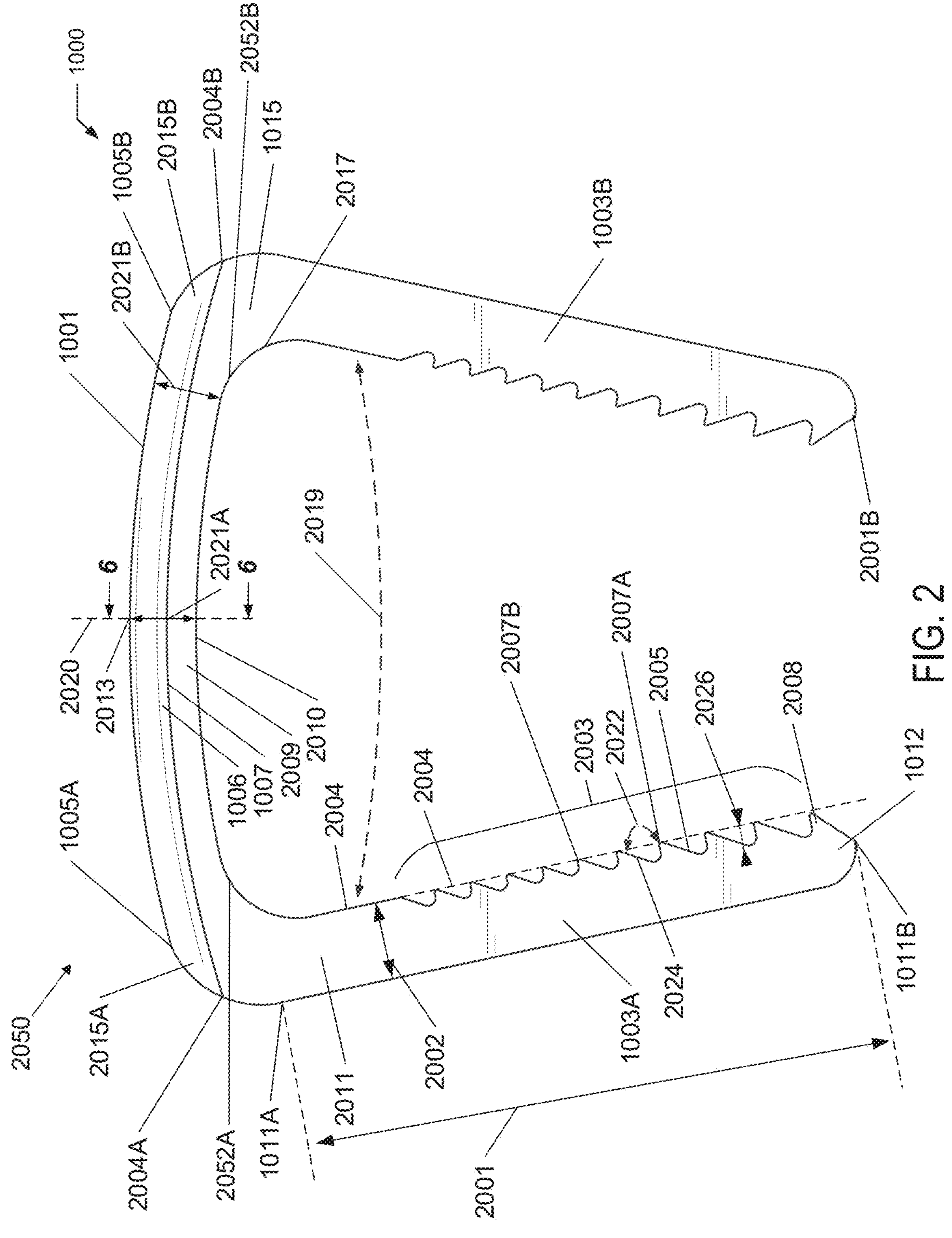
FIG. 2 shows a front view of an exemplary staple, according to one embodiment of the present disclosure.

FIG. 2 shows a front view of the staple 1000 including a bridge 1001 and legs 1003A-B. The following description of legs 1003A-B can apply to the legs 1003C-D shown in FIG. 1. In at least one embodiment, each leg 1003A-B includes a length 2001 between the first end 1011A and the second end 1011B. In various embodiments, the length 2001 measures about 12.0-24.0 mm, 12.0-14.0 mm, 14.0-16.0 mm, 16.0-18.0 mm, 18.0 mm, 18.0-20.0 mm, 20.0-22.0 mm, or 22.0-24.0 mm. In one or more embodiments, each leg 1003A-B includes a thickness 2002 (e.g., between an outer surface 1010 and an inner surface 1020 shown in FIG. 1). In at least one embodiment, the thickness 2002 measures at least about 0.5 mm, or about 0.5-6.0 mm, 0.5-1.0 mm, 1.0-2.0 mm, 2.0 mm, 2.0-3.0 mm, 3.0-4.0 mm, 4.0-5.0 mm, or 5.0-6.0 mm, or less than about 6.0 mm. In some embodiments, the thickness 2002 tapers between the ends 1011A-1011B. For example, the thickness 2002 increases toward the end 1011A.

In various embodiments, the staple 1000 includes one or more teeth sections 2003. In at least one embodiment, the teeth section 2003 is cut into each leg 1003A-B (e.g., and legs 1003C-D shown in FIG. 1). According to one embodiment, the teeth section 2003 includes a plurality of teeth 2005. In some embodiments, the teeth section 2003 is located on an internal face of each of the legs 1003A-B (e.g., inner surface 1020). In various embodiments, the teeth section 2003 extends along the entire length of each leg 1003A-B. According to one embodiment, the teeth section 2003 extends along a partial length of the legs 1003A-B. The length of the teeth section 2003 can vary between two or more legs 1003A-B. In various embodiments, the teeth section 2003 demonstrates a wedge, curved, or straight shape, or any combination thereof. In one or more embodiments, a teeth section 2003 of each of leg 1003A-B demonstrate a different (or the same) number of teeth 2005. In various embodiments, one or more legs 1003A-B include different sized or shaped teeth 2005 (e.g., for example, the legs 1003A, 1003C include teeth 2005 of a first shape and the legs 1003B, 1003D include teeth 2005 of a second shape).

In at least one embodiment, ends 2007A, 2007B (e.g., sharpest points) of each tooth 2005 lie in the same plane as the inner surface of the corresponding leg. According to one embodiment, the plane of the inner surface of the leg 1003A is shown approximately as the reference line 2004 and is representative of the planes of the legs 1003B-D. In some embodiments, ends 2007A, 2007B of each tooth 2005 are non-coplanar. In one example, ends 2007A, 2007B of each tooth 2005 taper along the length of the corresponding teeth section 2003. In various embodiments, each teeth section 2003 includes a variable number of teeth 2005, the variable number being greater than, less than, or equal to about 4, 6, 8, 10, 14, 16, 18, or 20 (and including values therebetween). In one or more embodiments, the number of teeth 2005 included in the teeth section 2003 depends on a length of one or more legs 1003A-D (e.g., a staple with longer legs may have more teeth 2005). In at least one embodiment, the teeth section 2005 includes a terminal tooth 2008 toward the end 1011B. The terminal tooth 2008 can be substantially similar to other teeth 2005 of the teeth section 2003). In one or more embodiment, the terminal tooth 2008 defines a shape of the tip 1012. For example, the terminal tooth 2008 defines a wedge shape of the tip 1012.

In at least one embodiment, each tooth 2005 includes a tooth angle 2022 that generally refers to an angle between the end 2007A and a sloped surface 2024 of the tooth 2005. According to one embodiment, the tooth angle 2022 measures at least about 45.0 degrees, or about 45.0-60.0 degrees, about 45.0 degrees, about 45.0-48.0 degrees, about 44.0-48.0 degrees, about 48.0-52.0 degrees, about 52.0-56.0 degrees, about 56.0-60.0 degrees, about 60.0 degrees, or less than about 60.0 degrees. In one or more embodiments, all of the teeth 2005 include the tooth angle 2022 of the same magnitude. In various embodiments, a tooth 2005 at the end 1011B is at a tooth angle 2022 other than 60 degrees, such as for example, 45 degrees. In one or more embodiments, each tooth 2005 may include any suitable angle or angles, including but not limited to about 20.0-85.0 degrees. According to one embodiment, the tooth angle 2802 of each respective tooth 2005 in a teeth section 2003 decreases towards the end 1011B.

In one or more embodiments, each tooth 2005 includes a width 2026 that measures greater than, less than, or equal to about 0.01-1.00 mm, 0.36 mm, 0.41 mm, 0.46 mm, 0.51 mm, 0.56 mm, or about 0.58 mm. According to one embodiment, the width 2026 of each respective tooth 2005 in a teeth section 2003 increases towards the end 1011B. For example, a tooth 2005 at a bottom of a teeth section 2003 (e.g., at the end 1011B) includes a width 2026 of about 0.58 mm and a second tooth 2005 at a top of the teeth section 2003 (e.g., towards the 1011A) includes a width 2026 of about 0.36 mm. In the same example, a plurality of the teeth 2005 located toward the bottom of the teeth section 2003 are larger (e.g., wider) than a plurality of the teeth 2005 located toward the top of the teeth section 2003. As will be understood from discussions herein, all of the teeth 2005 of the staple 1000 may be substantially the same shape, depth, etc. In various embodiments, the number of teeth 2005, width 2026, angle 2022, etc. may vary along the length of a connected leg (e.g., legs 1003A-D).

In various embodiments, the bridge 1001 includes a side surface 2009 between the edge 1007 and an edge 2010. In various embodiments, the edge 1007 transitions the top surface 1006 to a side surface 2009. In at least one embodiment, the edge 1007 provides a substantially non-breaking transition between the top surface 1006 and the side surface 2009. For example, the edge 1007 defines a non-breaking curve for transitioning between the top surface 1006 and the side surface 1009. In some embodiments, the edge 1007 defines an angular transition between the top surface 1006 and side surface 2009. In one or more embodiments, the side surface 2009 is coplanar with a side surface 2011 of each leg 1003A-D.

In at least one embodiment, at least a portion of the side surface 2009 is not coplanar with the side surface 2011. In various embodiments, the bridge 1001 includes a central bridge portion 2013 between ends 1005A, 1005B. In one or more embodiments, the bridge 1001 includes outer portions 2015A, 2015B that bound the central region 2013. In at least one embodiment, the central bridge portion 1001 demonstrates a first depth that is less than a depth of each outer portion 2015A, 2015B. In various embodiments, the side surface 2009 transitions the first depth of the central bridge portion 1001 to the second depth of each outer portion 2015A, 2015B. In one example, the side surface 2009 includes a non-breaking, concave curve toward each end 1005A, 1005B, and the non-breaking, concave curve transitions the first depth to the second depth. In another example, the side surface 2009 includes a non-breaking, concave curve that transitions to a non-breaking, convex curve, and the non-breaking concave and convex curves transition the first depth to the second depth.

According to some embodiments, the staple 1000 includes at least one transition area 2050 defined as an area between the bridge 1001 and the outer surface of each leg 1003A-D (e.g., outer surface 1010 shown in FIG. 1). In one embodiment, the at least one transition area 2050 may include a portion of the top surface 1006 of the bridge 1001. In other embodiments, the at least one transition area 2050 may include a downwardly sloping portion of the bridge 1001. In some embodiments, the bridge 1001 is defined between at least a first radial tangent 2052A and a second radial tangent 2052B such that the at least one transition area 2050 is an area of the bridge 1001 disposed between the first or a second radial tangent 2052A-B and an end 2004A-B (with the bridge 1001 between first and second radial tangents 2052A-B).

In at least one embodiment, each shoulder 1015 includes a radius 2017 for transitioning the bridge 1001 to each corresponding leg. In one or more embodiments, the radius 2017 measures at least about 0.5 mm, or about 0.5-4.0 mm, 0.5-1.0 mm, 1.0-1.5 mm, 1.5 mm, 1.5-2.0 mm, 2.0 mm, 2.0-2.5 mm, 2.5-3.0 mm, 3.0-3.5 mm, or 3.5-4.0 mm, or less than about 4.0 mm. In various embodiments, the staple 1000 demonstrates a curvature 2019 (e.g., when the staple 1000 is in a non-deformed state, also referred to as a first state). In one or more embodiments, the curvature 2019 measures at least about 5 degrees, or about 5-45 degrees, 5-10 degrees, 10-15 degrees, 16 degrees, 15-20 degrees, 20-25 degrees, 24 degrees, 25-30 degrees, 30-35 degrees, 35-40 degrees, or 40-45 degrees, or less than about 45 degrees. According to one embodiment, the curvature 2019 decreases as the staple 1000 deforms between a non-deformed state (e.g., as shown in FIGS. 1-8) and a deformed state (not shown, also referred to as a second state). In one example, as the staple 1000 transitions to a deformed state, the curvature 2019 decreases from about 24 degrees to 0 degrees.

In at least one embodiment, the bridge 1001 includes a bridge thickness 2021A, 2021B. In some embodiments, the bridge 1001 demonstrates a substantially constant or symmetric thickness (e.g., thicknesses 2021A, 2021B are substantially equal). In some embodiments, the bridge 1001 demonstrates one or more thicknesses (e.g., a first thickness and a second thickness) in varying locations of the bridge 1001, such as a midpoint of the bridge 1001 and/or a transition to at least one of legs 1003A-D. In some embodiments, the transition to the at least one of legs 1003A-D may be radial. In various embodiments, the thickness 2021A, 2021B measures at least about 0.5 mm, or about 0.5-4.0 mm, 0.5-1.0 mm, 1.0-1.5 mm, 1.2 mm, 1.22 mm, 1.5 mm, 1.52 mm, 1.55 mm, 1.5-2.0 mm, 1.6 mm, 1.62 mm, 1.69 mm, 1.7 mm, 1.74 mm, 1.92 mm, 2.0 mm, 2.0-2.5 mm, 2.5-3.0 mm, 3.0-3.5 mm, or 3.5-4.0 mm, or less than about 4.0 mm. In at least one embodiment, the bridge 1001 demonstrates variable thickness (e.g., thickness 2021A is greater than thickness 2021B, or vice versa). In one or more embodiments, the bridge 1001 demonstrates the thickness 2021A in the central region 2013 and demonstrates the thickness 2021B at outer portions 2015A, 2015B, the thickness 2021A measuring greater than or less than the thickness 2021B. The thickness 2021A may differ from the thickness 2021B by at least about 0.01 mm, or about 0.01 mm-0.5 mm, 0.01 mm, 0.02 mm, 0.04 mm, 0.05 mm, 0.05-0.1 mm, 0.1-0.2 mm, 0.2-0.3 mm, 0.3-0.4 mm, or 0.4-0.5 mm, or less than about 0.5 mm.

Figure 3:
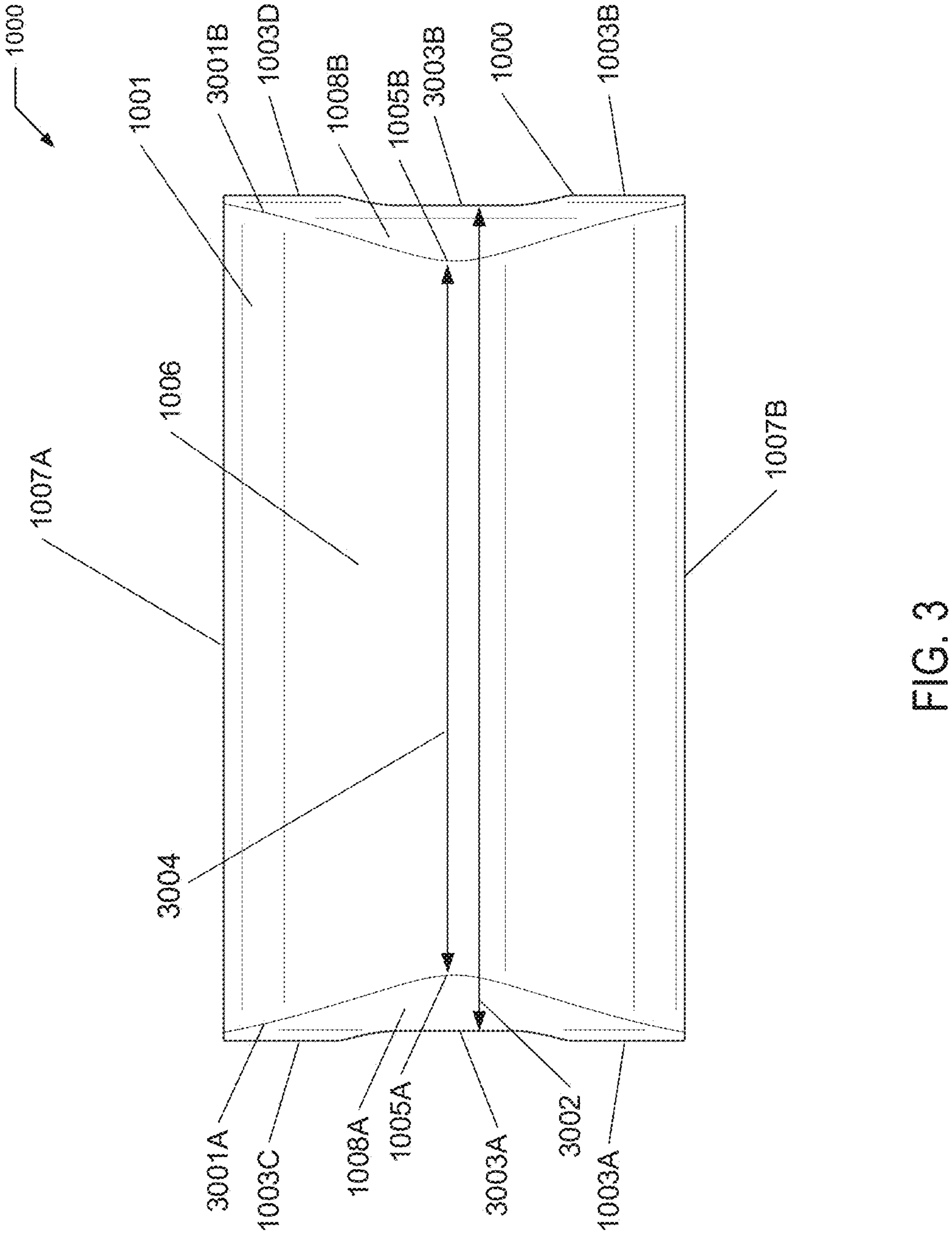
FIG. 3 shows a top view of an exemplary staple, according to one embodiment of the present disclosure.
Figure 27:
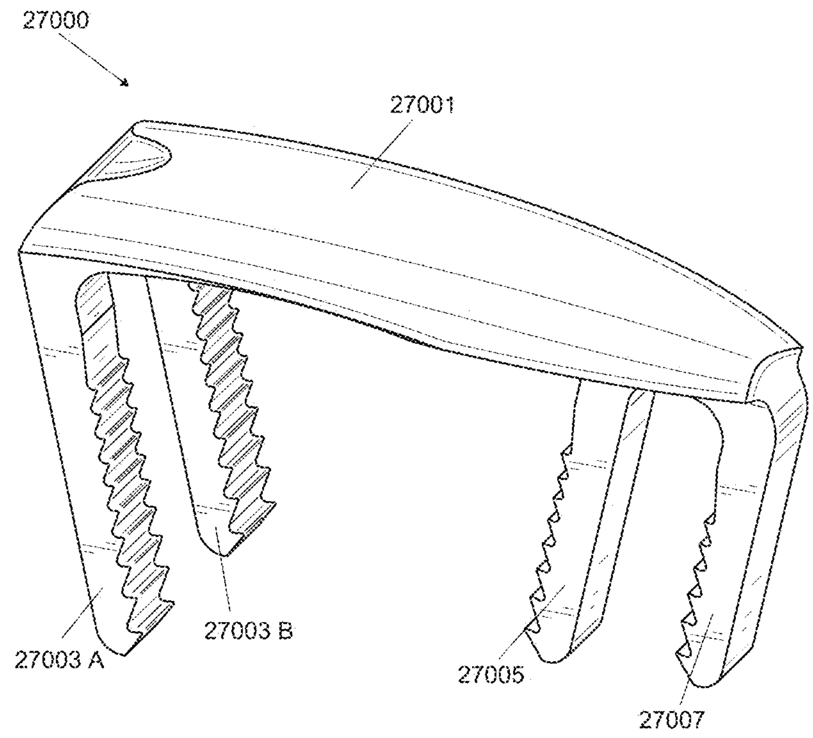
FIG. 27 shows a perspective view of an exemplary staple, according to one embodiment of the present disclosure.
Figure 28:
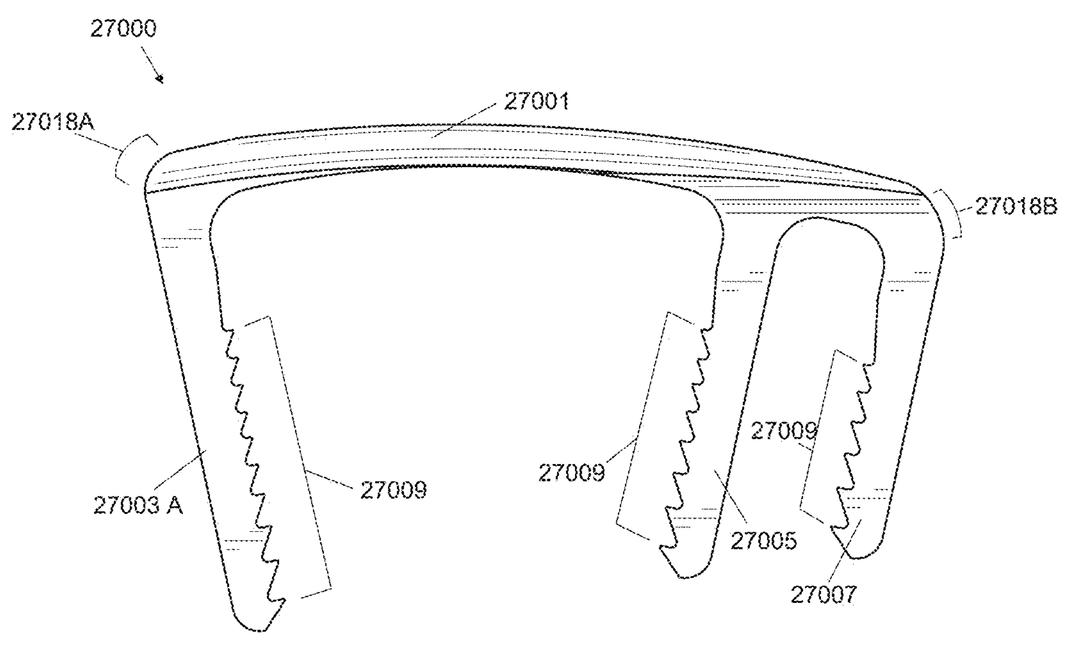
FIG. 28 shows a front view of an exemplary staple, according to one embodiment of the present disclosure.
Figure 29:
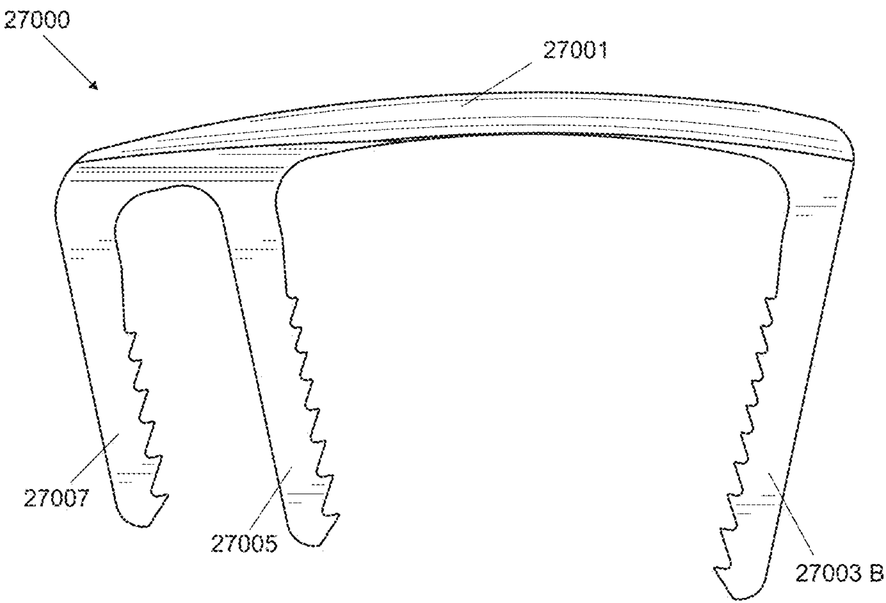
FIG. 29 shows a back view of an exemplary staple, according to one embodiment of the present disclosure.
Figure 30:
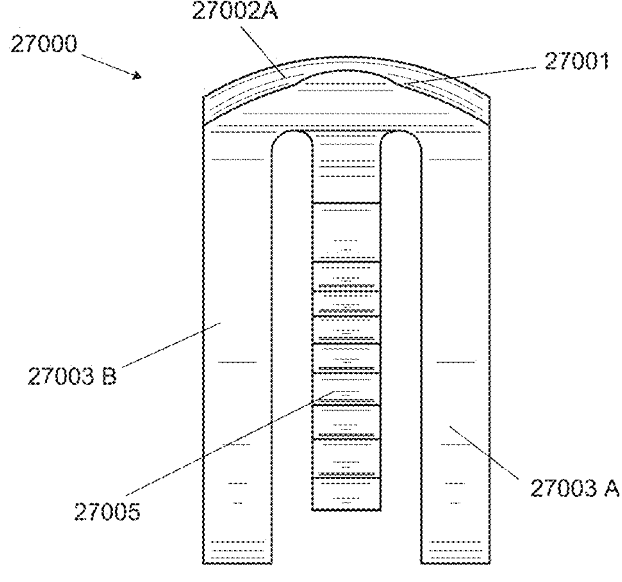
FIG. 30 shows a side view of an exemplary staple, according to one embodiment of the present disclosure.
Figure 31:
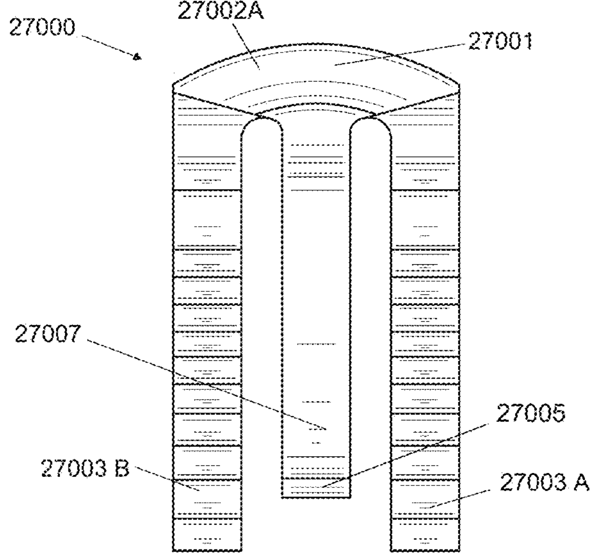
FIG. 31 shows a side view of an exemplary staple, according to one embodiment of the present disclosure.

As will be understood from discussions herein, the bridge 1001 of the staple 1000 (or any bridge and/or staple discussed herein) demonstrates a substantially constant moment of inertia. In various embodiments, the constant moment of inertia is relative to the x-axis (horizontal axis) along a length of the bridge (e.g., length 3004 as shown in FIG. 3) of the bridge 1001 in the view shown in FIG. 2. In at least one embodiment, the moment of inertia represents the resistance to bending of the bridge in the manner it would be deformed (e.g., from a relaxed state to a deformed state). As one example, three cross-sections are taken: 1) at a right plane through the tangent point between the bridge arc and the radial point of the right shoulder (for the staple shown in FIGS. 9 and 27, the tangent point between the bridge arc and the radial point of the first inline leg or second inline leg may be used); 2) at a left plane through the tangent point between the bridge arc and the radial point of the left shoulder; and 3) through a midpoint of the bridge (e.g., center plane), each cross-section resulting in a relatively constant moment of inertia.

Figure 6:
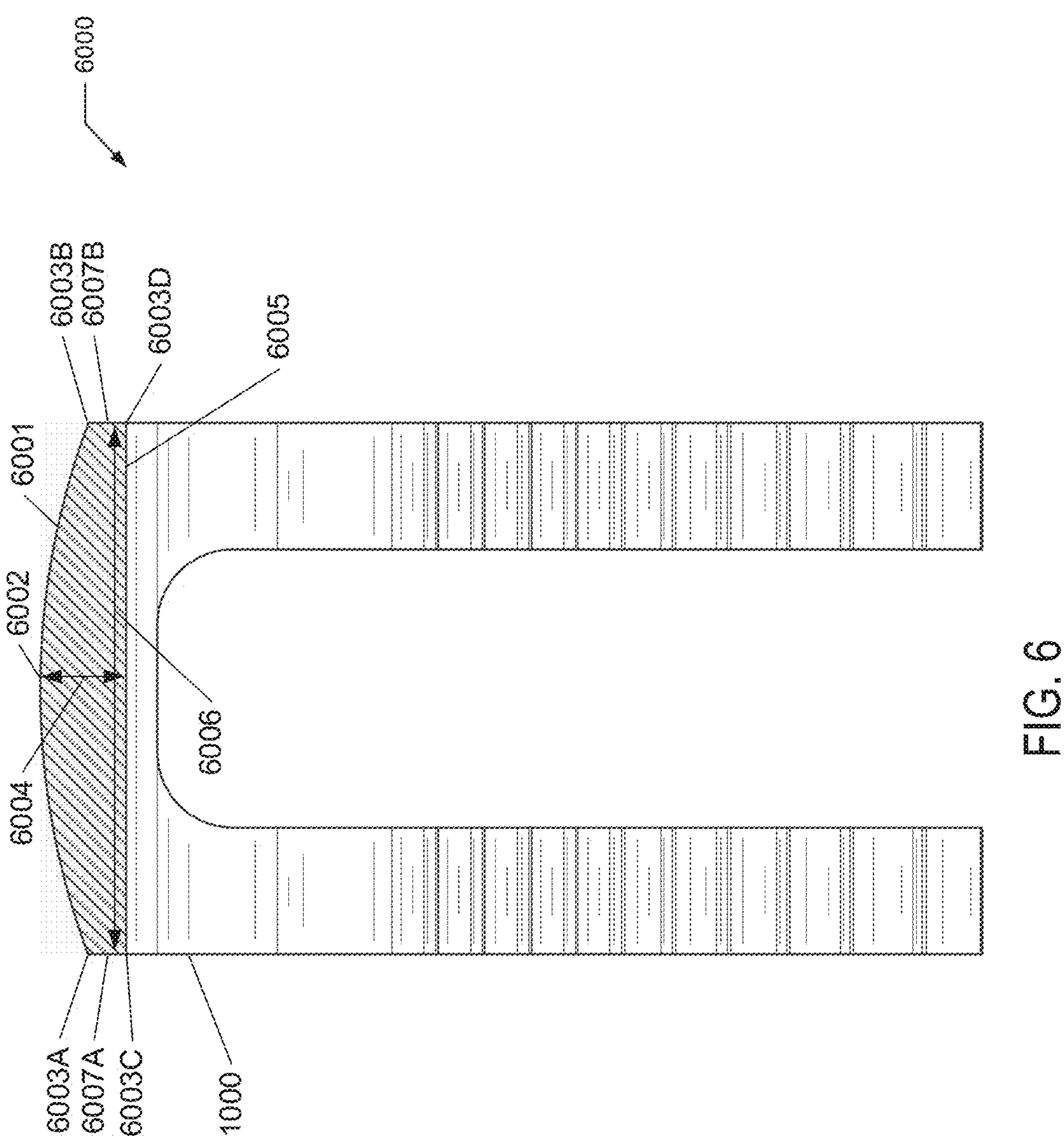
FIG. 6 shows a cross-section of an exemplary staple, according to one embodiment of the present disclosure.

According to one embodiment, section line 2020 defines a cross-section 6000 shown in FIG. 6.

FIG. 3 shows a top view of the staple 1000. In various embodiments, the bridge 1001 includes edges 3001A, 3001B. In one or more embodiments, the edges 3001A, 3001B define ends 1005A, 1005B. According to one embodiment, each edge 3001A, 3001B demonstrates a substantially continuous curvature between the edges 1007A, 1007B. In at least one embodiment, the top surface 1006 of the bridge 1001 is substantially curved and non-breaking between the edges 1007A, 1007B and the edges 3001A, 3001B. In at least one embodiment, the bridge 1001 includes edges 3003A, 3003B. According to one embodiment, the edges 3001A, 3003A define the side surface 1008A, and the edges 3001B, 3003B define the side surface 1008B. In various embodiments, the side surface 1008A is substantially curved and non-breaking between the edges 3001A, 3003A, and the side surface 1008B is substantially curved and non-breaking between the edges 3001B, 3003B.

In at least one embodiment, the side surfaces 1008A, 1008B define substantially non-breaking transitions between the top surface 1006 and an outer surface of each leg 1003A-D (e.g., outer surface 1010 shown in FIG. 1). In some embodiments, the top surface 1005 extends to the edges 3003A, 3003B. For example, the top surface 1006 is curved and substantially non-breaking between the edges 3003A, 3003B and the edges 1007A, 1007B. In at least one embodiment, the bridge 1001 includes one or more transitional surfaces between the edge 1007A, 1007B and the top surface 1006. In one example, a transitional surface generally surrounds the top surface 1006 and defines a non-breaking transition between the top surface 1006 and the edges 1007A, 1007B (e.g., or each side surface 2009 of the bridge 1001 as shown in FIG. 2).

In one or more embodiments, the bridge 1001 includes a length 3002 between the edges 3003A, 3003B. According to one embodiment, the length 3002 measures at least about 14.0 mm, or about 14.0-26.0 mm, 14.0-16.0 mm, 16.0-18.0 mm, 18.0 mm, 18.0-20.0 mm, 20.0 mm, 20.0-22.0 mm, 22.0-24.0 mm, or 24.0-26.0 mm, or less than about 26.0 mm. In various embodiments, the top surface 1006 includes a length 3004 between the ends 1005A, 1005B. In at least one embodiment, the length 3004 measures at least about 12.0 mm, or about 12.0-20.0 mm, 12.0-13.0 mm, 13.0-14.0 mm, 14.0-15.0 mm, 15.0-16.0 mm, 16.3 mm, 16.0-17.0 mm, 17.0-18.0 mm, 18.0-19.0 mm, or 19.0-20.0 mm, or less than about 20.0 mm.

Figure 4:
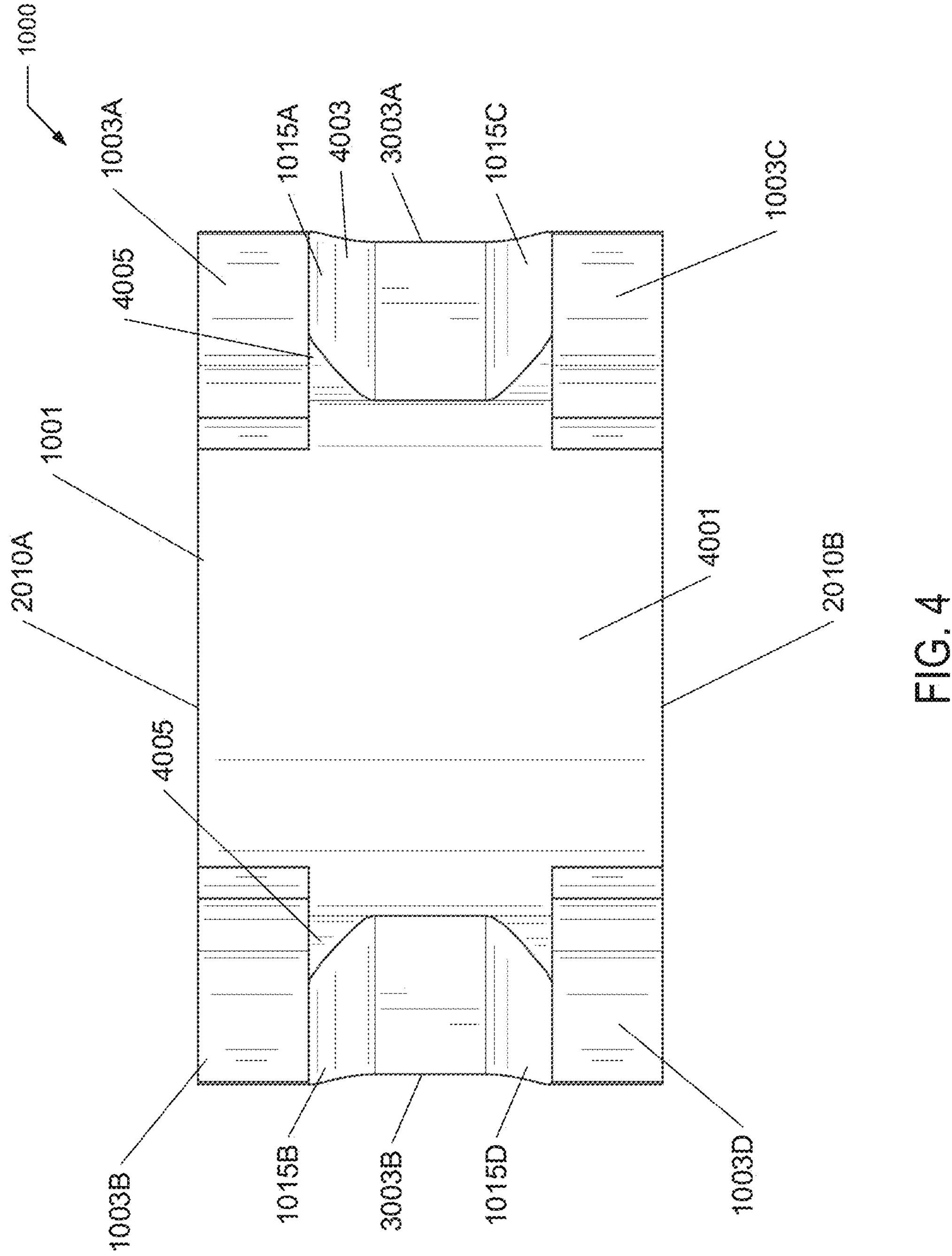
FIG. 4 shows a bottom view of an exemplary staple, according to one embodiment of the present disclosure.

FIG. 4 shows a bottom view of the staple 1000. In various embodiments, the bridge 1001 includes a bottom surface 4001. In at least one embodiment, the edges 1007A, 1007B and the edges 3003A, 3003B define the bottom surface 4001. In at least one embodiment, the bottom surface 4001 is curved and substantially non-breaking between the edges 2010A, 2010B. In some embodiments, the bottom surface 4001 is curved and substantially non-breaking between the edges 1007A, 1007B (see FIG. 1) and a top surface of the bridge 1001 transitions to the bottom surface 4001 at the edges 1007A, 1007B. In at least one embodiment, the non-breaking construction of the bottom surface 4001 advantageously distributes stress (e.g., and, thereby, strain) substantially equally throughout the bridge 1001. According to one embodiment, the substantially uniform strain behavior of the bridge 1001 causes the bridge 1001 to demonstrate a substantially constant moment of inertia.

In one or more embodiments, the staple 1000 includes shoulders 1015A-D that connect each leg 1003A-D to the bridge 1001. In at least one embodiment, each shoulder 1015A-D includes a first inner surface 4003 and a second inner surface 4005 that transition the corresponding leg 1003A-D to the bridge 1001. For example, the first inner surface 4003 transitions the bottom surface 4001 to an inner surface 1018 and/or an inner surface 1020 of each leg 1003A-D (e.g., inner surfaces 1018, 1020 shown in FIG. 1). In various embodiments, the first inner surface 4003 and second inner surface 4003 are continuously curved and non-breaking. According to one embodiment, the continuous curvature and non-breaking properties of the shoulders 1015A-D result in a redistribution of stress concentrations from the legs 1003A-D and shoulders 1015A-D throughout the bridge 1001.

Figure 5:
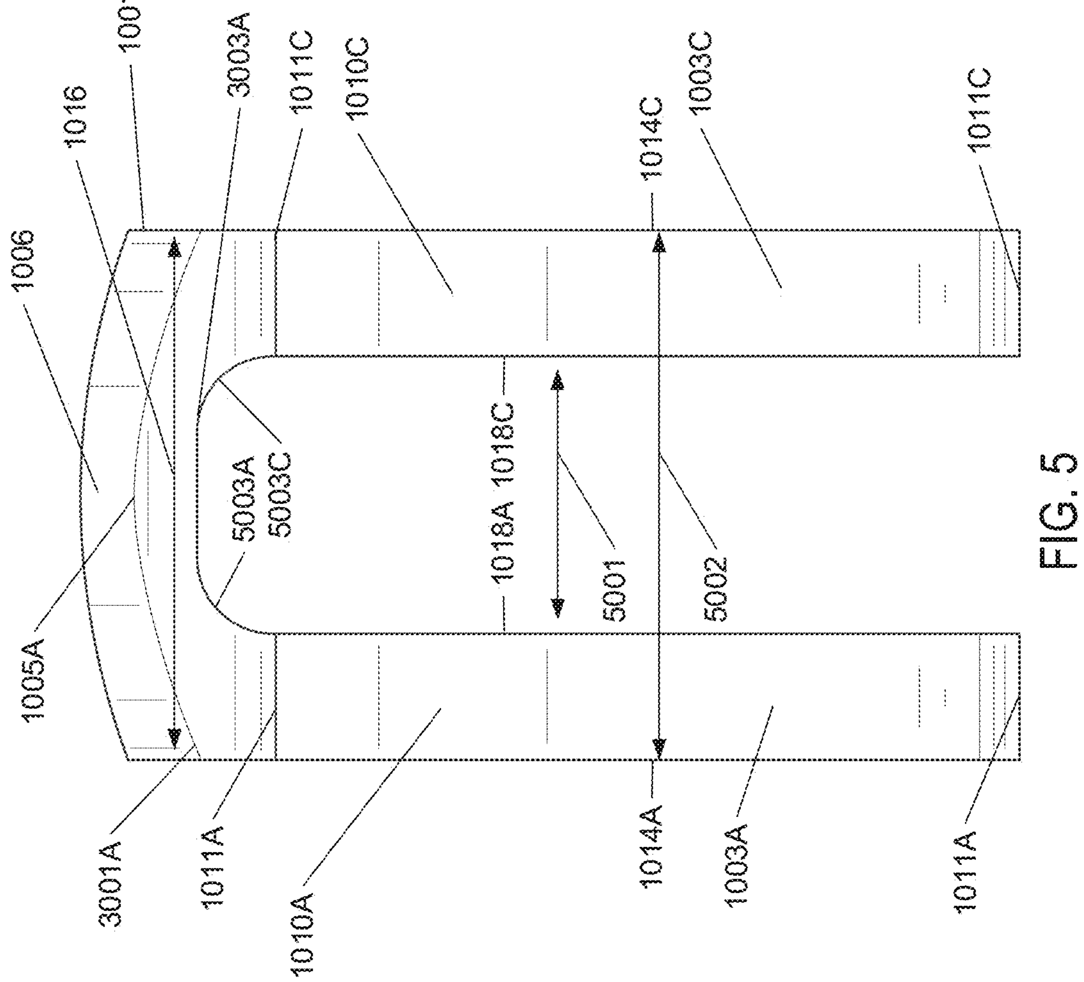
FIG. 5 shows a side view of an exemplary staple, according to one embodiment of the present disclosure.

FIG. 5 shows a side view of the staple 1000. In various embodiments, the legs 1003A, 1003C are separated by a distance 5001 between the leg inner surfaces 1018A, 1018C. In one or more embodiments, the distance 5001 measures at least about 2.0 mm, or about 2.0-8.0 mm, 2.0-3.0 mm, 3.0-4.0 mm, 4.0-5.0 mm, 5.5 mm, 5.0-6.0 mm, 6.0-7.0 mm, or 7.0-8.0 mm, or less than about 8.0 mm. In at least one embodiment, the distance 5001 varies along a length of the legs 1003A, 1003C. For example, the distance 5001 increases or decreases from the edge 3003A toward the ends 1011A, 1011C. In one or more embodiments, the distance 5001 is such that a distance 5002 between leg outer surfaces 1014A, 1014C is greater than the depth 1016 of the bridge 1001.

In one or more embodiments, the edge 3003A is continuously curved between the legs 1003A, 1003C. In at least one embodiment, the edge 3003A demonstrates a discontinuous curvature between the legs 1003A, 1003C. For example, the edge 3003A includes a first curve that connects to the leg 1003A (e.g., or a shoulder 1015A shown in FIG. 4) and transitions to a substantially horizontal central portion. In the same example, the substantially horizontal portion transitions to a second curve and the second curve connects to the leg 1003C. In various embodiments, the edge 3003A defines radii 5003A, 5003C for transition a depth of the legs 1003A, 1003C to a depth of the bridge 1001. In one or more embodiments, the radii 5003A, 5003C measure at least about 1.0 mm, or about 1.0-4.0 mm, 0.5-1.0 mm, 1.0-1.5 mm, 1.5-2.0 mm, 2.0-2.5 mm, 2.5 mm, 2.5-3.0 mm, 3.0-3.5 mm, or 3.5-4.0 mm, or less than about 4.0 mm. In some embodiments, the radius 5003A is greater than or less than radius 5003C.

FIG. 6 shows a cross-section 6000 of the staple 1000 (e.g., in particular, the bridge 1001 shown in FIG. 1). In one or more embodiments, the cross-section 6000 includes an edge 6001 between corners 6003A-B. In at least one embodiment, the cross-section 6000 includes an edge 6005 between corners 6003C-D. In one or more embodiments, the cross-section 6000 includes edges 6007A, 6007B that connect the edges 6001, 6005. In one or more embodiments, the edge 6001 is continuously curved between the corners 6003A-B and/or the edge 6005 is continuously curved between the corners 6003C-D. In at least one embodiment, the edge 6001 and/or edge 6005 is substantially horizontal. In some embodiments, the edge 6001 and edge 6005 are substantially parallel. In at least one embodiment, the edge 6001 and/or edge 6005 demonstrates a discontinuous curvature. For example, the edge 6001 includes a first curved shape toward the corner 6003A and a second curved shape toward the corner 6003B. In this example, the edge 6001 includes a substantially horizontal shape at a midpoint 6002, and the substantially horizontal shape transitions the first curved shape to the second curved shape.

In some embodiments, the cross-section 6000 is substantially uniform (e.g., in material density or other physical properties) along a thickness 6004 and/or along a depth 6006. In at least one embodiment, the cross-section 6000 demonstrates non-uniformity along the thickness 6004 and/or along the depth 6006. In various embodiments, the bridge 1001 (FIG. 1) demonstrates cross-section discontinuity. In other words, the cross-section 6000 and another cross-section of the bridge 1001 taken from a different section than that indicated by section line 2020 (FIG. 2) can be non-uniform. In one or more embodiments, the cross-section depth 6006 is greater than the cross-section thickness 6004, which may advantageously contribute to increased distribution of stress concentrations throughout the cross-section 6000 (e.g., and, thereby, throughout the bridge 1001).

Figure 7:
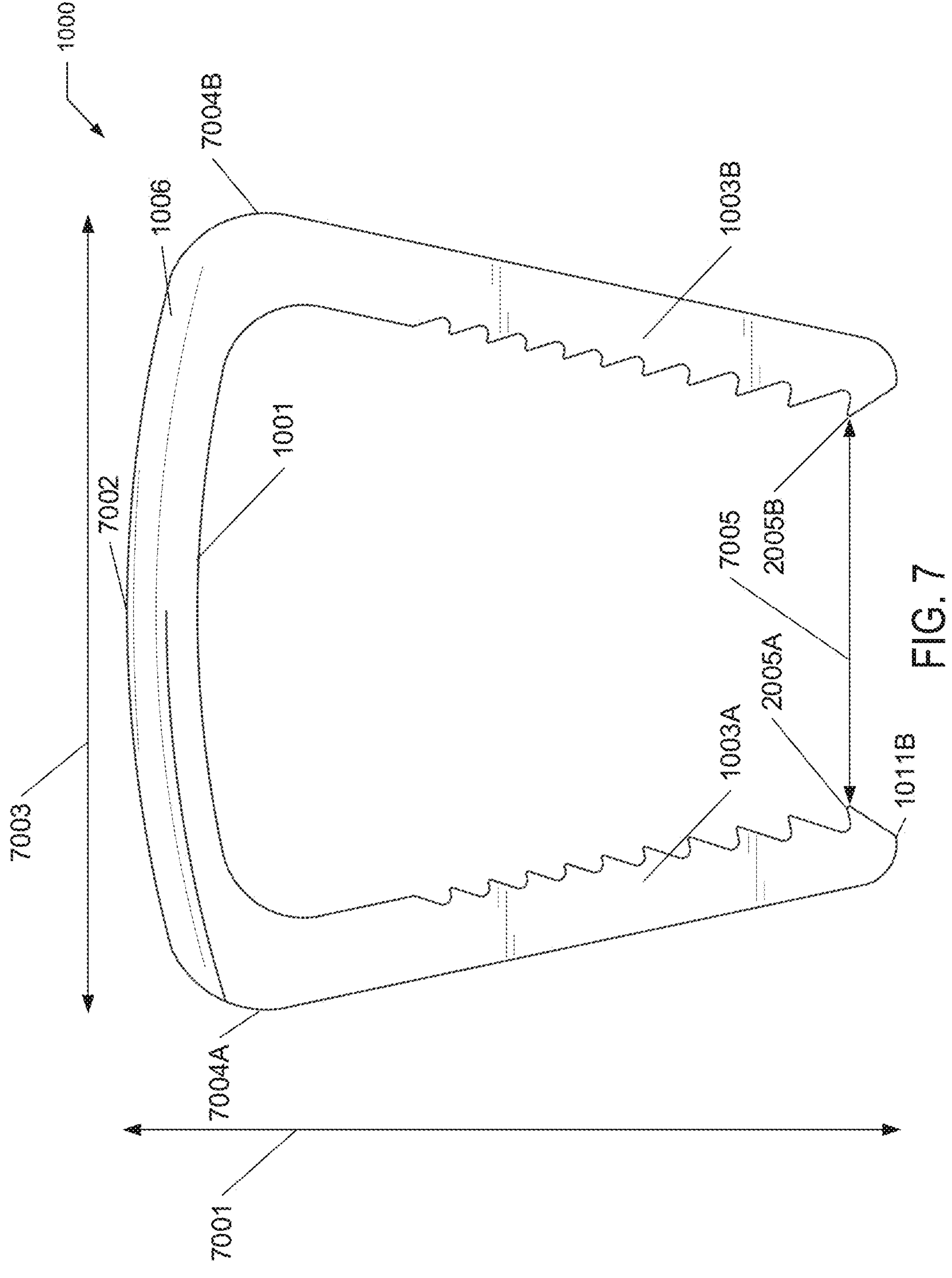
FIG. 7 shows a back view of an exemplary staple, according to one embodiment of the present disclosure.

FIG. 7 shows a back view of the staple 1000. In at least one embodiment, the staple 1000 includes a length 7001 between an apex 7002 of the bridge top surface 1006 and the end 1011B of the leg 1003A. In some embodiments, the apex 7002 may be positioned in a central region of the top surface 1006. In various embodiments, the length 7001 measures at least about 12.0 mm, or about 12.0-24.0 mm, 12.0-14.0 mm, 14.0-16.0 mm, 16.0-18.0 mm, 18.6 mm, 18.0-20.0 mm, 20.0-22.0 mm, or 22.0-24.0 mm, or less than about 24.0 mm. In one or more embodiments, the staple 1000 includes a width 7003 between opposing points 7004A, 7004B. In at least one embodiment, the width 7003 measures at least about 12.0 mm, or about 12.0-24.0 mm, 12.0-14.0 mm, 14.0-16.0 mm, 16.0-18.0 mm, 18.0-20.0 mm, 19.3 mm, 20.0-22.0 mm, or 22.0-24.0 mm, or less than about 24.0 mm.

In one or more embodiments, the staple 1000 includes a separation distance 7005 between a tooth 2005A of the leg 1003A and an opposing tooth 2005B of the leg 1003B. In at least one embodiment, the separation distance 7005 measures at least about 5.0 mm, or about 5.0-12.0 mm, 5.0-6.0 mm, 6.0-7.0 mm, 7.0-8.0 mm, 8.0-9.0 mm, 9.5 mm, 9.0-10.0 mm, 10.0-11.0 mm, or 11.0-12.0 mm, or less than about 12.0 mm.

Figure 8:
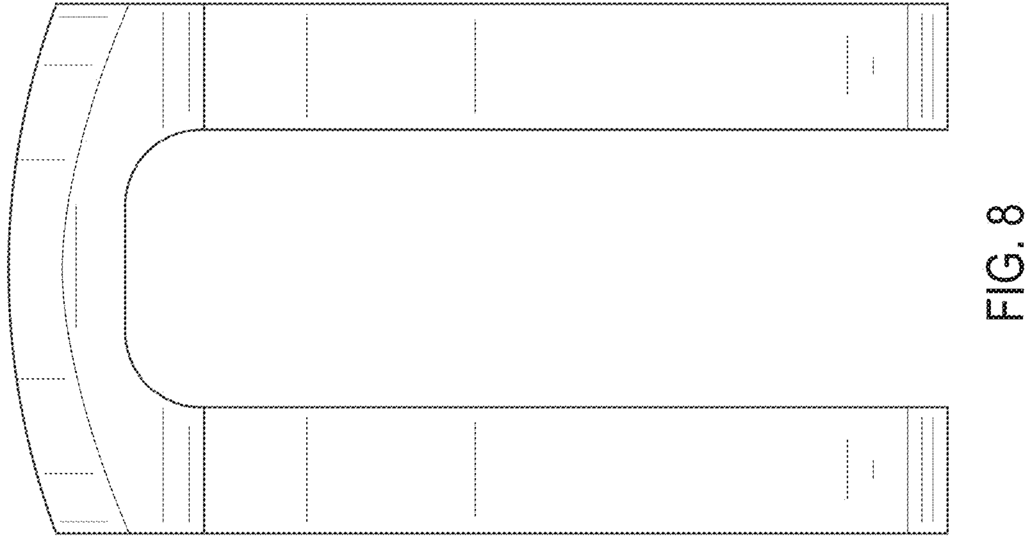
FIG. 8 shows a side view of an exemplary staple, according to one embodiment of the present disclosure.

FIG. 8 shows a side view of the staple 1000.

Figure 9:
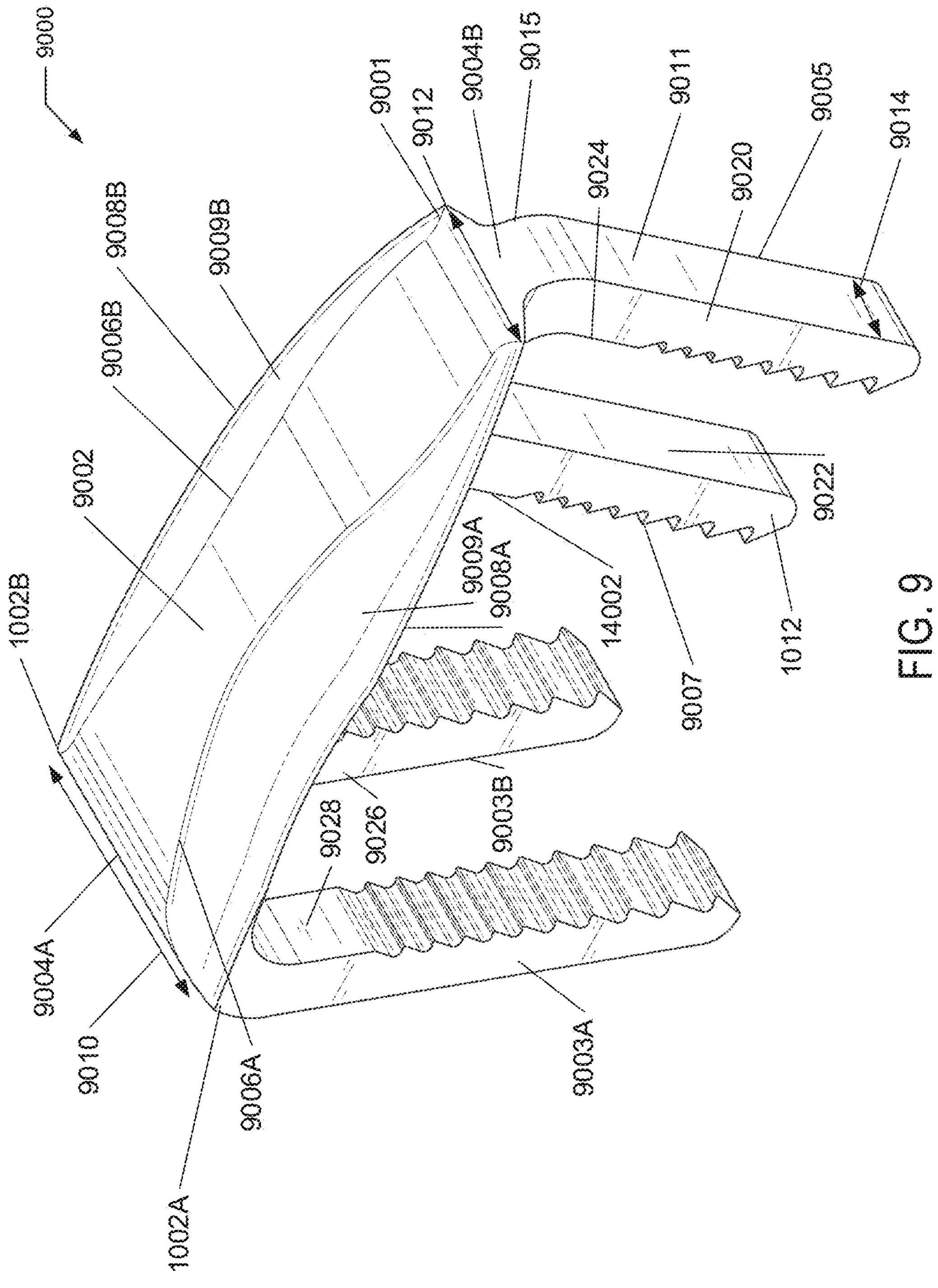
FIG. 9 shows a perspective view of an exemplary staple, according to one embodiment of the present disclosure.

FIG. 9 shows a perspective view of an exemplary staple 9000, according to one embodiment of the present disclosure. In various embodiments, the staple 9000 demonstrates properties substantially similar to the staple 1000. For example, a bridge 9001 of the staple 9000 demonstrates a substantially low profile construction and a constant moment inertia similar to the bridge 1001 of the staple 1000. In at least one embodiment, the staple 9000 is deformable (e.g., bendable) between a first and a second position and demonstrates stress concentration distribution throughout the bridge 9001 similar to that demonstrated by the bridge 1001 (FIG. 1).

In various embodiments, the staple 9000 includes a bridge 9001, legs 9003A-B, leg 9005, and leg 9007. The legs 9003A-B, leg 9005, and leg 9007 can be integrally formed with the bridge 9001. The legs 9003A-B, leg 9005, and leg 9007 can include properties and characteristics similar to those of legs 1003A-D of the staple 1000 (FIG. 1). According to one embodiment, the staple 9000 size (e.g., bridge 9001 length×leg 9003A-B, 9005, or 9007 length) may be greater than, less than or equal to about 18.0 mm×20.0 mm. According to one embodiment, the bridge 1001 includes opposing ends 9004A, 9004B. In at least one embodiment, the legs 9003A-B connect to the bridge 9001 toward the end 9004A and the leg 9005 connects to the bridge 9001 toward the end 9004B.

In various embodiments, the bridge 9001 includes a generally trapezoidal or rectangular shape. In one or more embodiments, the bridge 9001 tapers from a first depth 9010 to a second depth 9012 between the ends 9004A-B. According to one embodiment, the depth 9010 measures at least about 5.0 mm, or about 5.0-15.0 mm, 5.0-7.0 mm, 7.0-9.0 mm, 9.0-11.0 mm, 10.5 mm, 11.0-13.0 mm, or 13.0-15.0 mm, or less than about 15.0 mm. In one or more embodiments, the depth 9012 measures at least about 2.0 mm, or about 2.0-8.0 mm, 2.0-3.0 mm, 2.7 mm, 3.0-4.0 mm, 4.0-5.0 mm, 5.4 mm, 5.0-6.0 mm, 6.0-7.0 mm, or 7.0-8.0 mm, or less than about 8.0 mm.

In at least one embodiment, the bridge 9001 includes substantially curved or radial transitions between the legs 9003A-B, 9005, shoulders 12001A-B (FIG. 12), and a top surface 9002 and/or bottom surface 1201 (FIG. 12) of the bridge 9001. In various embodiments, the legs 9003A-B are substantially parallel and the legs 9005, 9007 are substantially parallel. In one or more embodiments, the parallel characteristic of legs 9003A-B and of legs 9005, 9007 is maintained regardless of a deformation state of the staple 1000. For example, the 9005, 9007 remain substantially parallel as the staple 9000 transitions to a deformed state (e.g., via bending along the bridge 9001). In at least one embodiment, the legs 9003A-B connect to the bridge 9001 at corners 1002A, 1002B (see also FIG. 1 description). In at least one embodiment, each corner 1002A, 1002B includes the radius 1004 (see also FIG. 1 description).

In one or more embodiments, the bridge 9001 demonstrates a constant moment of inertia between the first end 1005A and the second end 1005B. According to one embodiment, the substantially constant moment of inertia provides advantages similar to those provided by the substantially constant moment of inertia of the bridge 1001 (FIG. 1). In various embodiments, the bridge 9001 is curved between the ends 9004A-B. In at least one embodiment, the bridge 9001 includes a substantially smooth top surface 9002 between the ends 9004A-B, and between a first edge 9006A and a second edge 9006B. In one or more embodiments, the top surface 9002 is substantially smooth and non-breaking. According to one embodiment, the non-breaking quality of the top surface 9002 distributes stress substantially equally throughout the bridge 9001, thereby reducing a prevalence of stress concentrations (e.g., as compared to previous staples that demonstrate discontinuous bridge surfaces) and improving durability of the staple 9000.

In at least one embodiment, the bridge 9001 includes side surfaces 9009A-B, and the edges 9006A-B transition the top surface 9002 to each corresponding side surface 9009A-B. According to one embodiment, transitions between the top surface 9002 and side surfaces 9009A-B are substantially smooth and demonstrate non-breaking curvature. In various embodiments, the bridge 9001 includes edges 9008A, 9008B that transition the side surfaces 9009A-B to a bottom surface 1201 (FIG. 12) of the bridge 9001. According to one embodiment, the side surfaces 9009A-B demonstrate a convex or a concave curvature between corresponding edges 9006A-B and edges 9008A-B.

Figure 14:
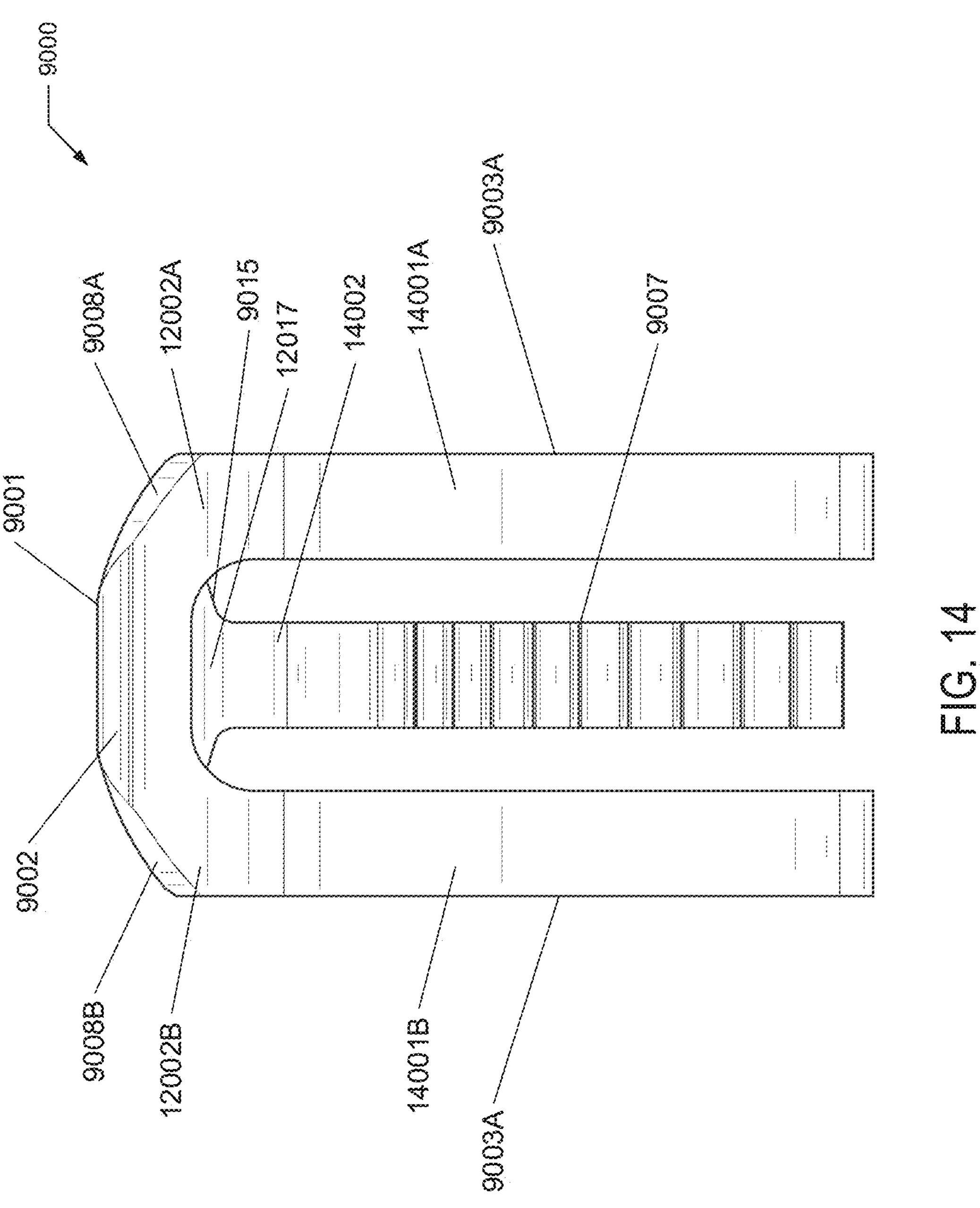
FIG. 14 shows a cross-section of an exemplary staple, according to one embodiment of the present disclosure.

In at least one embodiment, at the end 9004A the top surface 9002 transitions to shoulders 1202A-B (FIG. 12) and/or to an outer surface 14001 of each leg 9003A-B (see FIG. 14). In one or more embodiments, at the end 9004B the top surface 9002 transitions to a shoulder 9015 and/or to an outer surface 9011 of the leg 9005. In various embodiments, the legs 9003A-B each include an inner surface 9026 and an inner surface 9028. In one or more embodiments, the inner surfaces 9026, 9028 of each leg 9003A-B transition to a shoulder 1204A or shoulder 1204B (see FIG. 12).

In at least one embodiment, the shoulder 9015 transitions the bridge depth 9012 to a depth 9014 of the leg 9005. In various embodiments, the legs 9003A-B, leg 9005, and leg 9007 each demonstrate the depth 9014. In some embodiments, one or more of the legs 9003A-B, leg 9005, and leg 9007 demonstrate differing depths (for example, the depth of legs 9003A-B can be greater than the depth of legs 9005, 9007. The depth 9014 can be substantially similar to the depth 1017 (FIG. 1).

Figure 12:
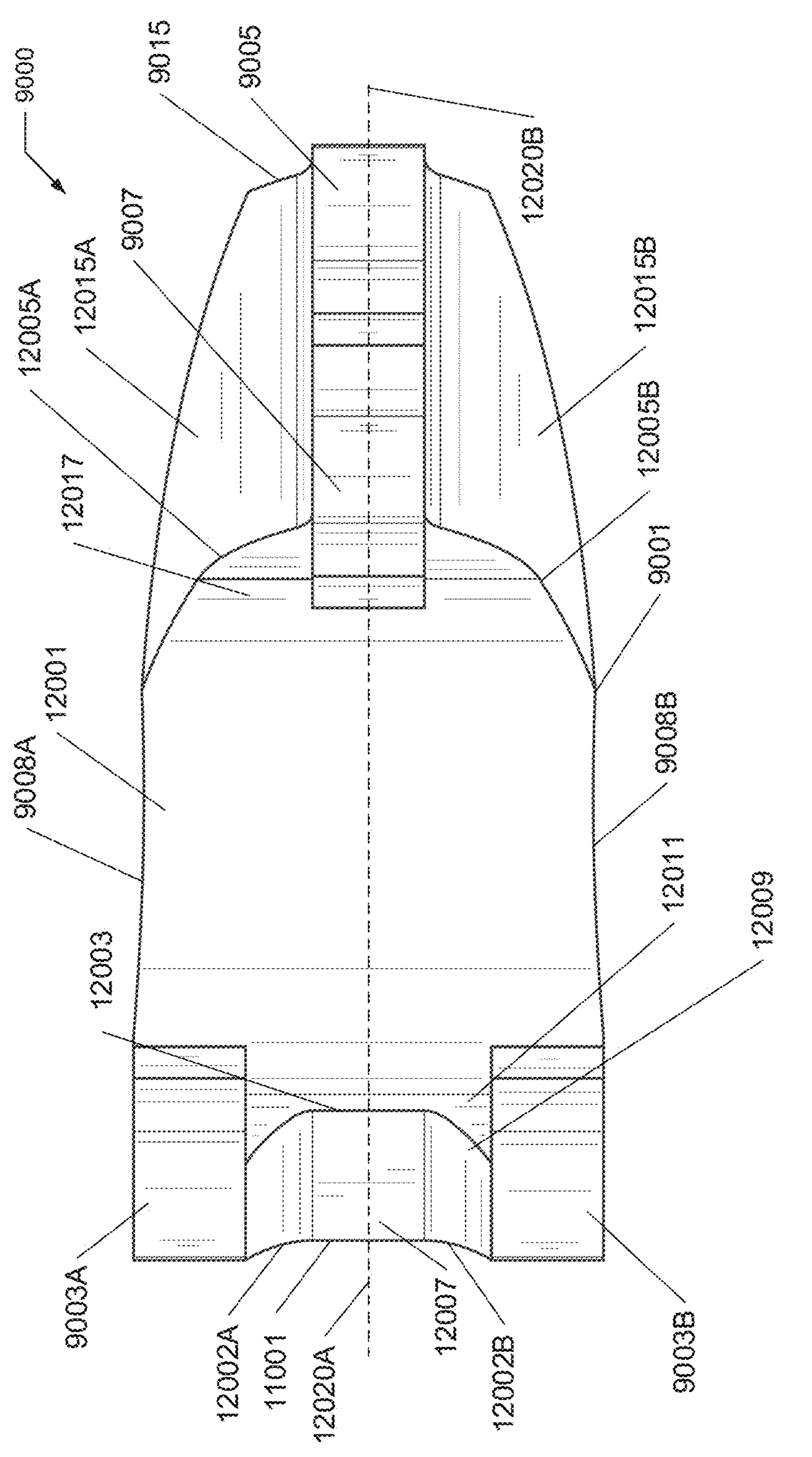
FIG. 12 shows a bottom view of an exemplary staple, according to one embodiment of the present disclosure.
Figure 16:
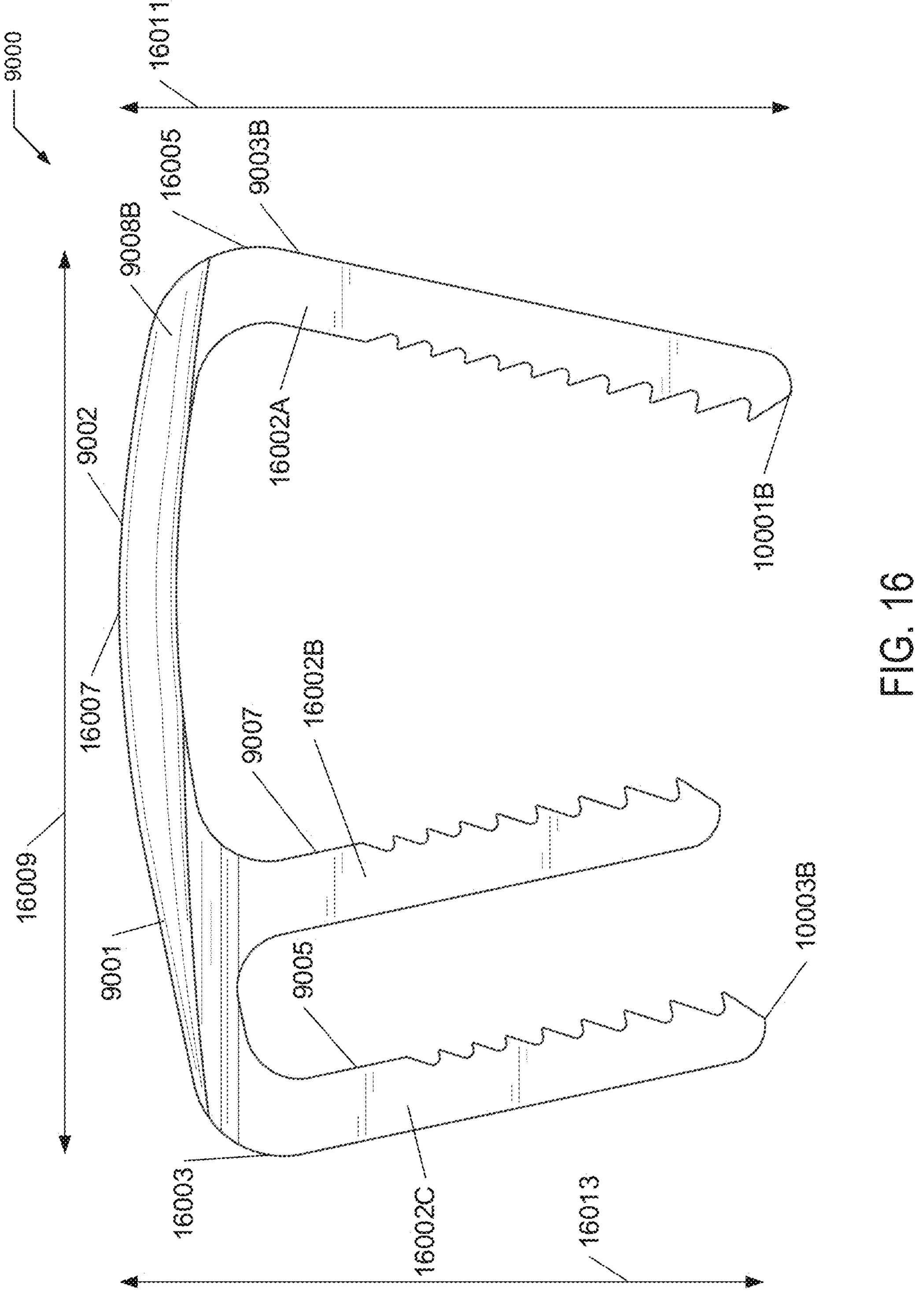
FIG. 16 shows a side view of an exemplary staple, according to one embodiment of the present disclosure.

In at least one embodiment, the legs 9003A-B, 9005, 9007 each include a side surface 9020 (e.g., and include a second, opposing side surface shown in FIG. 16). In some embodiments, the side surfaces 9020 of legs 9005, 9007 are coplanar. In one or more embodiments, the side surfaces 9020 of legs 9003A-B are parallel. In various embodiments, the leg 9007 includes an inner surface 9022 and an inner surface 14002 (see FIG. 14) opposite the inner surface 9022. According to one embodiment, the leg 9005 includes an inner surface 9024 opposite the outer surface 9011. In at least one embodiment, the side surfaces 9020 of the legs 9005, 9007, the inner surface 9024 of the leg 9005, and the inner surfaces 9022, 14002 of the leg 9007 connect to a shoulder 9015 (e.g., as shown in FIG. 12).

In at least one embodiment, portions of the bridge 9001 extend past the ends 9004A-B. In various embodiments, the extending portions include a top surface substantially coplanar with the top surface 9002 of the bridge 9001 and a bottom surface substantially coplanar or superior to a bottom surface 12003 (FIG. 12) of the bridge 9001. In one or more embodiments, the extending portions are for increasing ease of deforming the staple 9000 between a first and a second position described herein by providing surfaces to which deforming forces are applied. According to one embodiment, the coplanar or superior position provides sufficient space for insertion of tools between the extending portions (and other features, as suitable) and a target region, such as a bone surface, thereby allowing for manipulation of the extending portions.

In various embodiments, the legs 9003A-B, 9005, and 9007 each include a tip 1012 (see FIG. 1).

In various embodiments, a shoulder 1015 connects each leg 1003A-D to the bridge 1001. In at least one embodiment, the shoulder 1015 transitions a depth 1016 of the bridge 1001 to a depth 1017 of each leg 1003A-D. In one or more embodiments, the depth 1016 measures at least about 8.0 mm, or about 8.0-12.0 mm, 8.0-8.5 mm, 8.5-9.0 mm, 9.0-9.5 mm, 9.5-10.0 mm, 10.0-10.5 mm, 10.5 mm, 10.5-11.0 mm, 11.0-11.5 mm, or 11.5-12.0 mm, or less than about 12.0 mm. In some embodiments, the depth 1016 tapers from a first magnitude at the first end 1005A and the second end 1005B to a second magnitude toward a central bridge portion spanning a length of the bridge 1001 therebetween. In various embodiments, the shoulder 1015 transitions a depth 1016 of the bridge 1001 from a first magnitude to a second magnitude.

In at least one embodiment, the depth 1017 measures at least about 1.0 mm, or about 1.0-4.0 mm, 0.5-1.0 mm, 1.0-1.5 mm, 1.5-2.0 mm, 2.0-2.5 mm, 2.5 mm, 2.5-3.0 mm, 3.0-3.5 mm, or 3.5-4.0 mm, or less than about 4.0 mm. In one or more embodiments, the shoulder 1015 defines a radius 1017 for transitioning the bridge 1001 to each leg 1003A-D. In various embodiments, the radius 1017 measures at least about 1.0 mm, or about 1.0-4.0 mm, 0.5-1.0 mm, 1.0-1.5 mm, 1.5 mm, 1.5-2.0 mm, 2.0-2.5 mm, 2.5 mm, 2.5-3.0 mm, 3.0-3.5 mm, or 3.5-4.0 mm, or less than about 4.0 mm.

According to one embodiment, the shoulder 9015 and shoulders 1202A-B (FIG. 12) includes properties and characteristics similar to shoulder 1015 (FIG. 1). For example, the shoulder 9015 and shoulders 1202A-B advantageously transfer stress concentrations away from connections between the bridge 9001 and legs 9003A-B, 9005, 9007 and into the bridge 9001, thereby improving staple durability.

Figure 10:
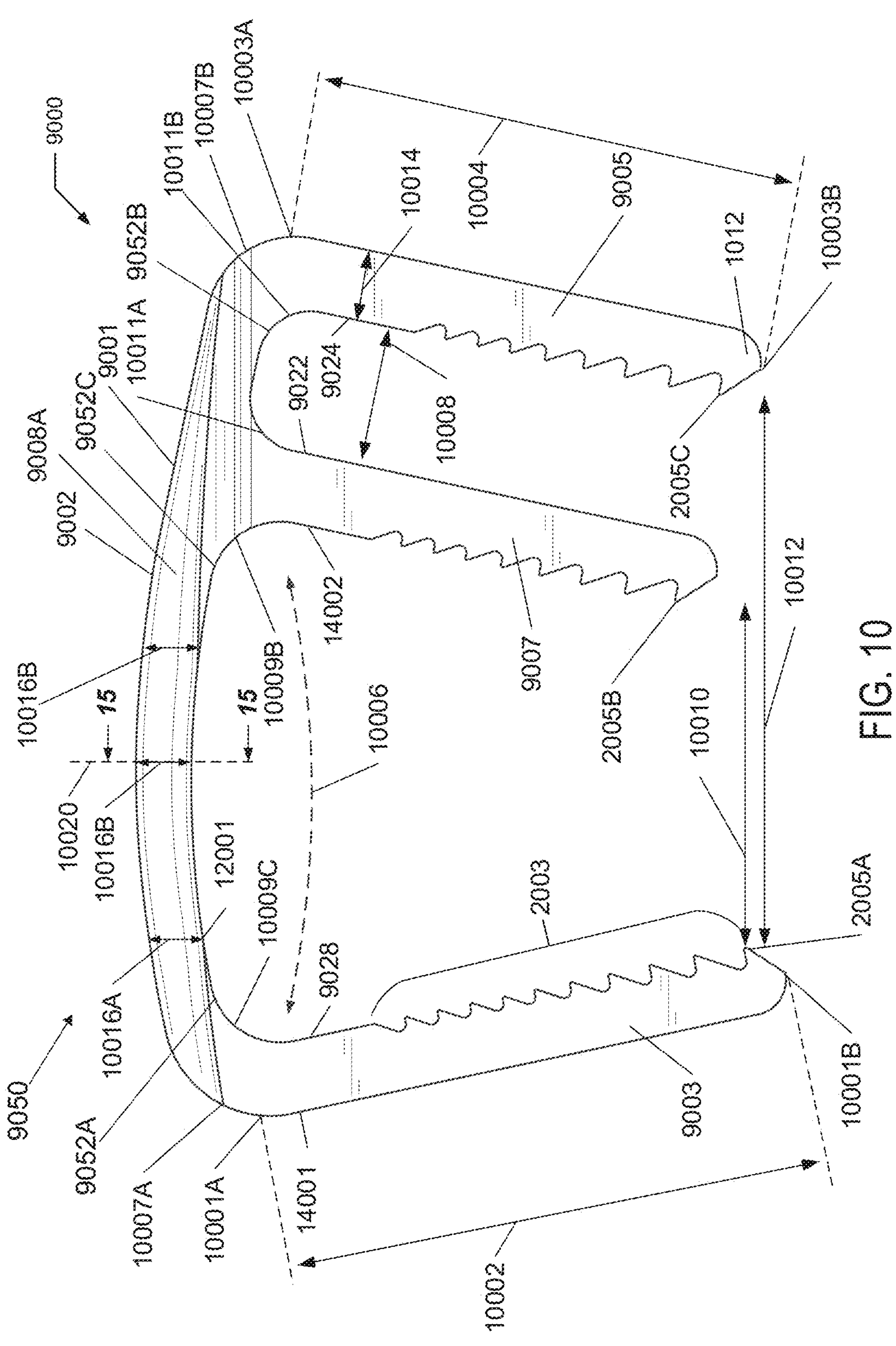
FIG. 10 shows a front view of an exemplary staple, according to one embodiment of the present disclosure.

FIG. 10 shows a front view of an exemplary staple 9000, according to one embodiment of the present disclosure. In various embodiments, the legs 9003, 9005, and 9007 each include a tip 1012 (see also FIG. 1). In one or more embodiments, the legs 9003, 9005, and 9007 include one or more teeth sections 2003 (see FIG. 2).

In at least one embodiment, the leg 9003 (e.g., corresponding to legs 9003A-B shown in FIG. 9) includes a first end 10001A and a second end 10001B. In various embodiments, the leg 9003 includes a length 10002 between the ends 10001A-B. According to one embodiment, the length 10002 measures at least about 12.0 mm, or about 12.0-24.0 mm, 12.0-14.0 mm, 14.0-16.0 mm, 16.0 mm, 16.0-18.0 mm, 18.0-20.0 mm, 20.0-22.0 mm, or 22.0-24.0 mm, or less than about 24.0 mm. In some embodiments, the leg 9003A (FIG. 9) demonstrates a greater or lesser length as compared to a length of the leg 9003B (FIG. 9). In one or more embodiments, the legs 9005, 9007 each include a first end 10003A and a second end 10003B. In at least one embodiment, the legs 9005, 9007 each include a length 10004 between the ends 10003A-B. In various embodiments, the length 10004 measures at least about 12.0 mm, or about 12.0-24.0 mm, 12.0-14.0 mm, 14.0 mm, 14.0-16.0 mm, 16.0-18.0 mm, 18.0-20.0 mm, 20.0-22.0 mm, or 22.0-24.0 mm, or less than about 24.0 mm. In some embodiments, the leg 9005 demonstrates a greater or lesser length as compared to a length of the leg 9007. In one or more embodiments, the length 10002 and the length 10004 are substantially equal.

In various embodiments, the staple 9000 includes a curvature 10006 between the leg 9003 and the leg 9007. In one or more embodiments, the curvature 10006 measures at least about 5 degrees, or about 5-45 degrees, 5-10 degrees, 10-15 degrees, 16 degrees, 15-degrees, 20-25 degrees, 24 degrees, 25-30 degrees, 30-35 degrees, 35-40 degrees, or 40-45 degrees, or less than about 45 degrees. According to one embodiment, the curvature 10006 decreases as the staple 9000 deforms from a first state (e.g., as shown in FIGS.

9-16) to a second state (not shown). In one example, as the staple 9000 transitions to a deformed state, the curvature 10006 decreases from about 24 degrees to 0 degrees. In at least one embodiment, the legs 9005, 9007 remain substantially parallel regardless of a deformation state of the staple 9000.

In at least one embodiment, the bridge 1001 includes radii 10007A-B for transitioning the top surface 9002 (e.g., and/or side surfaces 9008A-B) of the bridge 9001 to the outer surface 14001 of the leg 9003 and to the outer surface 9011 of the leg 9005. In various embodiments, the radii 10007A-B measure at least about 0.5 mm, about 0.5-5.0 mm, 0.5-1.0 mm, 1.0-2.0 mm, 2.5 mm, 2.0-3.0 mm, 3.0-4.0 mm, or 4.0-5.0 mm, or less than about 5.0 mm. In some embodiments, the radius 10007A is greater or less than the radius 10007B. In one or more embodiments, the bridge 1001 includes radii 10009A-B for transitioning the bottom surface 12001 to the inner surface 9028 of the leg 9003 and to the inner surface 14002 of the leg 9007. According to one embodiment, the radii 10009A-B measure at least about 0.5 mm, or about 0.5-5.0 mm, 0.5-1.0 mm, 1.0-2.0 mm, 2.0 mm, 2.0-3.0 mm, 3.0-4.0 mm, or 4.0-5.0 mm, or less than about 5.0 mm. In some embodiments, the radius 10009A is greater or less than the radius 10009B. In one or more embodiments, the bridge 1001 includes radii 10011A-B for transitioning the bottom surface 12001 to the inner surface 9022 of the leg 9007 and to the inner surface 9024 of the leg 9005. In at least one embodiment, the radii 10011A-B measure at least about 0.5 mm, or about 0.5-5.0 mm, 0.5-1.0 mm, 1.0-2.0 mm, 2.0 mm, 2.0-3.0 mm, 3.0-4.0 mm, or 4.0-5.0 mm, or less than about 5.0 mm. In some embodiments, the radius 10011A is greater or less than the radius 10011B. In at least one embodiment, the radii 10007A-B define radial points of the bridge 9001, and the bridge 9001 demonstrate a substantially continuous cross-section in a bridge portion bounded by the radial points.

According to some embodiments, the staple 9000 includes at least one transition area 9050 defined by an area between the bridge 9001 and an outer surface of each leg 9003A-B, 9005, 9007. In one embodiment, the at least one transition area 9050 may include a portion of the top surface 9002 of the bridge 9001. In other embodiments, the at least one transition area 9050 may include a downwardly sloping portion of the bridge 9001. In some embodiments, the bridge 9001 is defined between at least a first radial tangent 9052A and a second radial tangent 9052B such that the at least one transition area 9050 is an area of the bridge 9001 disposed between the first or a second radial tangent 9052A-B and an end 9004A-B (with the bridge 9001 between first and second radial tangents 9052A-B). In other embodiments, the bridge 9001 is at least partially defined between at least a first radial tangent 9052A and a third radial tangent 9052C such that the at least one transition area 9050 includes an area of the bridge 9001 disposed about a third radial tangent 9052C and end 9004B (with at least a portion of the bridge 9001 between first and third radial tangents 9052A, C). In embodiments, the bridge 9001 is at least partially defined between at least a second radial tangent 9052B and a third radial tangent 9052C such that the at least one transition area 9050 includes an area of the bridge 9001 disposed about a third radial tangent 9052C and end 9004A (with at least a portion of the bridge 9001 between second and third radial tangents 9052B, C).

In various embodiments, the inner surface 9024 of the leg 9005 and the inner surface 9022 of the leg 9007 are separated by a distance 10008. According to one embodiment, the distance 10008 measures at least about 1.0 mm, or about 1.0-7.0 mm, 1.0-2.0 mm, 2.0-3.0 mm, 3.0-4.0 mm, 4.0 mm, 4.0-5.0 mm, or 6.0-7.0 mm, or less than about 7.0 mm. In at least one embodiment, the leg 9003 is separated from the leg 9007 by a distance 10010 as measured between a tooth 2005A of the leg 9003 and a tooth 2005B of the leg 9007. In one or more embodiments, the distance 10010 measures at least about 6.0 mm, about 6.0-12.0 mm, 6.0-7.0 mm, 7.0-8.0 mm, 8.0-9.0 mm, 9.8 mm, 9.0-10.0 mm, 10.0-11.0 mm, or 11.0-12.0 mm, or less than about 12.0 mm. In various embodiments, the leg 9003 is separated from the leg 9005 by a distance 10012 as measured between the tooth 2005A and a tooth 2005C of the leg 9005. According to one embodiment, the distance 10012 measures at least about 12.0 mm, or about 12.0-18.0 mm, 12.0-13.0 mm, 13.0-14.0 mm, 14.0-15.0 mm, 15.7 mm, 15.0-16.0 mm, 16.0-17.0 mm, or 17.0-18.0 mm, or less than about 18.0 mm. In various embodiments, the legs 9003, 9005, and 9007 includes a thickness 10014. According to one embodiment, the thickness 10014 measures at least about 0.5 mm, or about 0.5-5.0 mm, 0.5-1.0 mm, 1.0-2.0 mm, 2.0-3.0 mm, 3.0-4.0 mm, 4.0 mm, or 4.0-5.0 mm, or less than about 5.0 mm. In some embodiments, one or more of the legs 9003, 9005, and 9007 demonstrate differing thickness. In at least one embodiment, the thickness 10014 varies between the ends 10001A-B of the leg 9003 and/or between the ends 10003A-B of the leg 9005 and/or leg 9007.

In one or more embodiments, the bridge 9001 includes a thickness 10016A-C. In various embodiments, the thickness 10016A-C measures at least about 0.5 mm, or about 0.5-4.0 mm, 0.5-1.0 mm, 1.0-1.5 mm, 1.22 mm, 1.25 mm, 1.32 mm, 1.36 mm, 1.42 mm, 1.47 mm, 1.5 mm, 1.52 mm, 1.57 mm, 1.5-2.0 mm, 1.67 mm, 2.0 mm, 2.0-2.5 mm, 2.5-3.0 mm, 3.0-3.5 mm, or 3.5-4.0 mm, or less than about 4.0 mm. In at least one embodiment, the thickness 10016A-C varies along the bridge 9001 (e.g., a midpoint, transitions to the legs 9003A-B, 9005, 9007, etc.). In one example, the thickness 10016A measures about 1.25 mm, the thickness 10016B measures about 1.36 mm, and the thickness 10016C measures about 1.52 mm. In another example, the thickness 10016A measures about 1.22 mm, the thickness 10016B measures about 1.32 mm, and the thickness 10016C measures about 1.52 mm. In another example, the thickness 10016A measures about 1.42 mm, the thickness 10016B measures about 1.47 mm, and the thickness 10016C measures about 1.57 mm. In another example, the thickness 10016A measures about 1.52 mm, the thickness 10016B measures about 1.57 mm, and the thickness 10016C measures about 1.67 mm.

Figure 15:
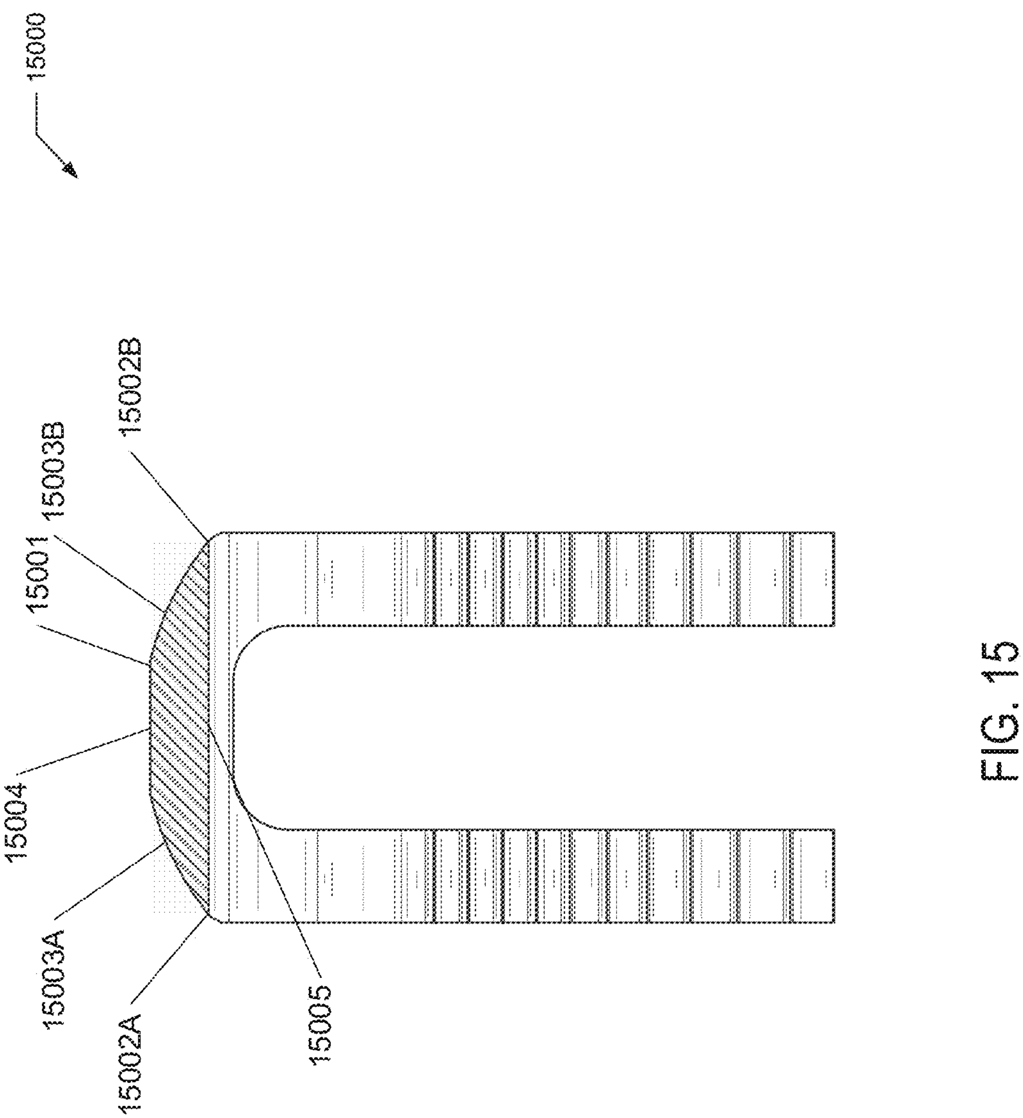
FIG. 15 shows a back view of an exemplary staple, according to one embodiment of the present disclosure.

According to one embodiment, section line 2020 defines a cross-section 15000 shown in FIG. 15.

Figure 11:
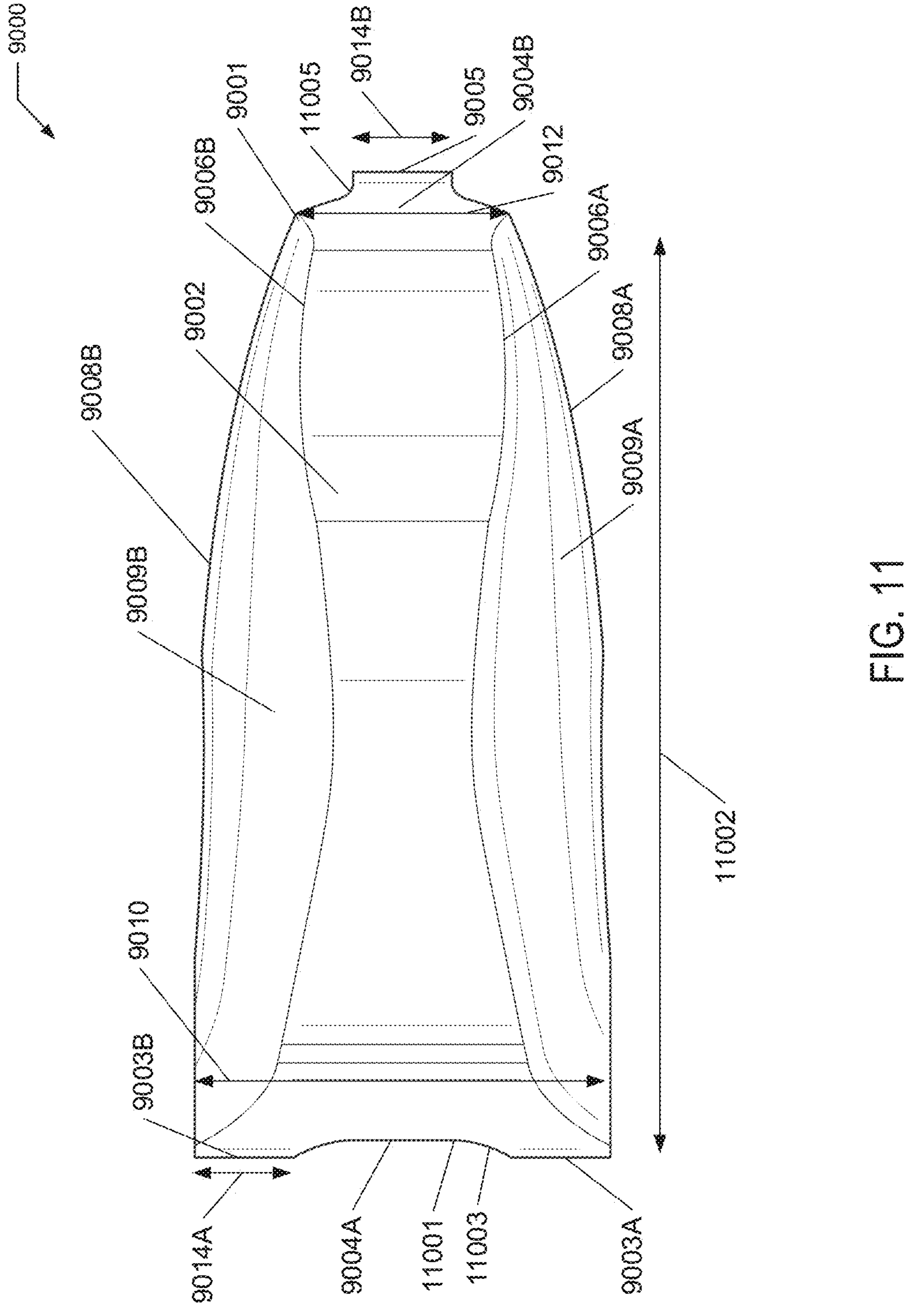
FIG. 11 shows a top view of an exemplary staple, according to one embodiment of the present disclosure.

FIG. 11 shows a top view of an exemplary staple 9000, according to one embodiment of the present disclosure. In one or more embodiments, the bridge 9001 includes an edge 11001 that transitions the bridge top surface 9002 to the legs 9003A-B (e.g., or to shoulders 12002A-B shown in FIG. 12). In at least one embodiment, the edge 11001 defines the bridge end 9004A. According to one embodiment, the edge 11001 demonstrates a continuous curvature between the legs 9003A-B (e.g., or shoulders 12002A-B). In some embodiments, the edge 11001 demonstrates a discontinuous curvature, such as, for example, a central horizontal region bounded by curved regions of opposing concavity. In one or more embodiments, the edge 11001 defines a radius 11003 for transitioning the top surface 9002 (e.g., and/or bridge bottom surface 12001 shown in FIG. 12) to the legs 9003A-B. In at least one embodiment, the radius 11003 measures at least about 0.5 mm, or about 0.5-3.0 mm, 0.5-1.0 mm, 1.0-1.5 mm, 1.5 mm, 1.5-2.0 mm, 2.0 mm, 2.0-2.5 mm, or 2.5-3.0 mm, or less than about 3.0 mm. According to one embodiment, the radius 11003 between each leg 9003A-B and the top surface 9002 transitions the bridge depth 9010 to the leg depth 9014A of each leg 9003A-B.

In various embodiments, the bridge 9001 includes a radius 11005 for transitioning the bridge depth 9012 to the leg depth 9014B. In at least one embodiment, the radius 11005 measures at least about 0.1 mm, or about 0.1-3.0 mm, 0.1-0.5 mm, 0.5 mm, 0.5-1.0 mm, 1.0-1.5 mm, 1.5-2.0 mm, 2.0-2.5 mm, or 2.5-3.0 mm, or less than about 3.0 mm.

FIG. 12 shows a bottom view of an exemplary staple 9000, according to one embodiment of the present disclosure. In various embodiments, the bridge 9001 includes a bottom surface 12001. In at least one embodiment, the bottom surface 12001 is bounded by edges 12003, 12005A-B, and edges 9008A-B. In some embodiments, the bottom surface 12001 extends to the edge 11001. In at least one embodiment, the bridge 9001 includes a bottom surface 12007 between the edge 11001 and the bottom surface 12001. According to one embodiment, the bottom surface 12001 can demonstrate continuous curvature between the edges 9008A-B and between the edges 12003, 12005A-B. In one or more embodiments, the edge 12003 demonstrates non-breaking curvature between the legs 9003A-B.

In one or more embodiments, the staple 9000 includes shoulders 12002A-B. In at least one embodiment, the shoulders 12002A-B connect the legs 9003A-B to the bridge 9001. In various embodiments, the shoulders 12002A-B each include an inner surface 12009 for transitioning the bottom surface 12007 (e.g., or bottom surface 12001) to the inner surfaces 9026 (FIG. 9) of corresponding legs 9003A-B. In at least one embodiment, the shoulders 12002A-B each include an inner surface 12011 for transitioning the bottom surface 12001 to the inner surfaces 9028 (FIG. 9) of corresponding legs 9003A-B. In one or more embodiments, the inner surface 12009 and 12011 demonstrate non-breaking curvature between the bottom surfaces 12002, 12001 and corresponding surfaces of the legs 9003A-B and the bridge 9001.

In various embodiments, the shoulder 9015 includes side surfaces 12015A, 12015B. In at least one embodiment, the edges 9008A, 12005A define the side surface 12015A, and the edges 9008B, 12005B define the side surface 12015B. In one or more embodiments, the side surfaces 12015A-B transition bridge side surfaces 9009A-B to the side surfaces 9020 (FIG. 9) and inner surfaces 9022, 9024 (FIG. 9), 14002 (FIG. 14) of the legs 9005, 9007. According to one embodiment, the side surfaces 9009A-B demonstrate non-breaking curvature between the edges 9008A-B and corresponding side surfaces of the legs 9005, 9007.

In various embodiments, the shoulder 9015 includes a side surface 12017 between the bottom surface 12001 and edges 12005A-B. According to one embodiment, the side surface 12017 transitions the bottom surface 12001 to the inner surface 14002 (FIG. 14) of the leg 9007. In one or more embodiments, the side surface 12017 demonstrates non-breaking curvature between the bottom surface 12001 and the leg 9007.

According to one embodiment, one or more of the leg 9005, leg 9007, and shoulder 9015 are centrally located along a central axis 12020A-B that symmetrically bisects the staple 9000. In various embodiments, the legs 9003A-B are symmetric about the central axis 12020A-B.

Figure 13:
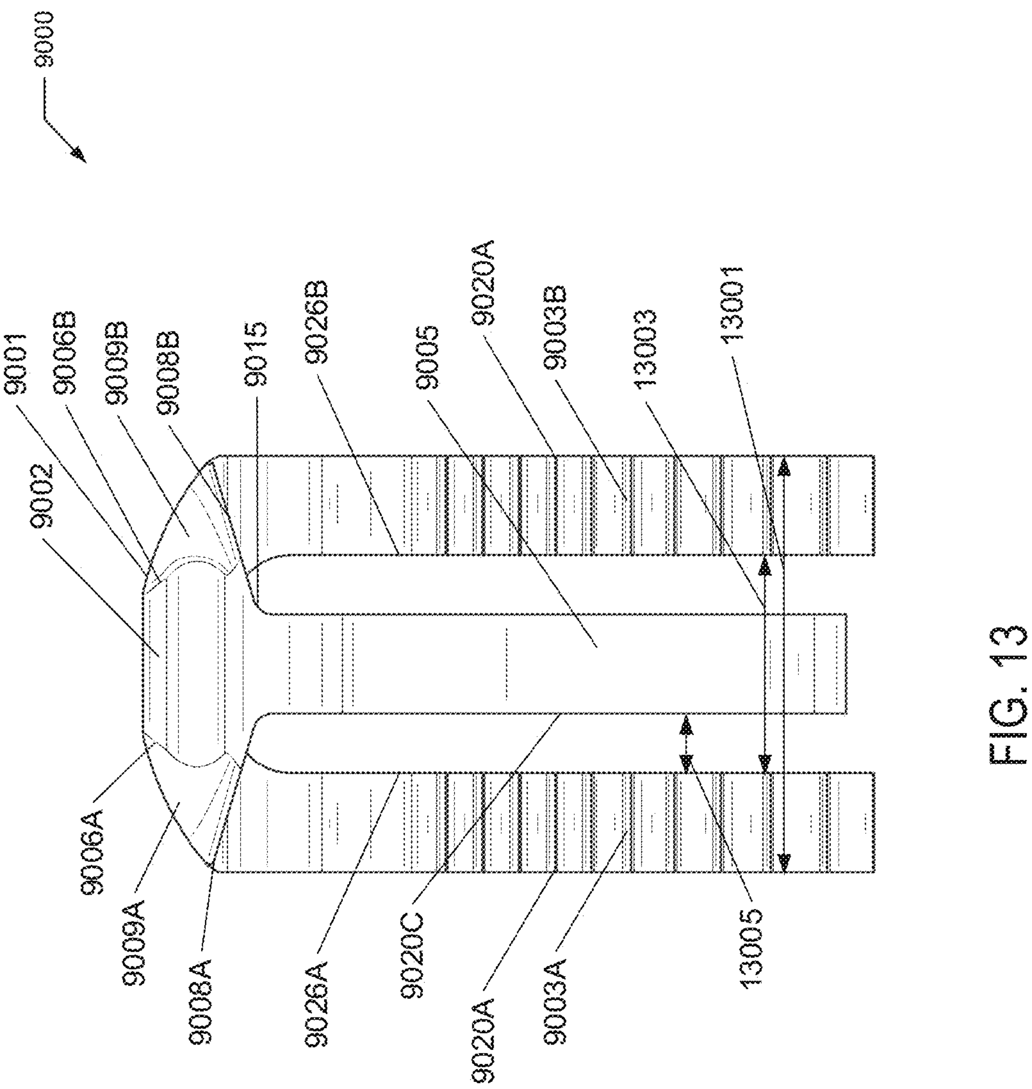
FIG. 13 shows a side view of an exemplary staple, according to one embodiment of the present disclosure.

FIG. 13 shows a side view of an exemplary staple 9000, according to one embodiment of the present disclosure. In various embodiments, a distance 13001 separates the side surface 9020A of the leg 9003A from the side surface 9020B of the side surface 9003B. In at least one embodiment, the distance 13001 measures about depth 1016 measures at least about 8.0 mm, or about 8.0-12.0 mm, 8.0-8.5 mm, 8.5-9.0 mm, 9.0-9.5 mm, 9.5-10.0 mm, 10.0-10.5 mm, 10.5 mm, 10.5-11.0 mm, 11.0-11.5 mm, or 11.5-12.0 mm, or less than about 12.0 mm. In some embodiments, the distance 13001 is greater or less than the depth 9010 (FIG. 9). In one or more embodiments, a distance 13003 separates the side surface 9026A of the leg 9003A from the side surface 9026B of the leg 9003B. In various embodiments, the distance 13003 measures at least about 2.0 mm, or about 2.0-9.0 mm, 2.0-3.0 mm, 3.0-4.0 mm, 4.0-5.0 mm, 5.0-6.0 mm, 5.5 mm, 6.0-7.0 mm, 7.0-8.0 mm, or 8.0-9.0 mm, or less than about 9.0 mm. In at least one embodiment, the distance 13003 is greater or less than the depth 9012 (FIG. 9). In some embodiments, a distance 13005 separates the inner surface 9026A from the side surface 9020C of the leg 9005. In various embodiments, the distance 13005 measures about 0.0-4.0 mm, 0.5-1.0 mm, 1.0-1.5 mm, 1.5 mm, 1.5-2.0 mm, 2.0-2.5 mm, 2.5-3.0 mm, 3.0-3.5 mm, or 3.5-4.0 mm, or less than about 4.0 mm. In one example, the distance 13005 is zero or substantially near zero such that the inner surface 9026A and the side surface 9020C are coplanar.

In various embodiments, the top surface 9002 of the bridge 9001 transitions downwardly at the edges 9006A-B to the side surfaces 9009A-B. In at least one embodiment, the side surfaces 9009A-B transition to side surfaces 12015A-B (FIG. 12) of the shoulder 9015 at the edges 9008A-B. In one or more embodiments, transitions of the top surface 9002 and the side surfaces 9009A-B are substantially non-breaking, thereby preserving a low profile construction of the bridge 9001.

FIG. 14 shows a side view of an exemplary staple 9000, according to one embodiment of the present disclosure. In various embodiments, the legs 9003A-B include outer surfaces 14001A-B. In at least one embodiment, the top surface 9002 and/or the side surfaces 9008A-B of the bridge 9001 transitions at shoulder 12002A-B to the outer surfaces 14001A-B. In one or more embodiments, transitions between the outer surfaces 14001A-B and the bridge 9001 are substantially non-breaking and rounded, thereby improving durability and torsional stability of the staple 9000 (e.g., as compared to previous staples demonstrating breaking curvature and/or sharp-angled connections that concentrate stress and thereby act as potential failure points).

In at least one embodiment, the leg 9007 includes an inner surface 14002. In various embodiments, the inner surface 14002 transitions to the side surface 12017 of the shoulder 9015. In one or more embodiments, the transition between the inner surface 14002 and the side surface 12017 is substantially non-breaking and rounded. In some embodiments, the inner surface 14002 transitions to the bridge bottom surface 12001 (FIG. 12).

FIG. 15 shows a cross-section 15000 of the staple 9000, in particular the bridge 9001. In various embodiments, the cross-section 15000 includes a top edge 15001 and a bottom edge 15005 that connect at ends 15003A-B. In at least one embodiment, the top edge 15001 is continuously curved between the ends 15002A-B. In some embodiments, the top edge 15001 demonstrates discontinuous curvature, for example, by including a substantially horizontal central portion 15004 that is bounded by curved portions 15003A-B. In one or more embodiments, the bottom edge 15005 is substantially horizontal between the ends 15002A-B. According to one embodiment, the ends 15002A-B are substantially rounded.

FIG. 16 shows a back view of an exemplary staple 9000, according to one embodiment of the present disclosure. In various embodiments the legs 9003B, 9005, and 9007 each include a side surface 16002A-C (e.g., opposite the side surface 9020 thereof each as shown in FIG. 9).

In various embodiments, the staple 9000 includes a width 16009 between radial points 16003, 16005. In at least one embodiment, the width 16009 measures at least about 20.0 mm, or about 20.0-30.0 mm, 20.0-21.0 mm, 22.0-23.0 mm, 23.0-24.0 mm, 24.0-25.0 mm, 24.0 mm, 24.9 mm, 25.0-26.0 mm, 26.0-27.0 mm, 27.0-28.0 mm, 28.0-29.0 mm, or 29.0-30.0 mm, or less than about 30.0 mm. In one or more embodiments, the staple 9000 includes a length 16011 between an apex 16007 of the bridge top surface 9002 and an end 10001B of the leg 9003B. In some embodiments, the apex 16007 may be positioned in a central region of the top surface 9002. In various embodiments, the length 16007 measures at least about 15.0 mm, or about 15.0-21.0 mm, 15.0-16.0 mm, 16.0 mm, 16.0-17.0 mm, 17.0-18.0 mm, 18.4 mm, 18.0-19.0 mm, 19.0-20.0 mm, or 20.0-21.0 mm, or less than about 21.0 mm. In at least one embodiment, the staple 9000 includes a length 16013 between the apex 16007 and an end 10003B of the leg 9005. In one or more embodiments, the length 16013 measures at least about 14.0 mm, or about 14.0-21.0 mm, 14.0, 14.0-15.0, 15.0-16.0 mm, 16.0-17.0 mm, 17.7 mm, 17.0-18.0 mm, 18.0-19.0 mm, 19.0-20.0 mm, or 20.0-21.0 mm, or less than about 21.0 mm.

Figure 17A:
FIGS. 17A-B show an exemplary finite element analysis, according to one embodiment of the present disclosure.
Figure 17A:
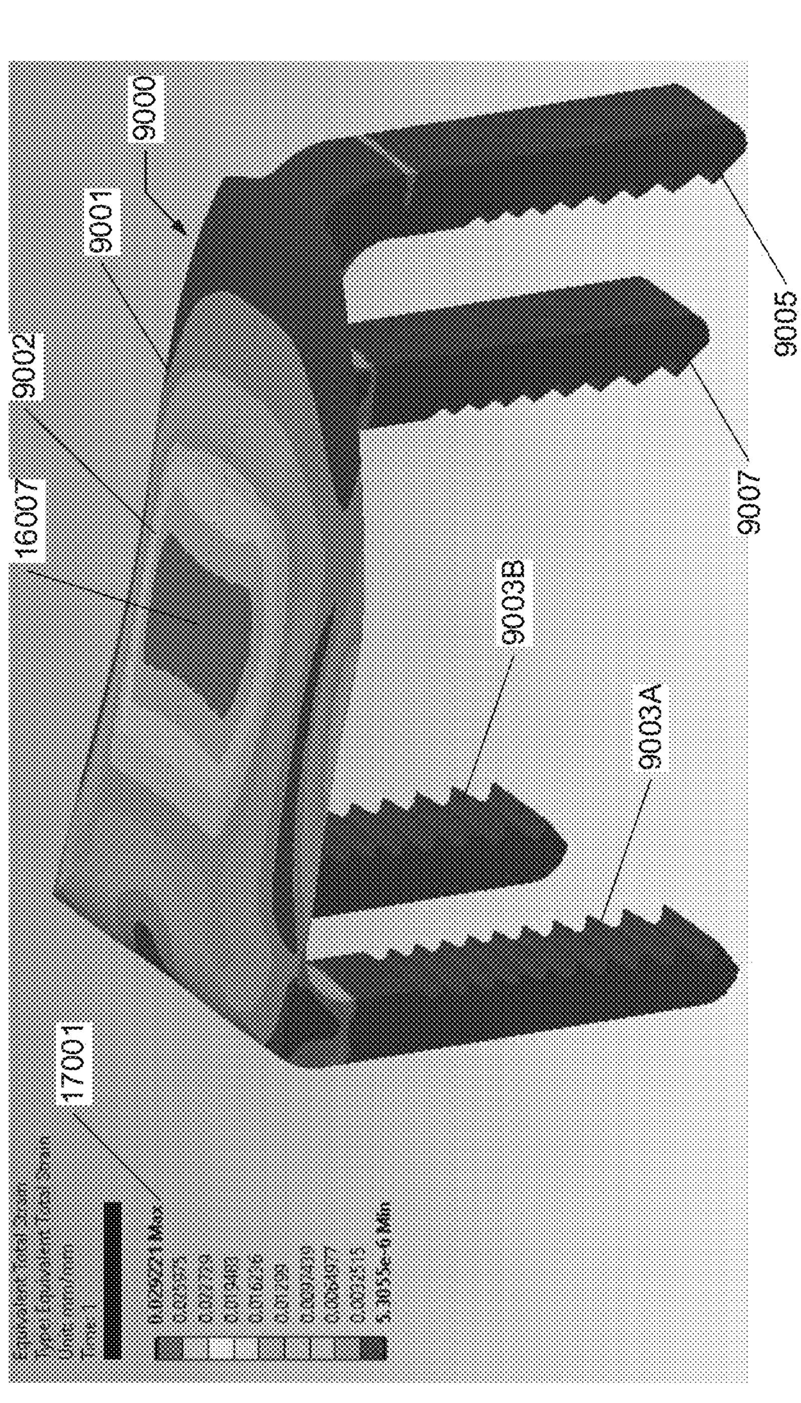

FIG. 17A shows an exemplary finite element analysis (FEA) 17000A of one embodiment of the staple 9000.

In various embodiments, the FEA 17000A measures strain 17001 throughout the staple 9000. According to one embodiment, the strain 17001 indicates stress concentrations of the staple 9000. In at least one embodiment, the FEA 17000A shows the advantageous concentration of stress to and distribution of stress throughout the bridge 9001. For example, the staple 9000 demonstrates increased strain 17001 throughout the bridge 9001 as compared to strain 17001 demonstrated in regions where the legs 9003A-B, 9005, 9007 connect to the bridge 9001. In this example, the increased strain 17001 of the bridge 9001 and decreased strain 17001 of the legs 9003A-B, 9005, 9007 indicates the advantageous concentration of stress to and throughout the bridge 9001. According to one embodiment, the substantially non-breaking construction and radial transitions of the top surface 9002 contributes to the concentration of stress to and distribution of stress throughout the bridge 9001.

In various embodiments, the legs 9003A-B, 9005, 9007 demonstrate a strain 17001 of less than about 0.01299 mm/mm, less than about 0.0097439 mm/mm, less than about 0.0065977 mm/mm, less than about 0.0032515 mm/mm, or at least about 0.00000053055 mm/mm. In one or more embodiments, towards the apex 16007, the top surface 9002 demonstrates a strain 17001 less than about 0.029221 mm/mm. In at least one embodiment, the strain 17001 of the top surface 9002 decreases toward the legs 9003A-B, 9005 and measures less than about 0.01299 mm/mm or at least about 0.00000053055 mm/mm.

Figure 17B:
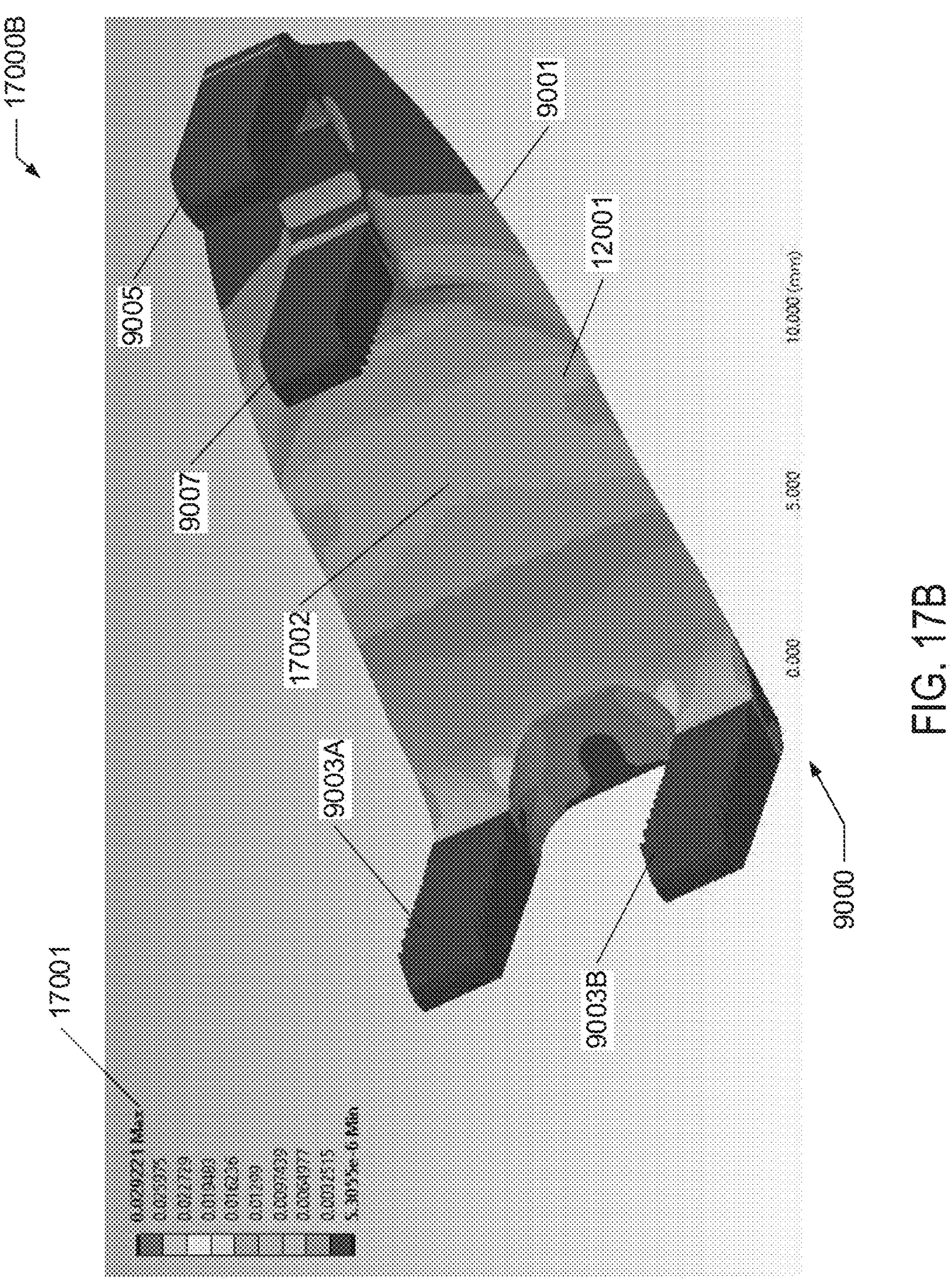

FIG. 17B shows an exemplary finite element analysis (FEA) 17000B of one embodiment of the staple 9000. In various embodiments, the FEA 17000B demonstrates the concentration of stress to and distribution of stress throughout the bridge 9001. According to one embodiment, the substantially non-breaking construction and radial transitions of the bottom surface 12001 contributes to the concentration of stress to and distribution of stress throughout the bridge 9001. In one or more embodiments, toward a center point 17002, the bottom surface 12001 demonstrates a strain 17001 of less than about 0.029221 mm/mm. In various embodiments, the strain 17001 of the bottom surface 12001 decreases toward the legs 9003A-B, 9005, 9007 and measures less than about 0.0097439 mm/mm or at least about 0.00000053055 mm/mm.

Figure 18A:
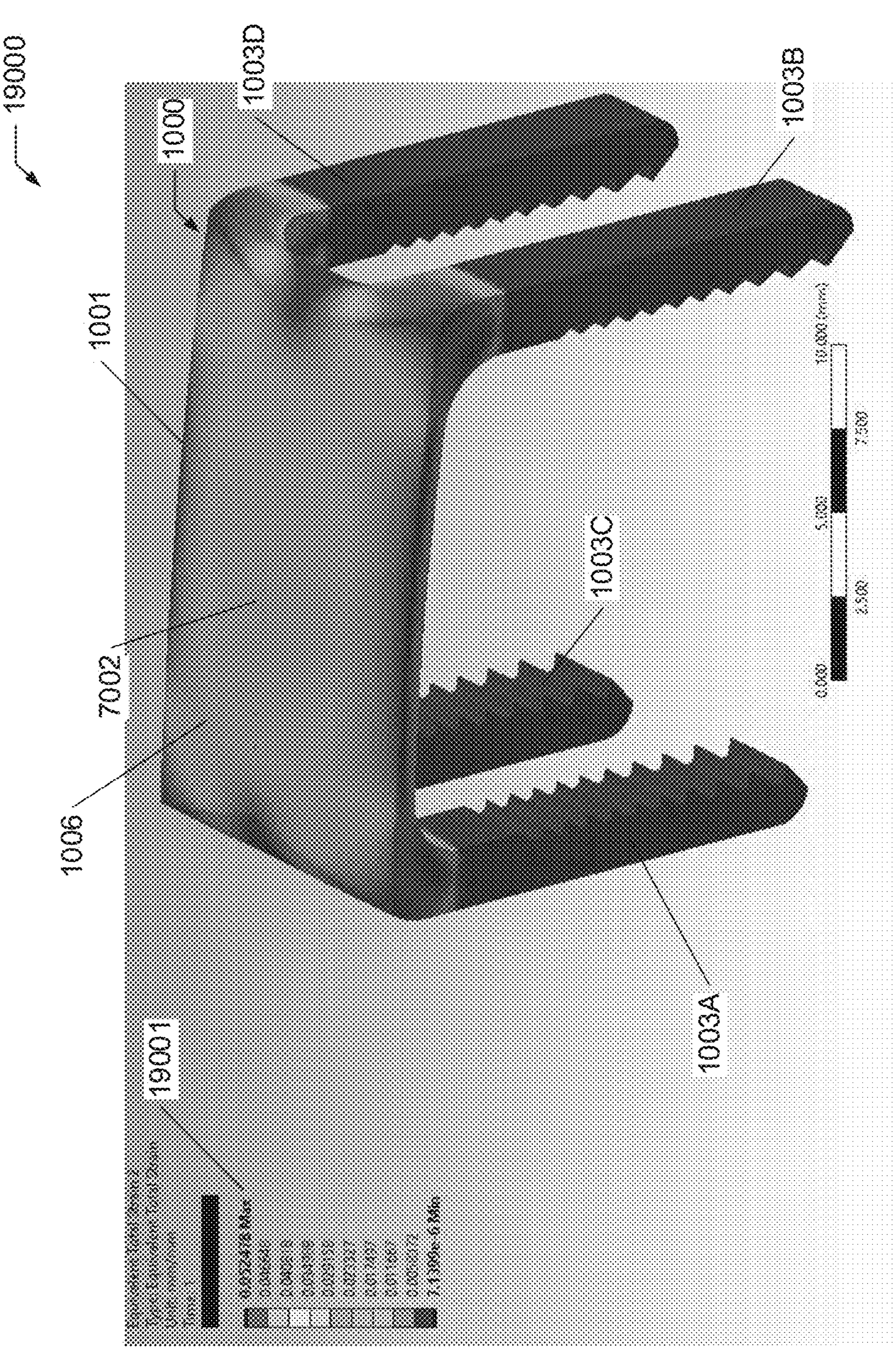
FIGS. 18A-B show an exemplary finite element analysis, according to one embodiment of the present disclosure.

FIG. 18A shows an exemplary finite element analysis (FEA) 18000A of one embodiment of the staple 1000.

In various embodiments, the FEA 18000A measures strain 18001 throughout the staple 1000. According to one embodiment, the strain 18001 indicates stress concentrations of the staple 1000. In at least one embodiment, the FEA 18000A shows the advantageous concentration of stress to and distribution of stress throughout the bridge 1001. For example, the staple 1000 demonstrates increased strain 18001 throughout the bridge 1001 as compared to strain 18001 demonstrated in regions where the legs 1003A-D connect to the bridge 1001. In this example, the increased strain 18001 of the bridge 1001 and decreased strain 18001 of the legs 1003A-D indicates the advantageous concentration of stress to and throughout the bridge 1001. According to one embodiment, the substantially non-breaking construction and radial transitions of the top surface 1006 contributes to the concentration of stress to and distribution of stress throughout the bridge 1001.

In various embodiments, the legs 1003A-D demonstrate a strain 18001 of less than about 0.023327 mm/mm, less than about 0.017497 mm/mm, less than about 0.011667 mm/mm, less than about 0.0058372 mm/mm, or at least about 0.00000071399 mm/mm. In one or more embodiments, towards the apex 7002, the top surface 1006 demonstrates a strain 18001 less than about 0.052478 mm/mm. In at least one embodiment, the strain 18001 of the top surface 1006 decreases toward the legs 1003A-D and measures less than about 0.011667 mm/mm or at least about 0.00000071399 mm/mm.

Figure 18B:
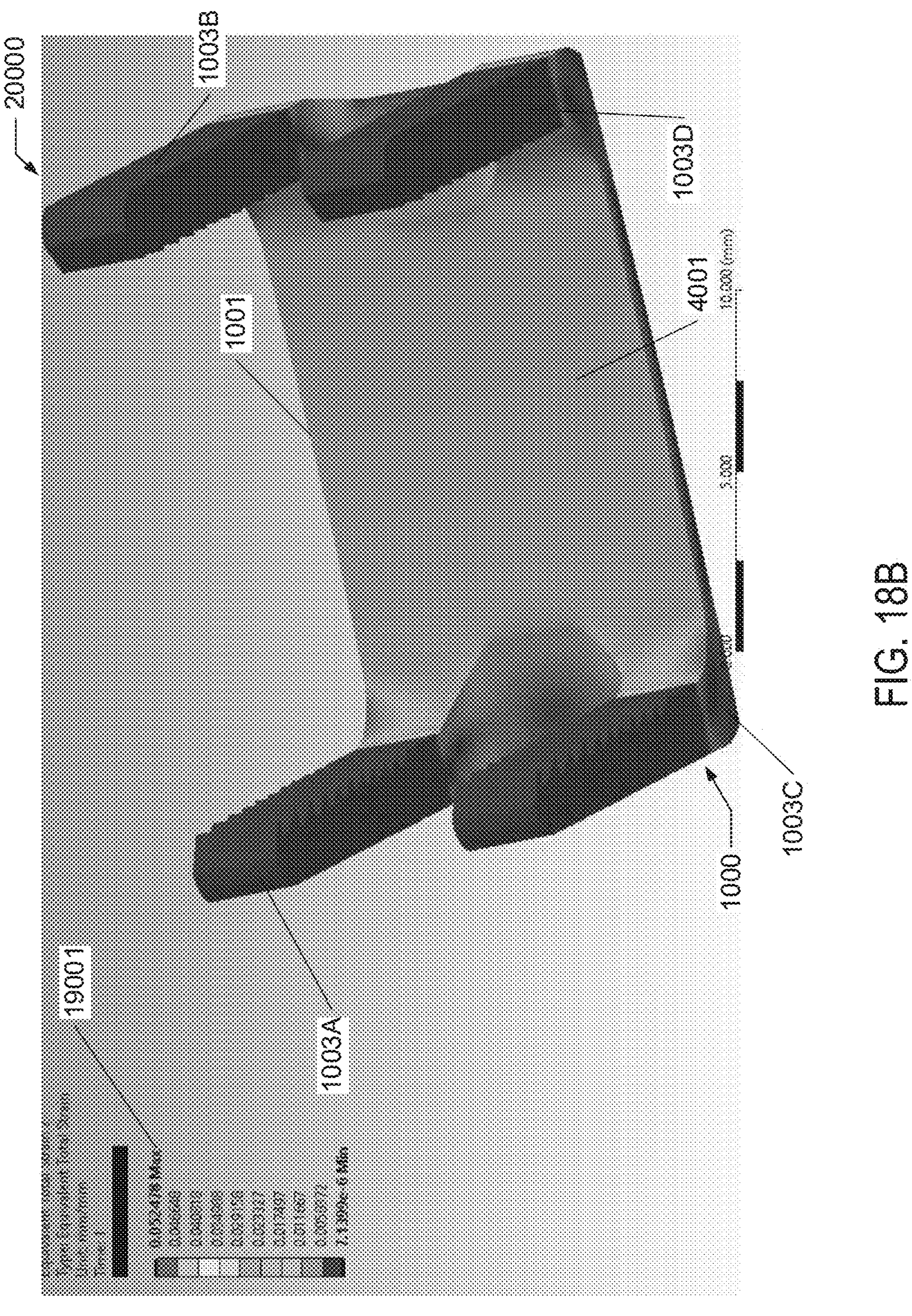

FIG. 18B shows an exemplary finite element analysis (FEA) 18000B of one embodiment of the staple 9000. In various embodiments, the FEA 18000B demonstrates the concentration of stress to and distribution of stress throughout the bridge 9001. According to one embodiment, the substantially non-breaking construction and radial transitions of the bottom surface 12001 contributes to the concentration of stress to and distribution of stress throughout the bridge 9001. In one or more embodiments, toward a center point 18002, the bottom surface 12001 demonstrates a strain 18001 of less than about 0.029221 mm/mm. In various embodiments, the strain 18001 of the bottom surface 12001 decreases toward the legs 9003A-B, 9005, 9007 and measures less than about 0.0097439 mm/mm or at least about 0.00000053055 mm/mm.

Figure 19:
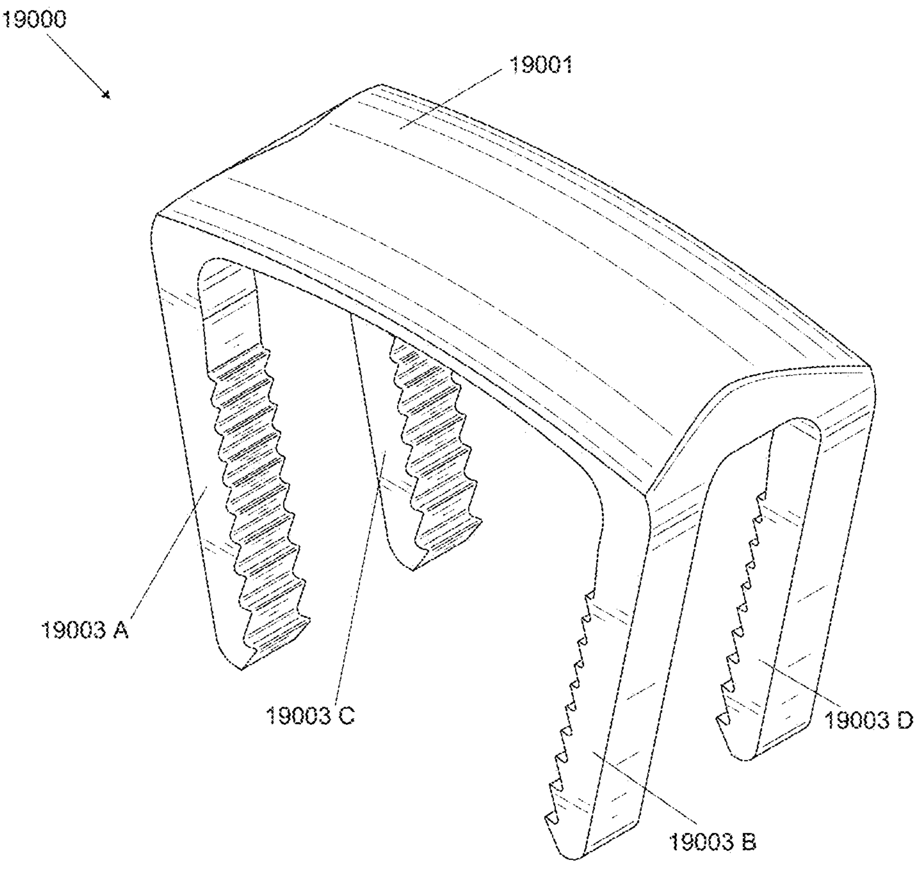
FIG. 19 shows a perspective view of an exemplary staple, according to one embodiment of the present disclosure.
Figure 20:
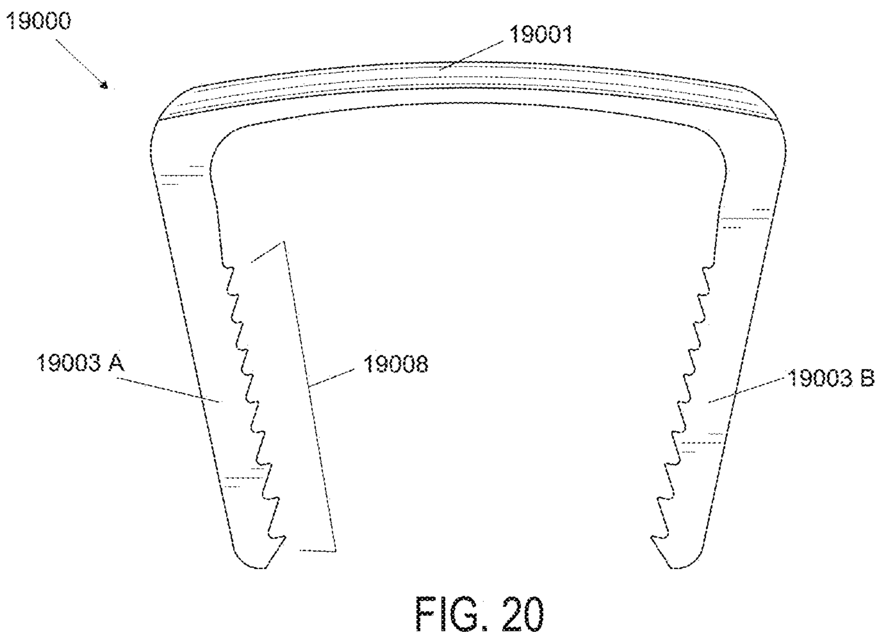
FIG. 20 shows a front view of an exemplary staple, according to one embodiment of the present disclosure.
Figure 21:
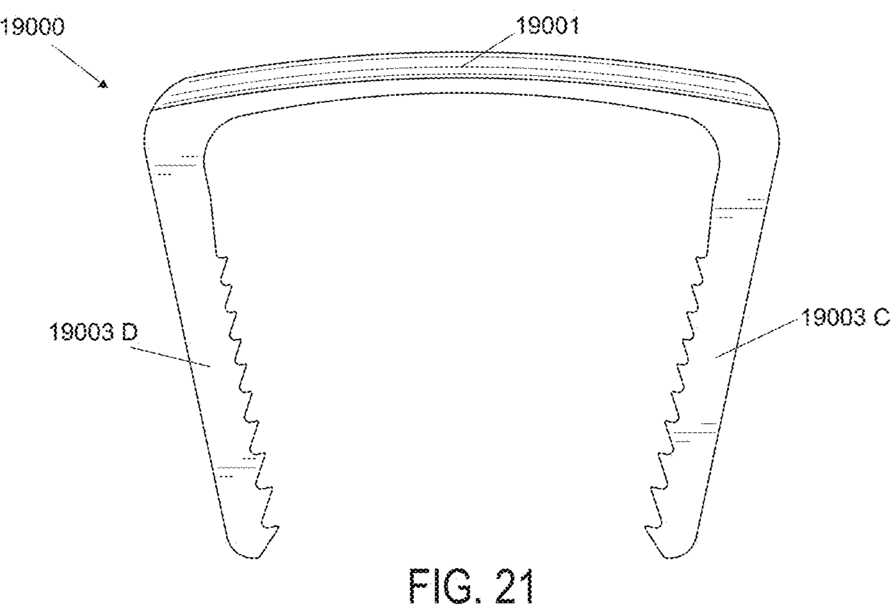
FIG. 21 shows a back view of an exemplary staple, according to one embodiment of the present disclosure.
Figure 22:
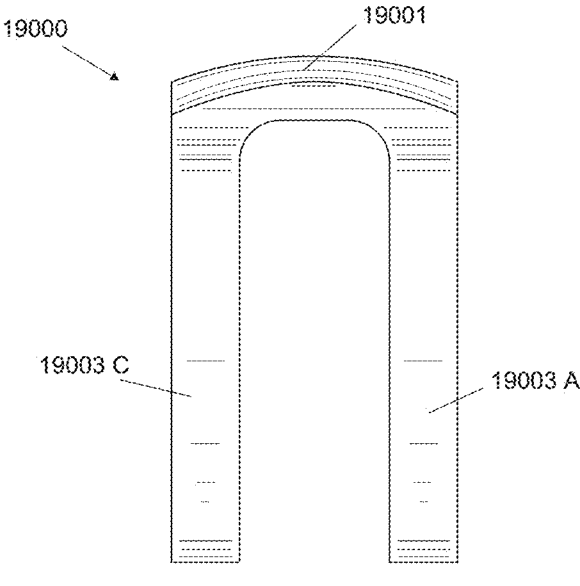
FIG. 22 shows a side view of an exemplary staple, according to one embodiment of the present disclosure.
Figure 23:
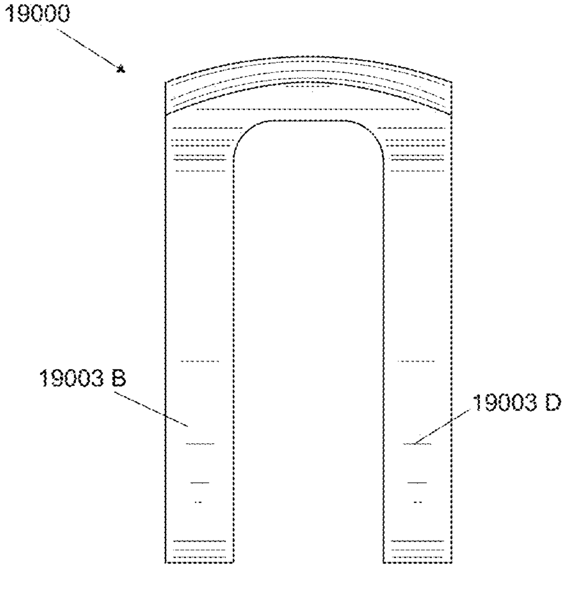
FIG. 23 shows a side view of an exemplary staple, according to one embodiment of the present disclosure.
Figure 121:
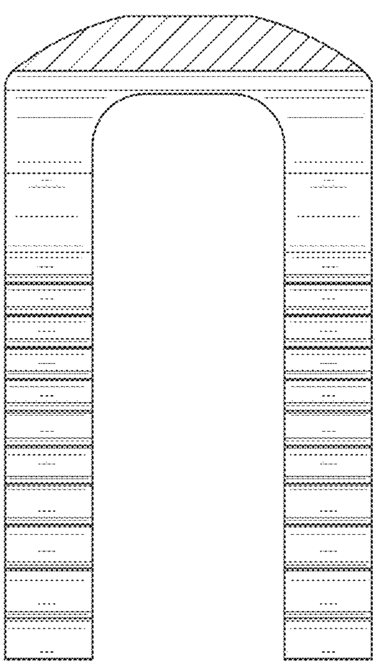

FIGS. 19 to 121 include additional embodiments having features and characteristics substantially similar to those already described. For the sake of brevity and consistency, only select additional features are described below. Generally, any features and/or characteristics of an exemplary staple described or shown herein may apply to other staples described or shown herein.

Specifically, FIGS. 19 to 26 show various views of an exemplary staple 19000 similar to the embodiments shown in FIGS. 1 to 8. In various embodiments, the staple 19000 includes a bridge 19001 and legs 19003 A-D. According to one embodiment, the staple 19000 size (e.g., bridge 19001 length×leg 19003 A-D length×leg 19003 A-D length) may be greater than, less than or equal to about 18.0×16.0×16.0 mm, or about 22.0×16.0×16.0 mm, or about 22.0×20.0×20.0 mm, or any other size according to the principles of this disclosure. In one or more embodiments, at least one surface of at least one of legs 19003A-D includes one or more teeth sections 19008 (see FIG. 20). In some embodiments, the one or more teeth sections 19008 protrude from the at least one surface of the at least one of legs 19003A-D. As discussed herein, the bridge 19001 may be defined as between one or more radial tangents.

Figure 24:
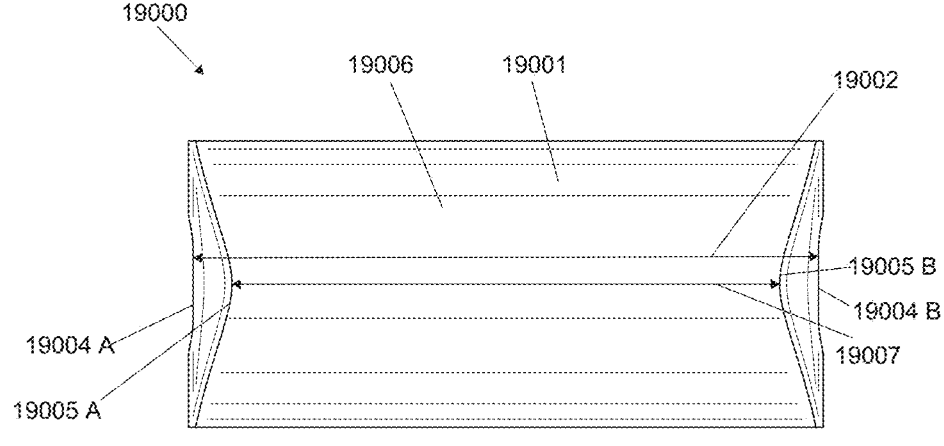
FIG. 24 shows a top view of an exemplary staple, according to one embodiment of the present disclosure.
Figure 25:
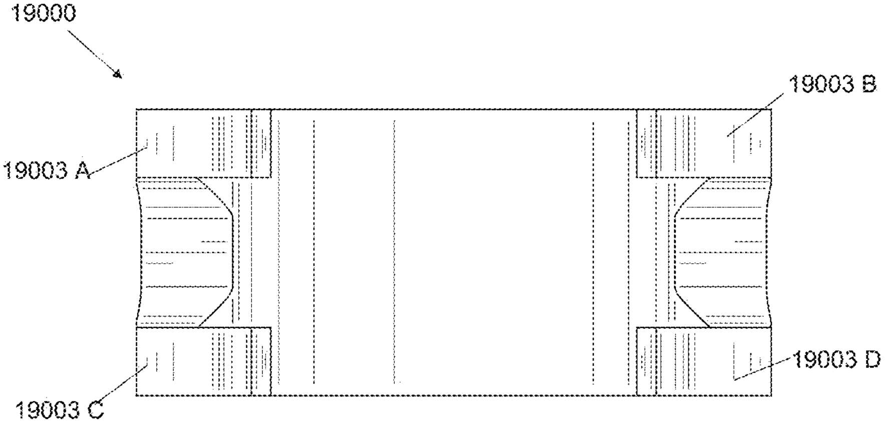
FIG. 25 shows a bottom view of an exemplary staple, according to one embodiment of the present disclosure.
Figure 26:
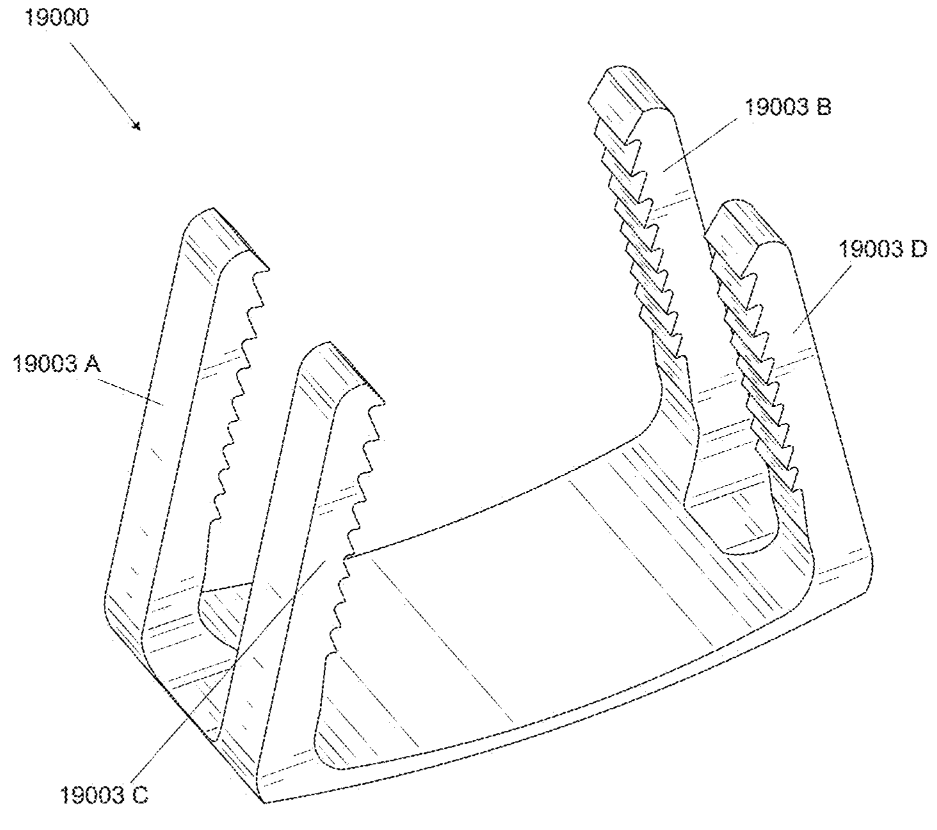
FIG. 26 shows a perspective view of an exemplary staple, according to one embodiment of the present disclosure.

With reference to FIG. 24, in one or more embodiments, the bridge 19001 includes a length 19002 between ends 19004A, 19004B. According to one embodiment, the length 19002 measures at least about 16.0 mm, or about 16.0-30.0 mm, or about 16.0-18.0 mm, or about 18.98 mm, or about 18.0-20.0 mm, or about 20.0-22.0 mm, or about 20.1 mm, or about 22.0-24.0 mm, or about 22.9 mm, or about 24.0-26.0 mm, or about 26.0-30.0 mm, or less than about 30.0 mm. In various embodiments, a top surface 19006 of the bridge 19001 includes a length 19007 between ends 19005A, 19005B. In at least one embodiment, the length 19007 measures at least about 14.0 mm, or about 14.0-24.0 mm, or about 14.0-16.0 mm, or about 16.148 mm, or about 16.0-18.0 mm, or about 18.0-20.0 mm, or about 20.0-22.0 mm, or about 20.1 mm, or about 22.0-24.0 mm, or less than about 24.0 mm.

FIGS. 27 to 34 show various views of an exemplary staple 27000 similar to the embodiments shown in FIGS. 9 to 16. In various embodiments, the staple 27000 includes a bridge 27001, legs 27003A-B, leg 27005, and leg 27007. According to one embodiment, the staple 27000 size (e.g., bridge 27001 length×leg 27003A-B length×leg 27005 length×leg 27007 length) may be greater than, less than or equal to about 24.0×16.0×14.0×12.0 mm, or about 28.0×16.0×14.0×12.0 mm, or about 32.0×16.0×14.0×12.0 mm. In one or more embodiments, at least one surface of at least one of legs 27003A-B, 27005, 27007 include one or more teeth sections 19008 (see FIG. 28). In some embodiments, the one or more teeth sections 27009 protrude from the at least one surface of the at least one of legs 27003A-B, 27005, 27007.

Figure 32:
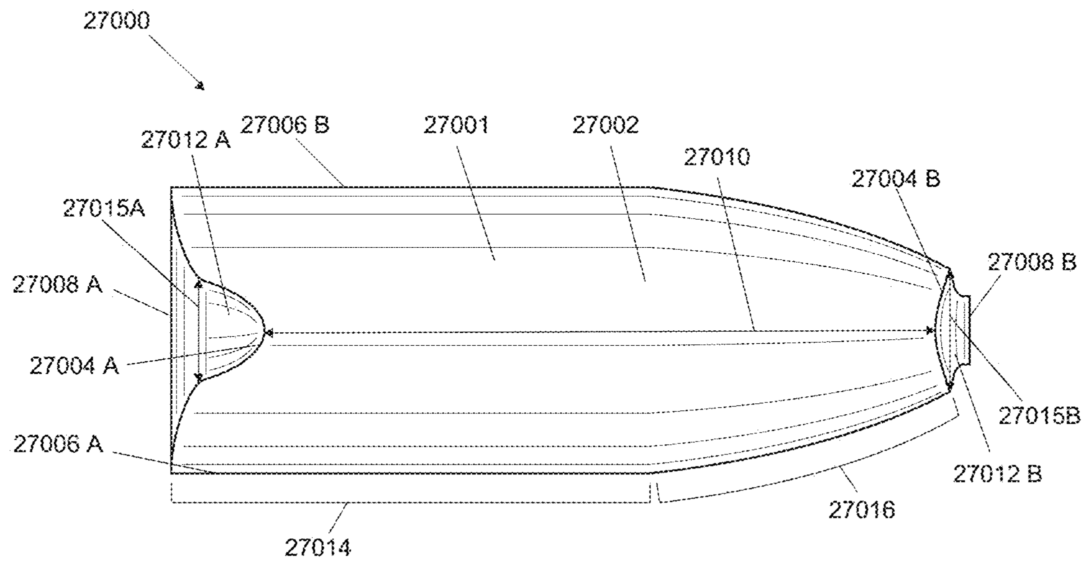
FIG. 32 shows a top view of an exemplary staple, according to one embodiment of the present disclosure.

With reference to FIG. 32, in at least one embodiment, the bridge 27001 includes a top surface 27002 defined by a first edge 27004A, a second edge 27004B, and sides 27006A-B. In some embodiments, the top surface 27002 may be a continuously curved, substantially smooth, or otherwise continuous top surface 27002A (shown in FIG. 30-31). In some embodiments, the bridge 27001 includes an end 27008A that borders a portion of the top surface 27002 defined by the first edge 27004A to the legs 27003A-B. In some embodiments, the first edge 27004A may include a substantially U-shaped, V-shaped, parabolic, triangular-shaped, quadrilateral-shaped, circularly shaped, irregularly shaped, or round shaped, or any other suitably shaped contour. In some embodiments, the first edge 27004B may demonstrate a substantially U-shaped, V-shaped, parabolic, triangular-shaped, quadrilateral-shaped, circularly shaped, irregularly shaped, or round shaped, or any other suitably shaped contour. According to one embodiment, the sides 27006A-B may demonstrate a curved contour (e.g., having constant curvature throughout; having varying curvature throughout, having a substantially straight contour followed by inward curvature, etc.) between the first edge 27004A to the second edge 27004B.

In various embodiments, the bridge 27001 includes a length 27010 disposed between the first edge 27004A and the second edge 27004B. The length 27010 may measure at least about 14.0 mm, or about 14.0-32.0 mm, or about 14.0-16.0 mm, or about 16.0-18.0 mm, or about 17.0-20.0 mm, or about 18.96 mm, or about 19.22 mm, or about 19.42 mm, or about 18.0-22.0 mm, or about 22.0-24.0 mm, or about 24.0-26.0 mm, or about 26.0-28.0 mm, or about 28.0-30 mm, or about 30.0-32.0 mm, or less than about 32.0 mm. In some embodiments, the staple 27000 may be substantially symmetrical along the length 27010 while in other embodiments, the staple may be asymmetrical along the length 27010.

According to some embodiments, each of sides 27006A-B comprise a first arc 27014 and a second arc 27016. In some embodiments, a length of the first arc 27014 measures at least about 10.0 mm, or about 10.0-24.0 mm, or about 10.0-12.0 mm, or about 12.0-14.0 mm, or about 13.19 mm, or about 13.33 mm, or about 14.0-16.0 mm, or about 16.0-18.0 mm, or about 17.57 mm, or about 18.0-20.0 mm, or about 20.0-22.0 mm, or about 22.0-24.0 mm, or about 22.14 mm, or less than about 24.0 mm. In some embodiments, a length of the second arc 27016 measures at least about 8.0 mm, or about 8.0-16.0 mm, or about 8.0-10.0 mm, or about 10.0-12.0 mm, or about 11.32 mm, or about 11.52 mm, or about 11.79 mm, or about 12.0-14.0 mm, or about 13.01 mm, or about 14.0-16.0 mm, or less than about 16.0 mm.

In some embodiments, the length 27010 and contour of the bridge 27001 may affect curvature/transition from the bridge 27001 to leg 27007. In some embodiments, the bridge 27000 includes a span 27015A of first edge 27004A and measuring about at least about 2.0 mm, or about 2.0-8.0 mm, or about 2.0-6.0 mm, or about 3.64 mm, or about 3.90 mm, or about 5.62 mm, or about 6.0-8.0 mm, or less than about 8.0 mm. In some embodiments, the bridge 27000 includes a span 27015B of second edge 27004B and measuring about at least about 2.0 mm, or about 2.0-6.0 mm, or about 2.0-4.0 mm, or about 4.26 mm, or about 4.0-6.0 mm, or less than about 6.0 mm.

In some embodiments, the staple 27000 includes a first curve 27018A (shown in FIG. 28)—defined by a transition from span 27015A to the end 27008A—and measuring at least about 2.0 mm, or about 2.0-10.0 mm, or about 2.0-4.0 mm, or about 3.0 to 5.0 mm, or about 3.09 mm, or about 4.0-6.0 mm, or about 4.06 mm, or about 4.47 mm, or about 6.0-8.0 mm, or about 8.0-10.0 mm, or less than about 10.0 mm. In some embodiments, the staple 27000 includes a second curve 27018B (shown in FIG. 28)—defined by a transition from span 27015B to the end 27008B—and measuring at least about 1.0 mm, or about 1.0-7.0 mm, or about 1.0-3.0 mm, or about 1.80 mm, or about 2.42 mm, or about 2.54 mm, or about 3.0 to 5.0 mm, or about 5.0-7.0 mm, or less than about 7.0 mm.

In some embodiments, the bridge 27001 includes a first divot 27012A defined by end 27008A and first edge 27004A, and a second divot 27012B defined by end 27008B and second edge 27004B, wherein each divot 27012A-B may form a U-shape, V-shape, parabolic shape, triangular shape, quadrilateral shape, circular shape, irregular shape, round shape, or any other suitable shape beneficial for stress reduction and torsional stability. In some embodiments, the first divot 27012A may include an overall perimeter measuring at least about 20.0 mm, or about 20.0-30.0 mm, or about 20.0-25.0 mm, or about 25.0-30.0 mm, or about 25.18 mm, or about 27.78 mm, or about 27.96 mm, or less than about 30.0 mm. In some embodiments, the second divot 27012 B may include an overall perimeter measuring at least about 5.0 mm, or about 5.0-15.0 mm, or about 5.0-10.0 mm, or about 9.41 mm, or about 10.0-15.0 mm, or about 11.76 mm, or about 12.30 mm, or less than about 15.0 mm.

In some embodiments, the first divot 27012A and second divot 27102B may each include an approximate depth measuring at least about 0.05 mm, or about 0.05-4.0 mm, or about 0.05-0.10 mm, or about 0.10-0.5 mm, or about 0.5-2.0 mm, or about 1.0-2.5 mm, or about 2.0-4.0 mm, or less than about 4.0 mm. In some embodiments, the approximate depth of the first divot 27012A may be different from the second divot 27012B.

Figure 33:
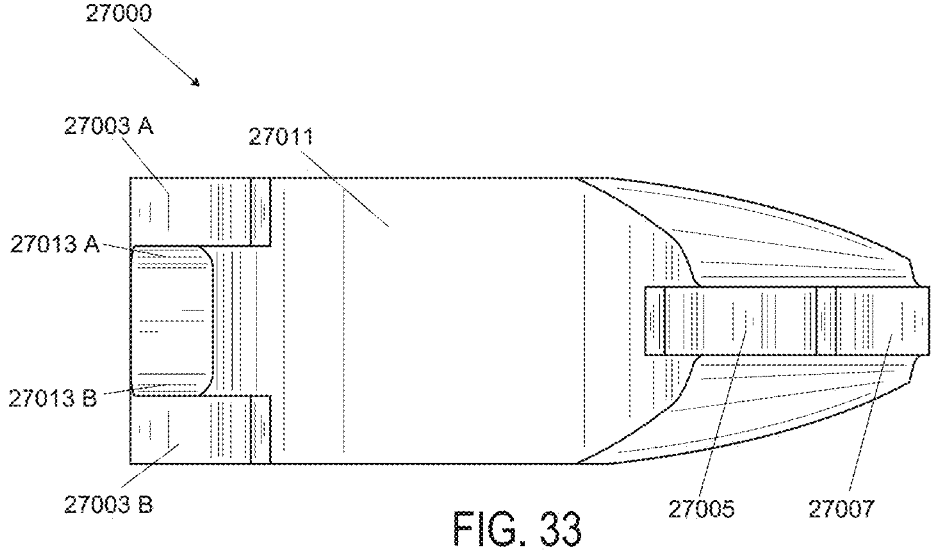
FIG. 33 shows a bottom view of an exemplary staple, according to one embodiment of the present disclosure.
Figure 34:
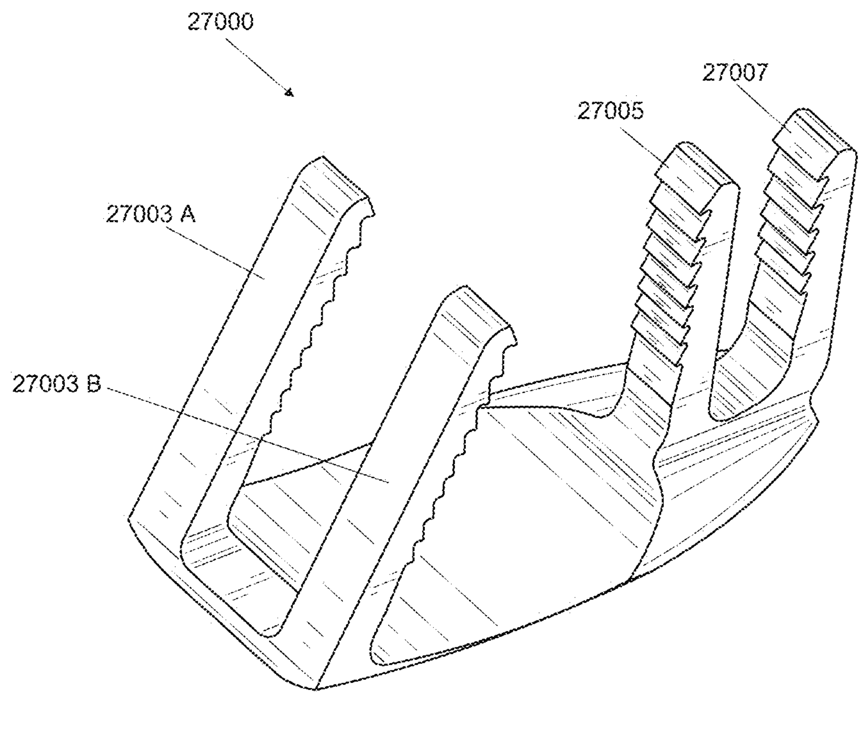
FIG. 34 shows a perspective view of an exemplary staple, according to one embodiment of the present disclosure.

Turning to FIG. 33, in at least one embodiment, the staple 27000 includes a bottom surface 27011. In one or more embodiments, the staple 27000 includes shoulders 27013A-B connecting the legs 27003A-B to the bridge 27001 (see FIG. 32). In various embodiments, the shoulders 27013A-B may gradually transition, continuously transition, sharply transition, or irregularly transition from the bottom surface 27011 to inner surfaces (not shown) of the legs 27003A-B.

Figure 35:
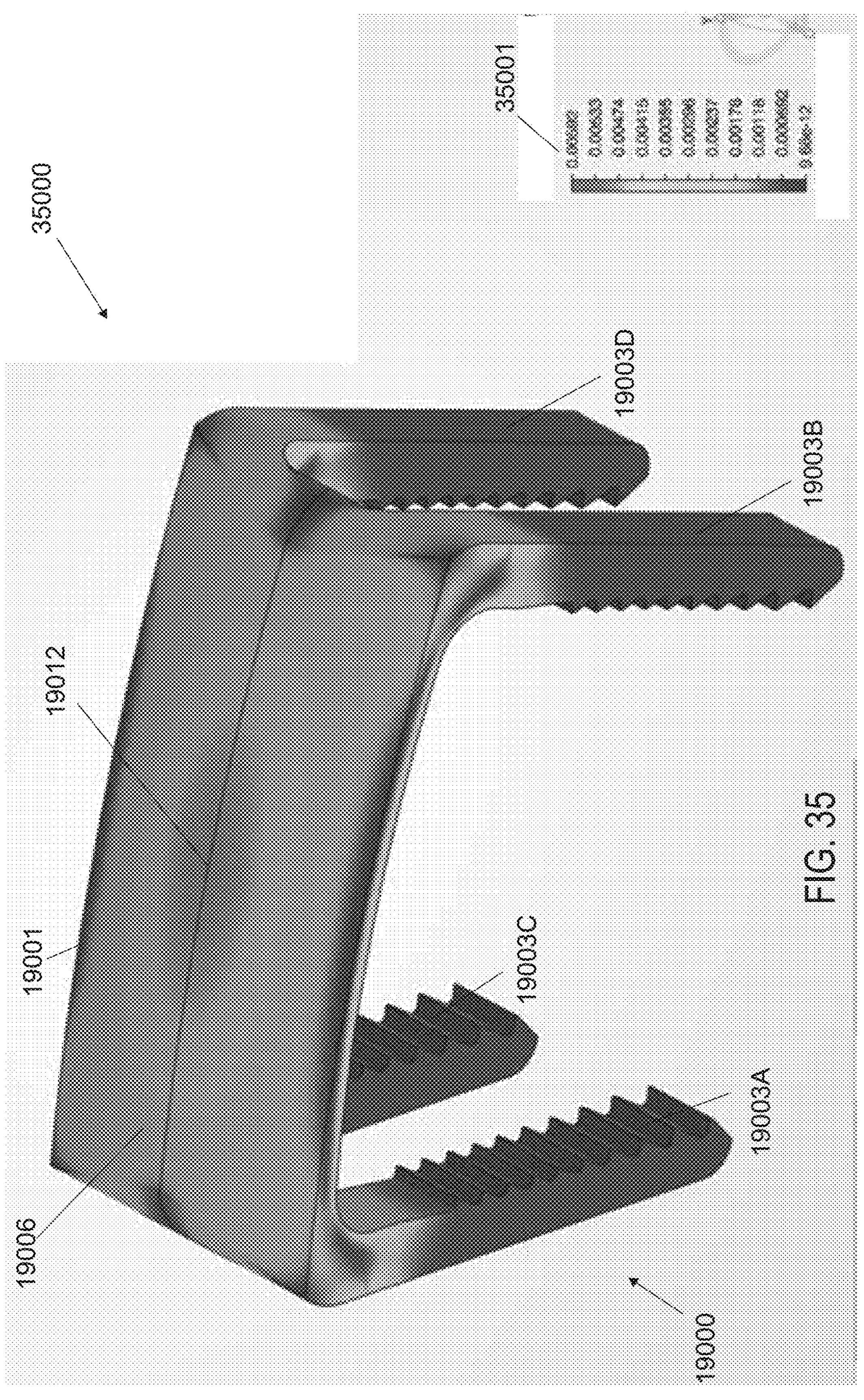
FIG. 35 shows an exemplary finite element analysis, according to one embodiment of the present disclosure.

FIG. 35 shows an exemplary finite element analysis (FEA) 35000 of one embodiment of the staple 19000. In various embodiments, the FEA 35000 measures strain 35001 throughout the staple 19000. According to one embodiment, the strain 35001 indicates stress concentrations of the staple 19000. In at least one embodiment, the FEA 35000 shows the advantageous concentration of stress to and distribution of stress throughout the bridge 19001. For example, the staple 19000 demonstrates increased strain 35001 throughout the bridge 19001 as compared to strain 35001 demonstrated in regions where the legs 19003A-D connect to the bridge 19001. In this example, the increased strain 35001 of the bridge 19001 and decreased strain 35001 of the legs 19003A-D indicates the advantageous concentration of stress to and throughout the bridge 19001. According to one embodiment, the substantially non-breaking construction and radial transitions of the top surface 19006 contributes to the concentration of stress to and distribution of stress throughout the bridge 19001.

In various embodiments, the legs 19003A-D demonstrate a strain 35001 of less than about 0.00237 mm/mm, about 0.00178 mm/mm, about 0.00118 mm/mm, about 0.000592 mm/mm, or at least about $9.68e^{-12}$ mm/mm. In one or more embodiments, towards an apex 19012, the top surface 19006 demonstrates a strain 35001 less than about 0.00592 mm/mm, or about 0.00533 mm/mm, or about 0.00474 mm/mm, or about 0.00415 mm/mm, or at least about 0.00355 mm/mm. In at least one embodiment, the strain 35001 of the top surface 19006 decreases toward the legs 19003A-D and measures less than about 0.00415 mm/mm to at least about $9.68e^{-12}$ mm/mm.

Figure 36:
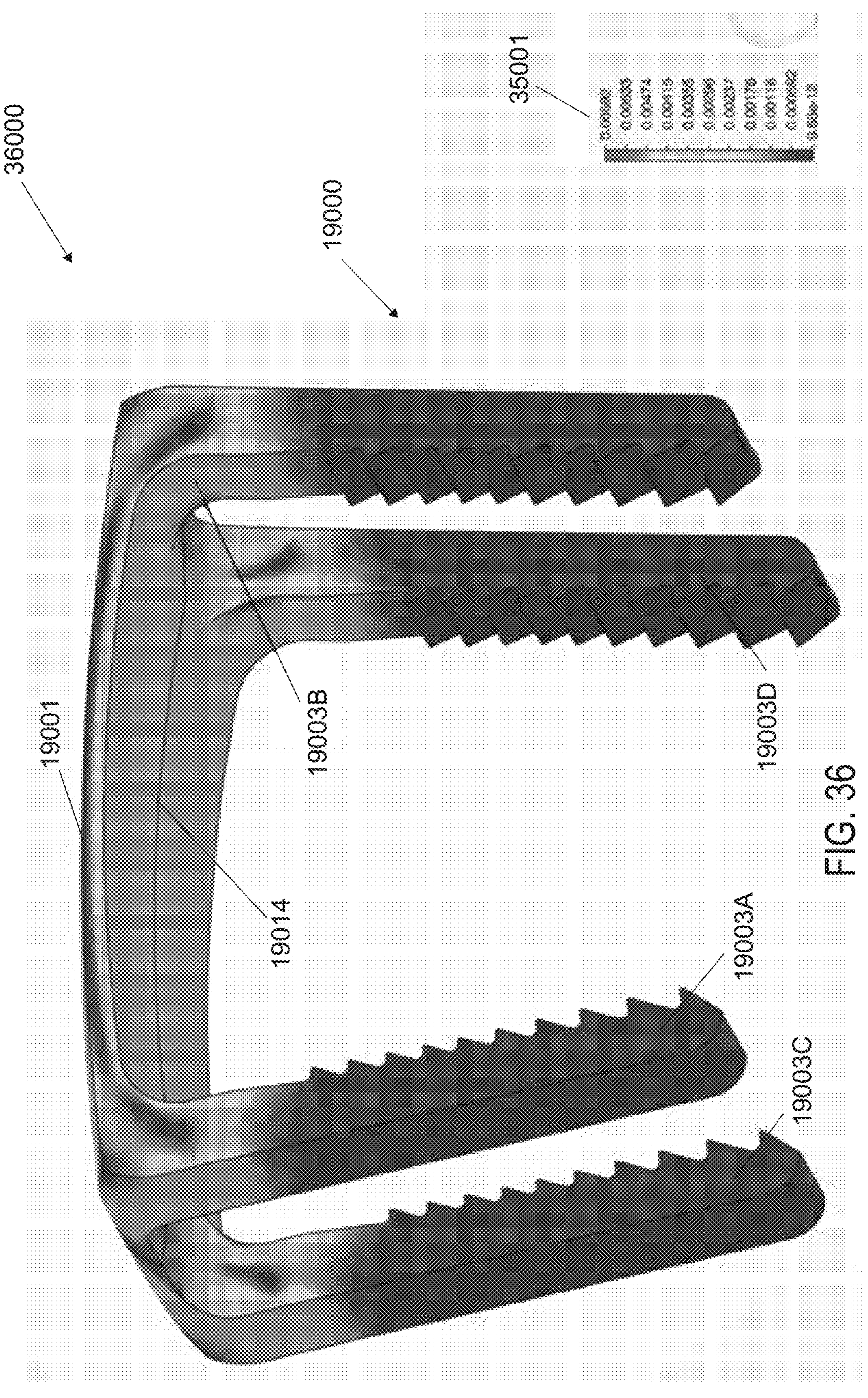
FIG. 36 shows an exemplary finite element analysis, according to one embodiment of the present disclosure.

FIG. 36 shows an exemplary finite element analysis (FEA) 36000 of one embodiment of the staple 19000. In various embodiments, the FEA 36000 demonstrates the concentration of stress to and distribution of stress throughout the bridge 19001. According to one embodiment, the substantially non-breaking construction and radial transitions of a bottom surface 19014 contributes to the concentration of stress to and distribution of stress throughout the bridge 19001. In various embodiments, the strain 35001 of the bottom surface 19014 decreases toward the legs 19003A-D and measures about less than 0.00415 mm/mm, about 0.00355 mm/mm, about 0.00296 mm/mm, about 0.00237 mm/mm, about 0.00178 mm/mm, about 0.00118, about 0.000592 mm/mm, or at least about $9.68e^{-12}$ mm/mm.

Figure 37:
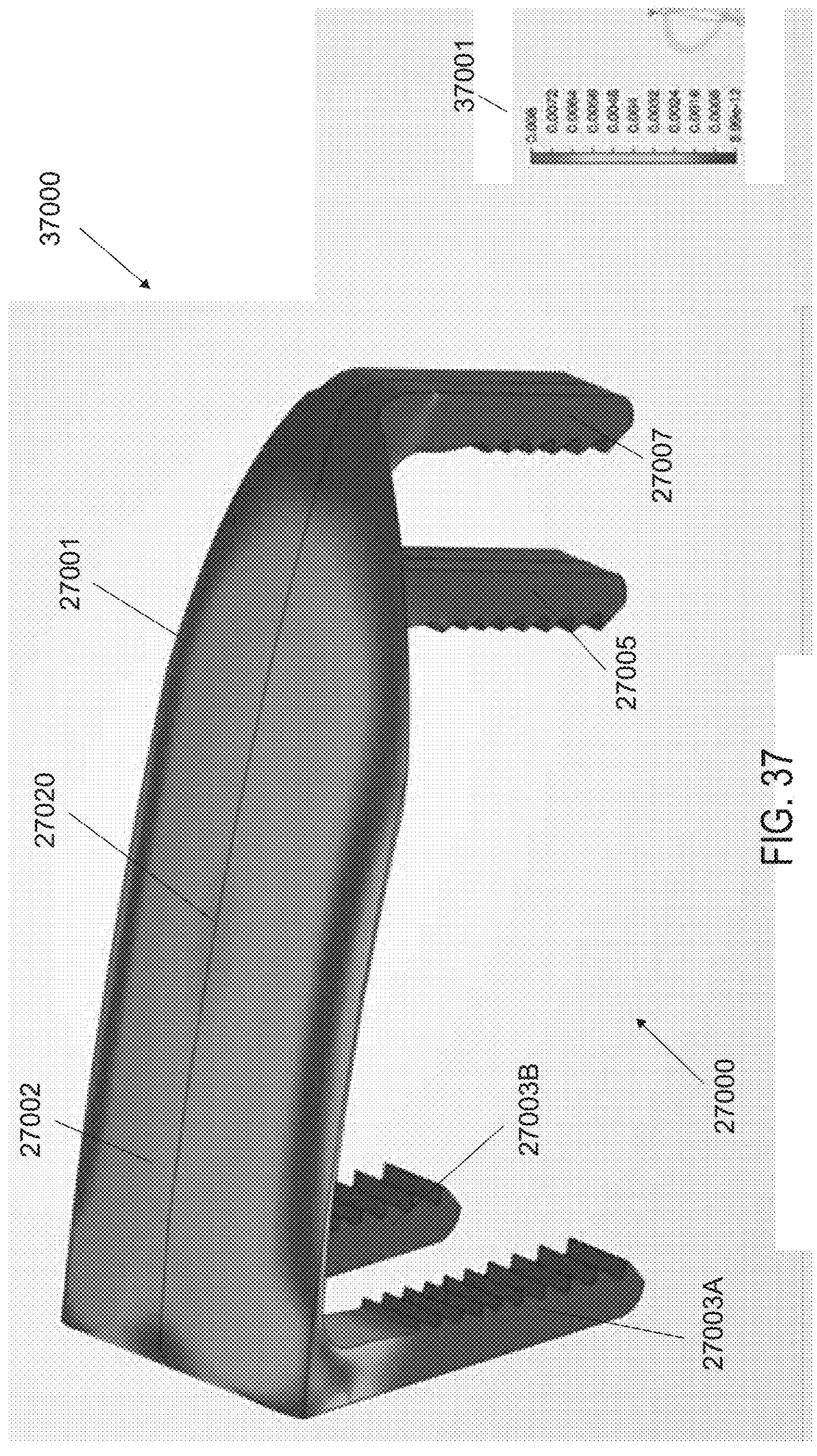
FIG. 37 shows an exemplary finite element analysis, according to one embodiment of the present disclosure.

FIG. 37 shows an exemplary finite element analysis (FEA) 37000 of one embodiment of the staple 27000. In various embodiments, the FEA 37000 measures strain 37001 throughout the staple 27000. According to one embodiment, the strain 37001 indicates stress concentrations of the staple 27000. In at least one embodiment, the FEA 37000 shows the advantageous concentration of stress to and distribution of stress throughout the bridge 27001. For example, the staple 27000 demonstrates increased strain 37001 throughout the bridge 27001 as compared to strain 37001 demonstrated in regions where the legs 27003A-B, 27005, 27007 connect to the bridge 27001. In this example, the increased strain 37001 of the bridge 27001 and decreased strain 37001 of the legs 27003A-B, 27005, 27007 indicates the advantageous concentration of stress to and throughout the bridge 27001. According to one embodiment, the substantially non-breaking construction and radial transitions of the top surface 27002 contributes to the concentration of stress to and distribution of stress throughout the bridge 27001.

In various embodiments, the legs 27003A-B, 27005, 27007 demonstrate a strain 37001 of less than about 0.004 mm/mm, about 0.0032 mm/mm, about 0.0024 mm/mm, about 0.0016 mm/mm, about 0.0006 mm/mm, or at least about $8.99e^{-12}$ mm/mm. In one or more embodiments, and towards an apex 27020, the top surface 27002 demonstrates a strain 37001 less than about 0.008 mm/mm, or about 0.0072 mm/mm, or about 0.0064 mm/mm, or about 0.0056 mm/mm, or at least about 0.0048 mm/mm.

Figure 38:
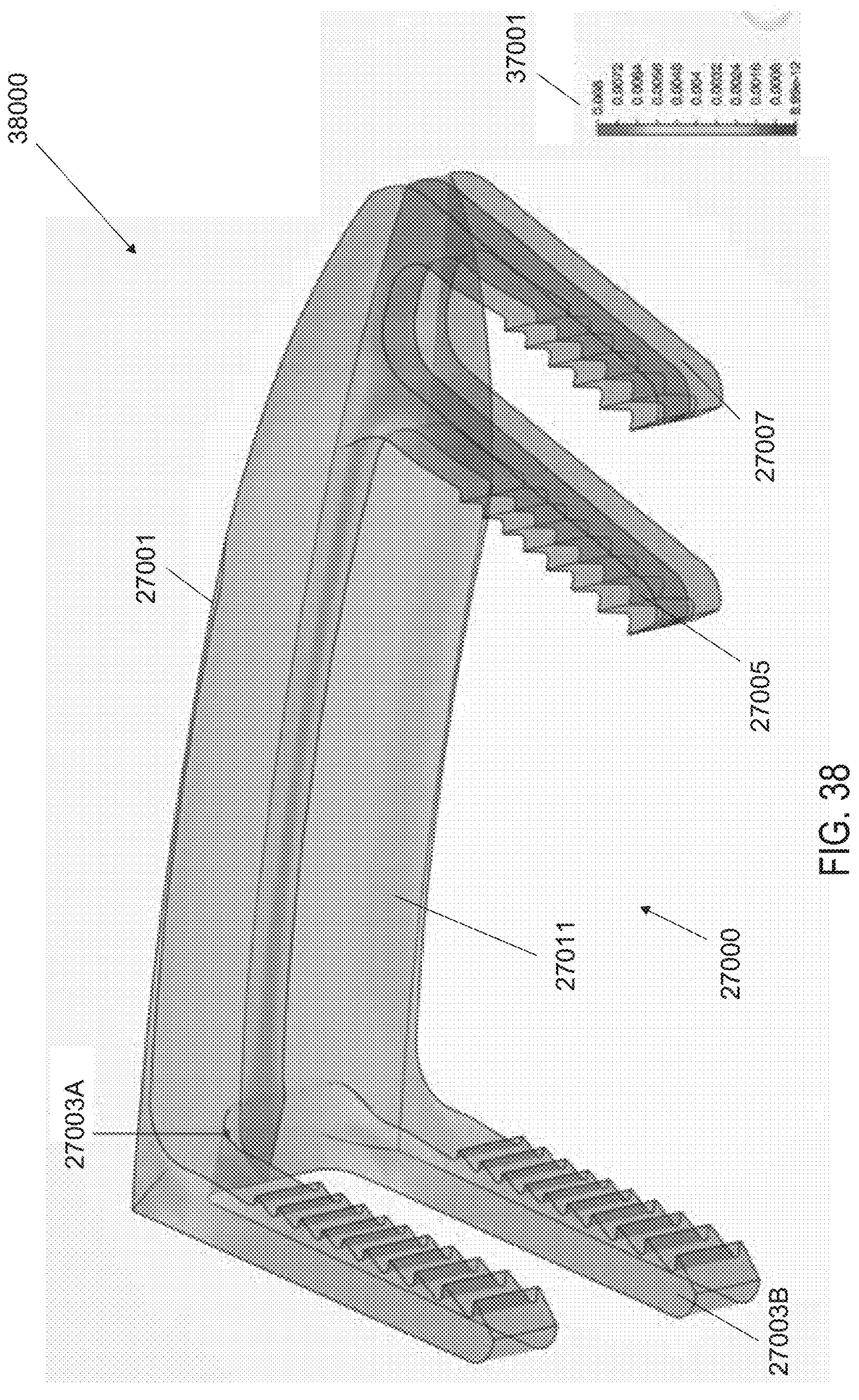
FIG. 38 shows an exemplary finite element analysis, according to one embodiment of the present disclosure.
Figure 39:
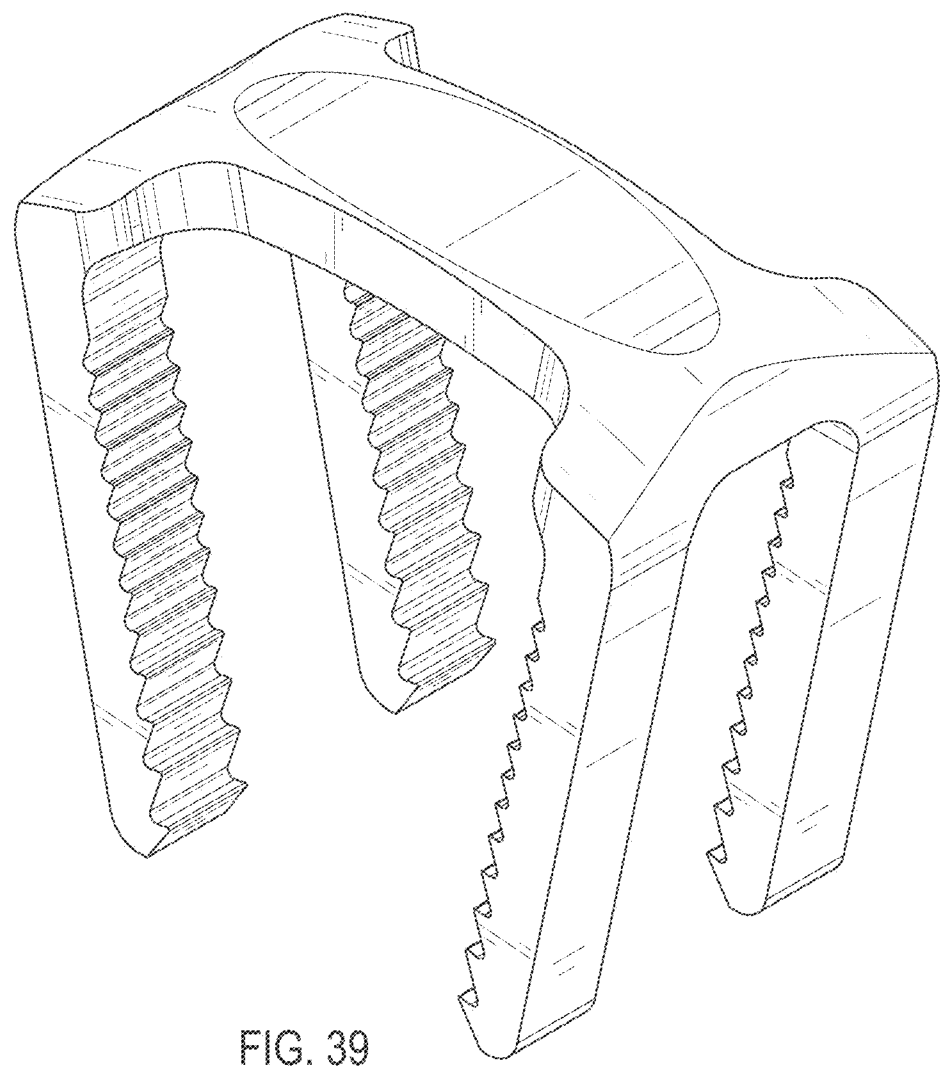
FIGS. 39 to 121 show additional exemplary staple embodiments contemplated herein.
Figure 40:
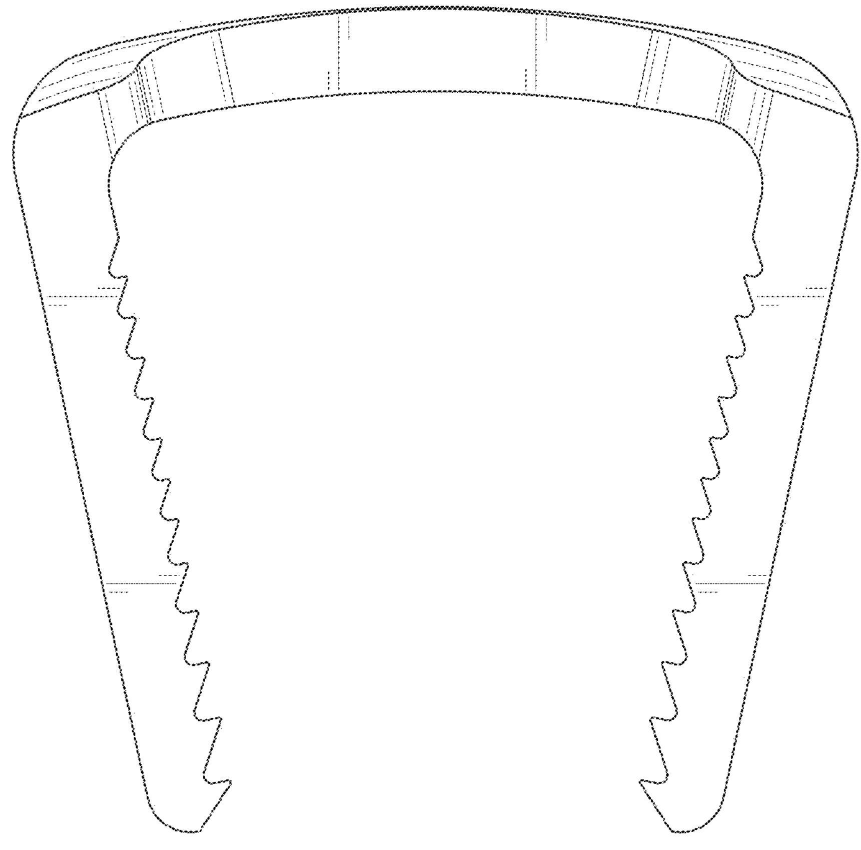
Figure 41:
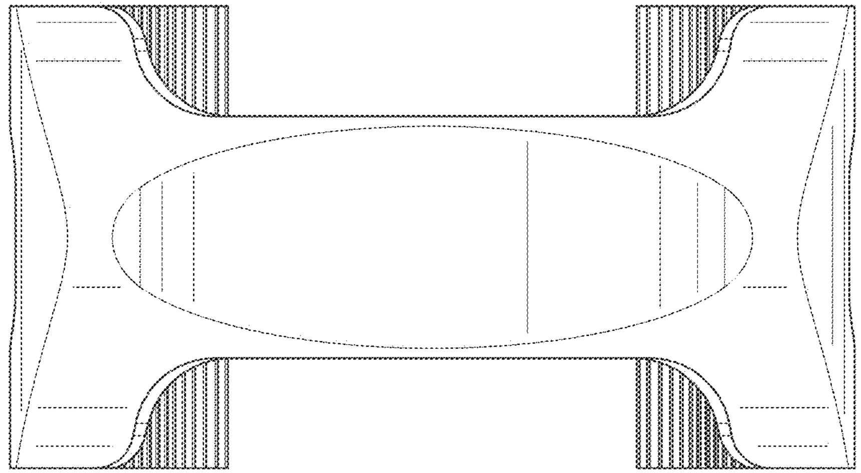
Figure 42:
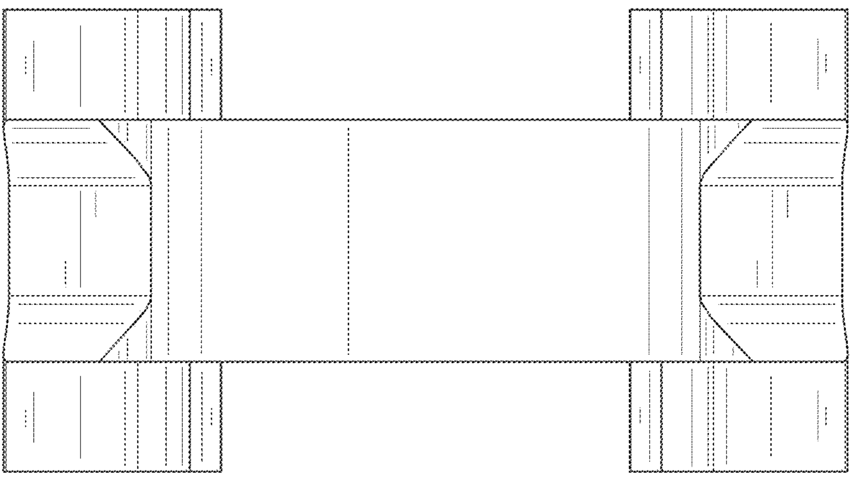
Figure 43:
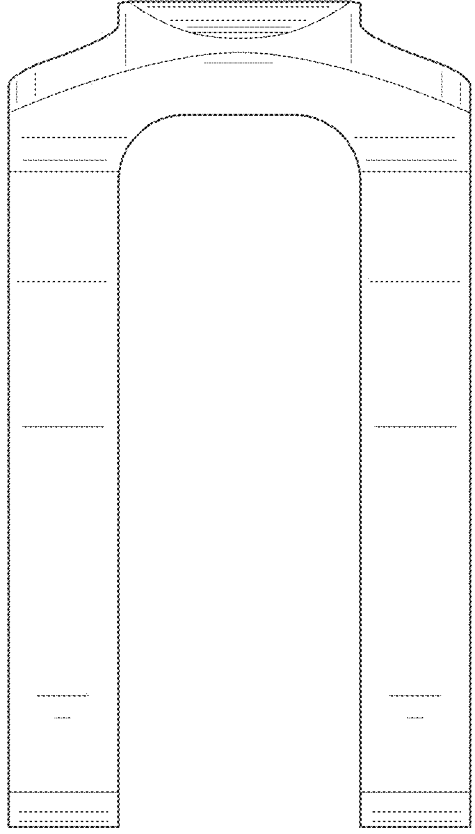
Figure 44:
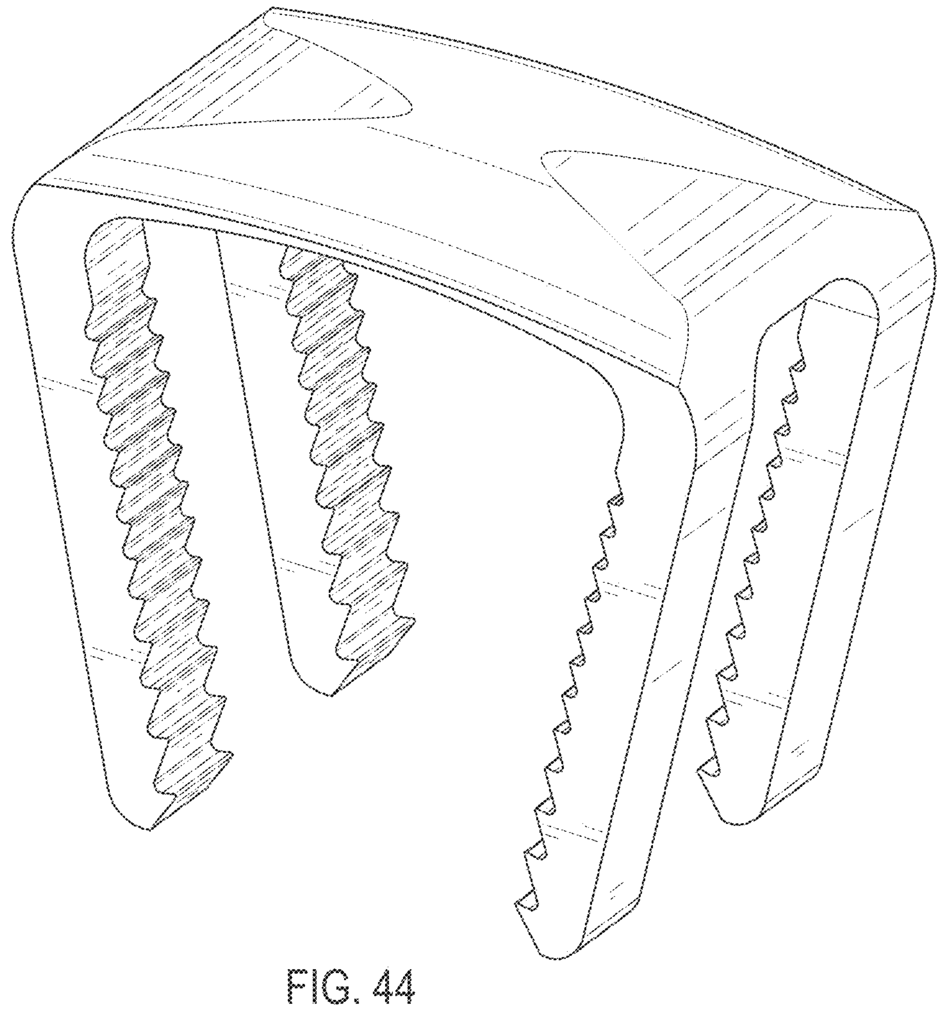
Figure 45:
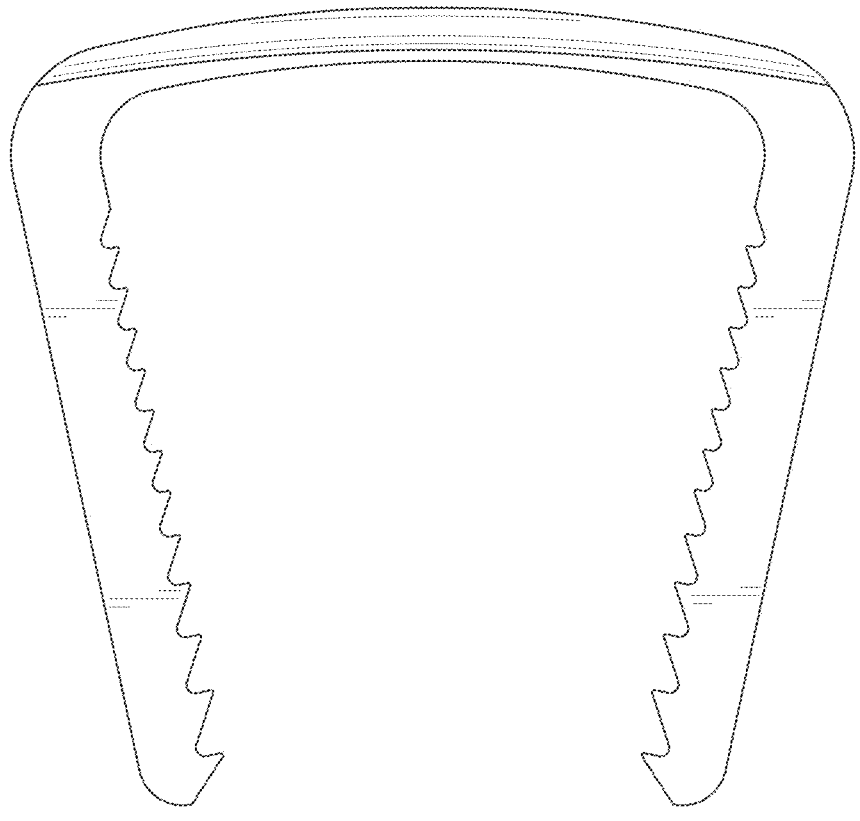
Figure 46:
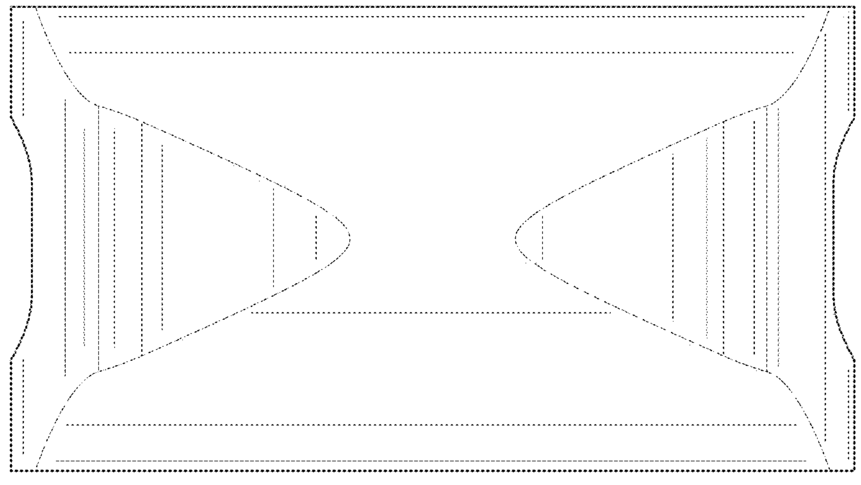
Figure 47:
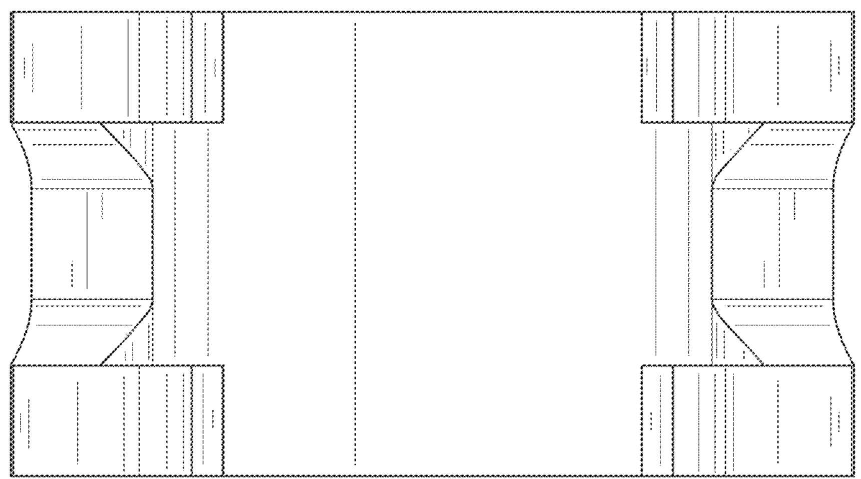
Figure 48:
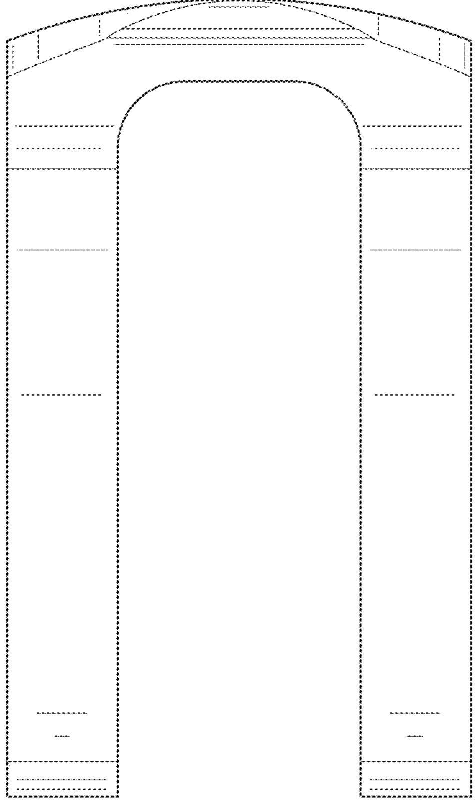
Figure 49:
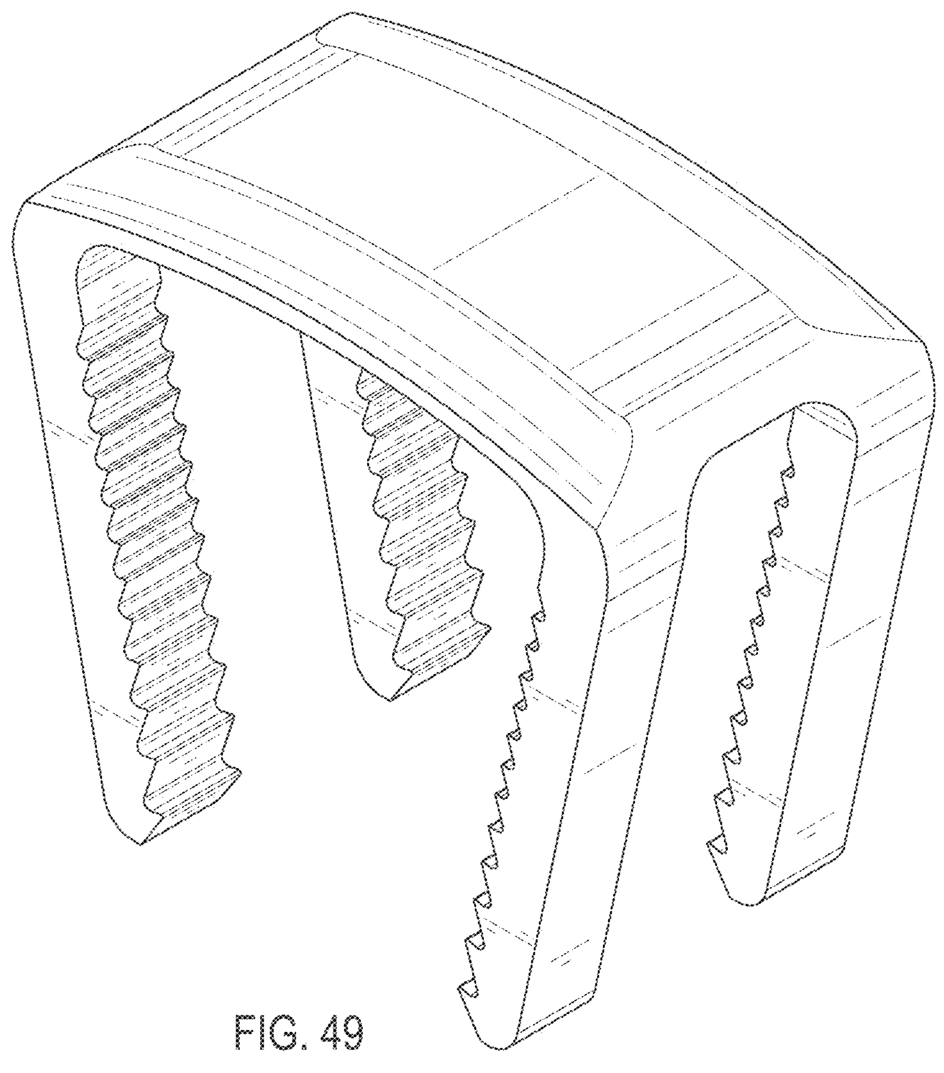
Figure 50:
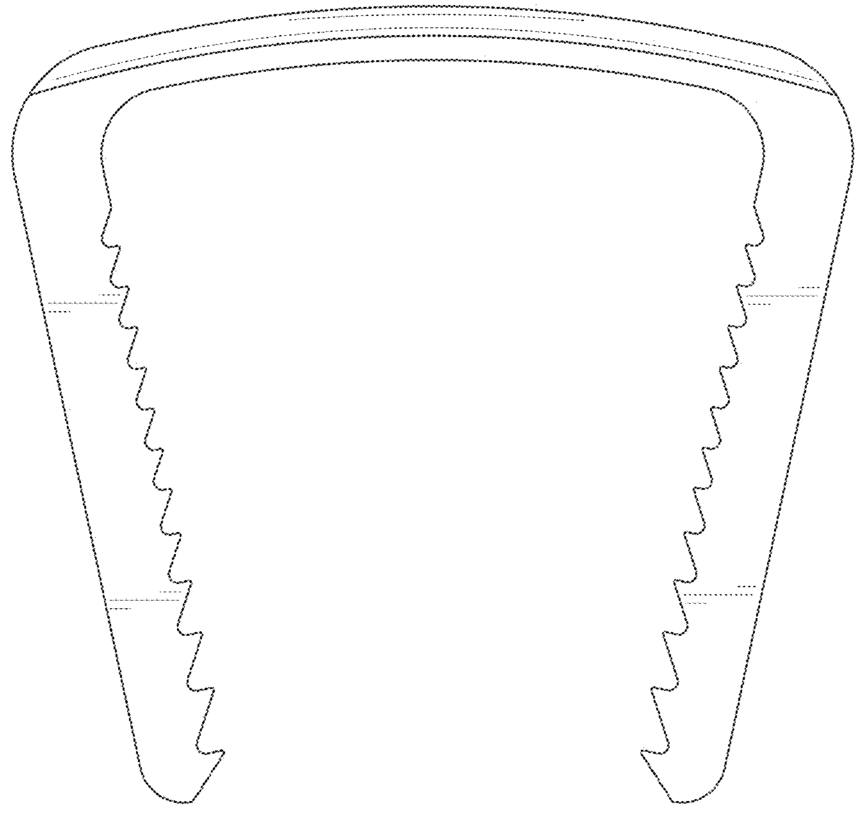
Figure 51:
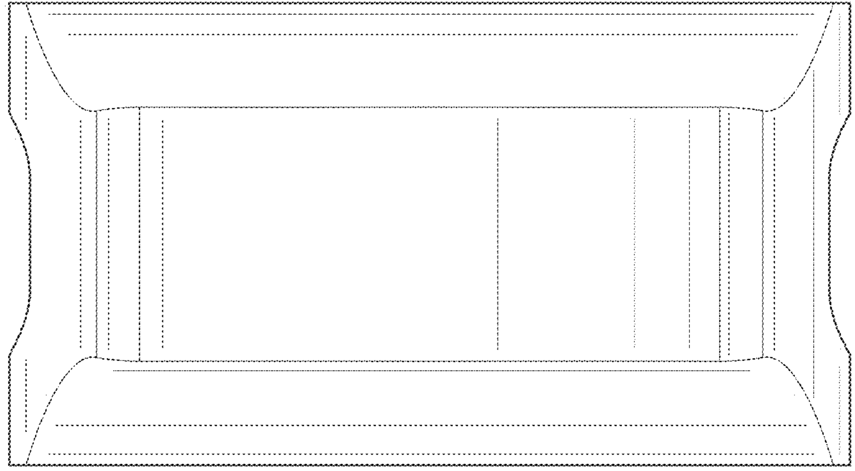
Figure 52:
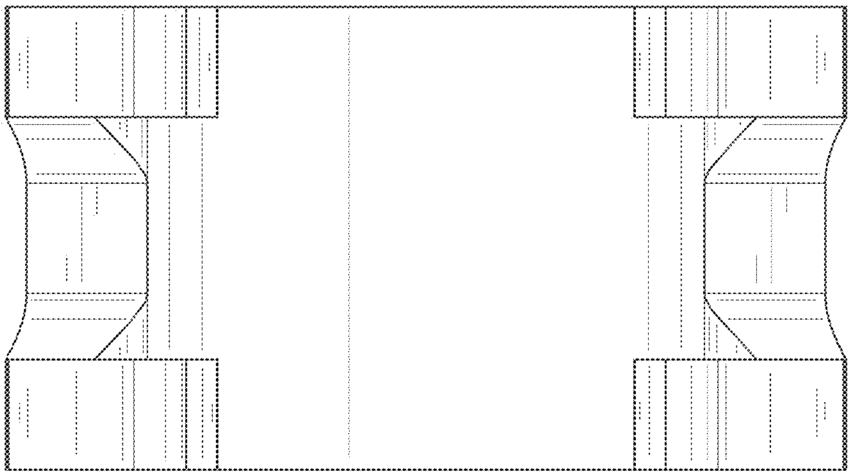
Figure 53:
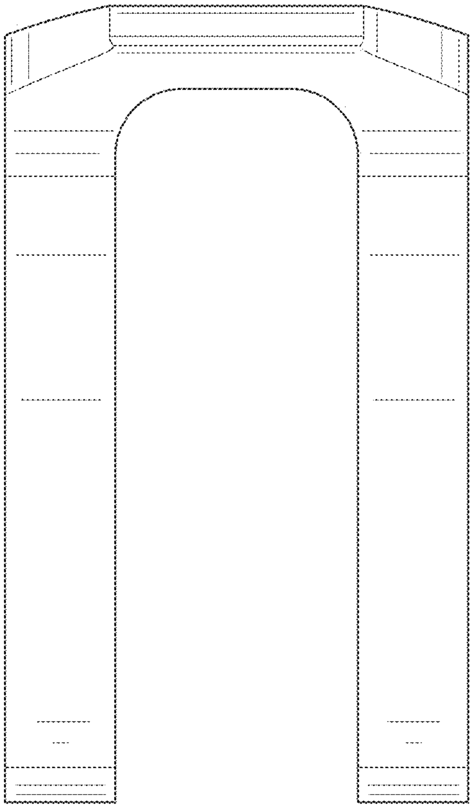
Figure 54:
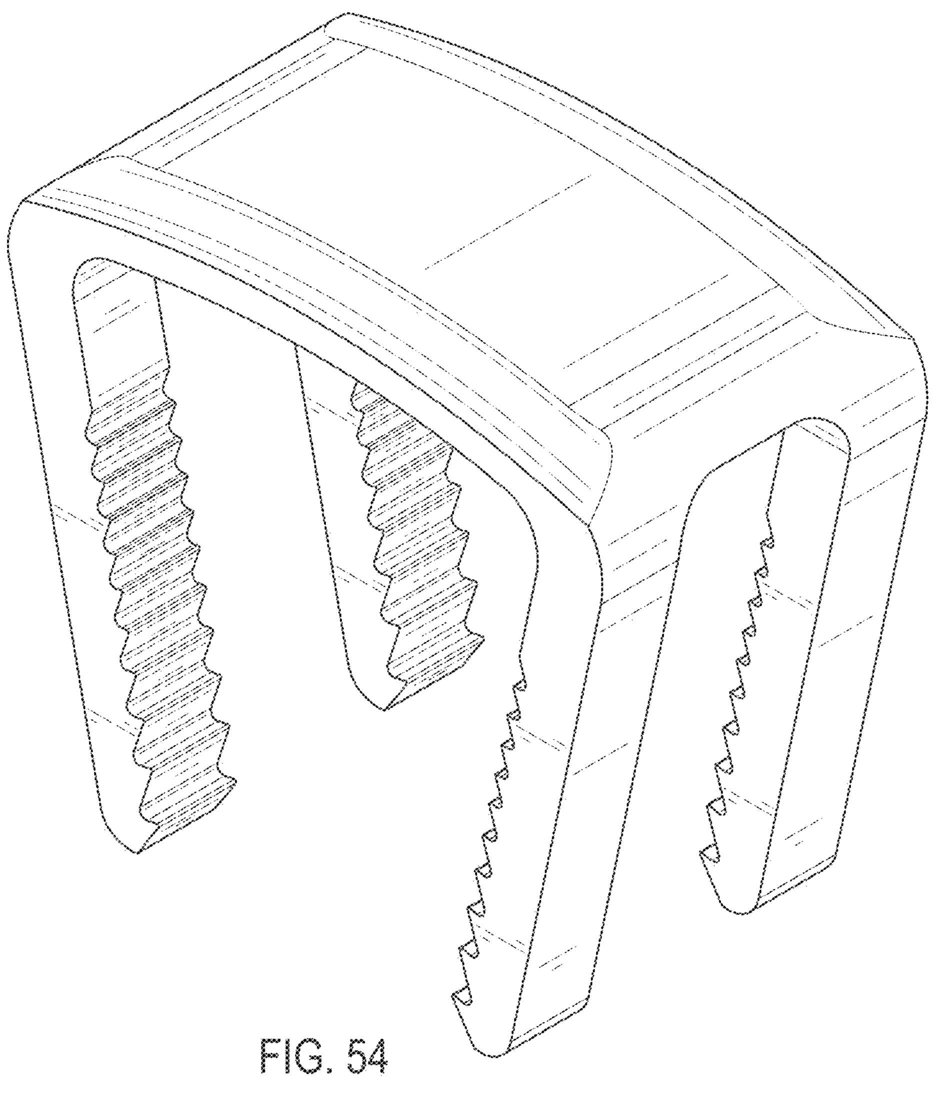
Figure 55:
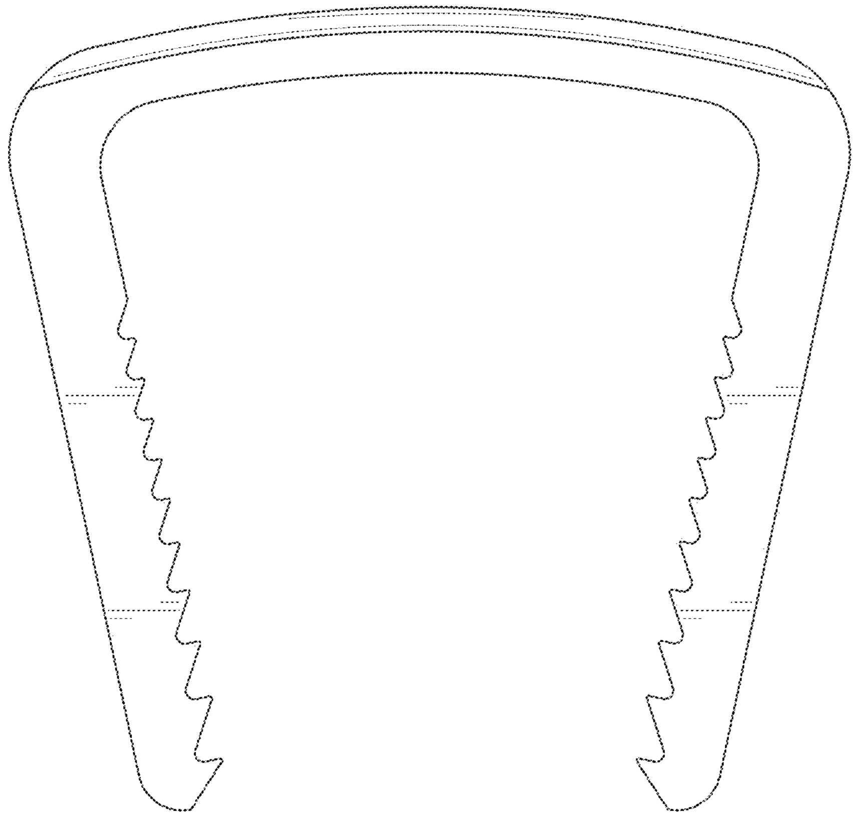
Figure 56:
Figure 57:
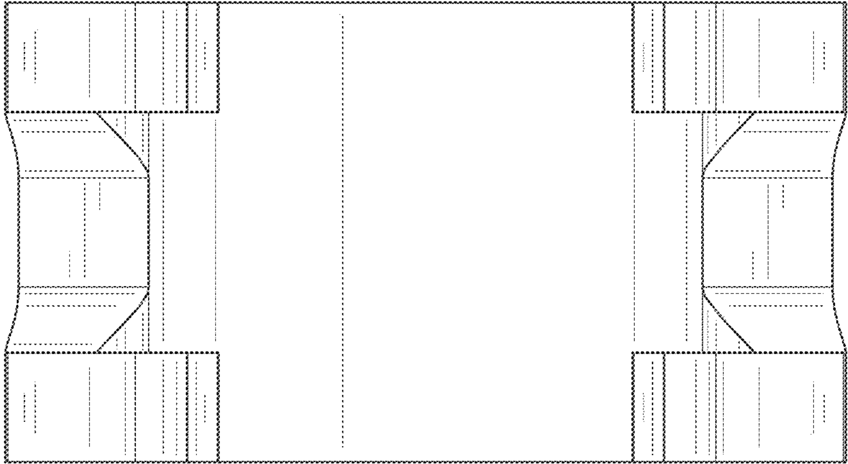
Figure 58:
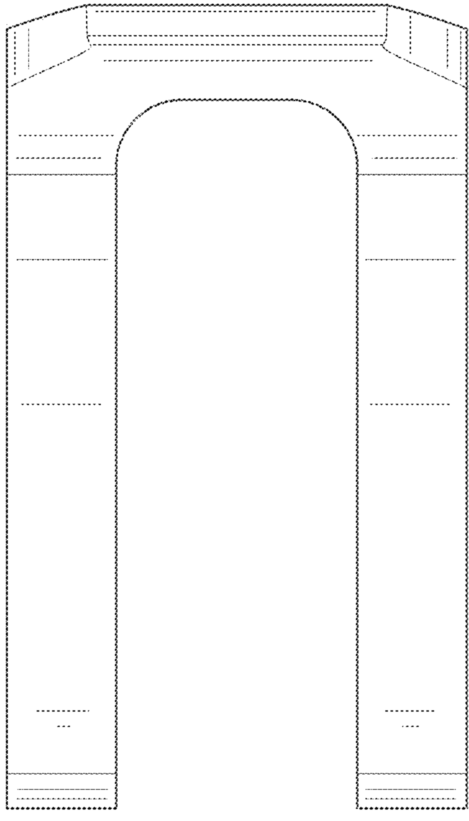
Figure 59:
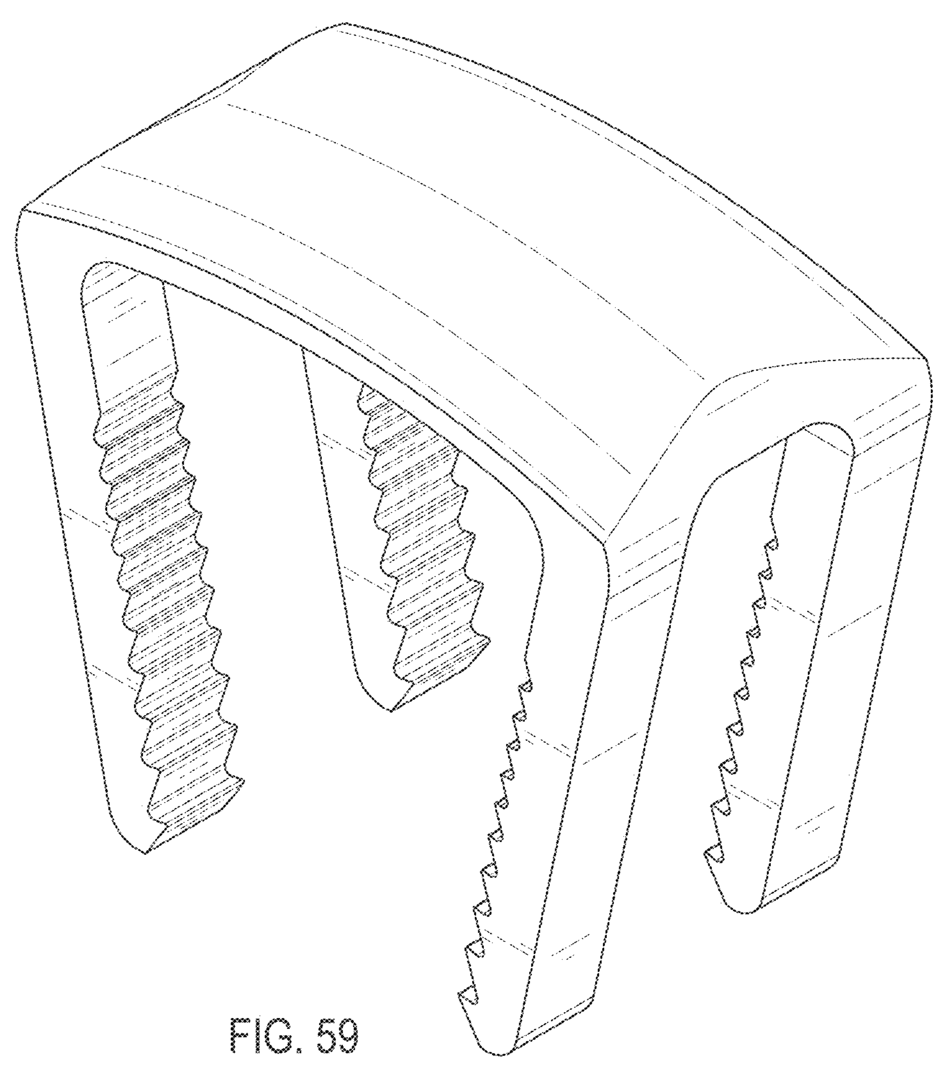
Figure 60:
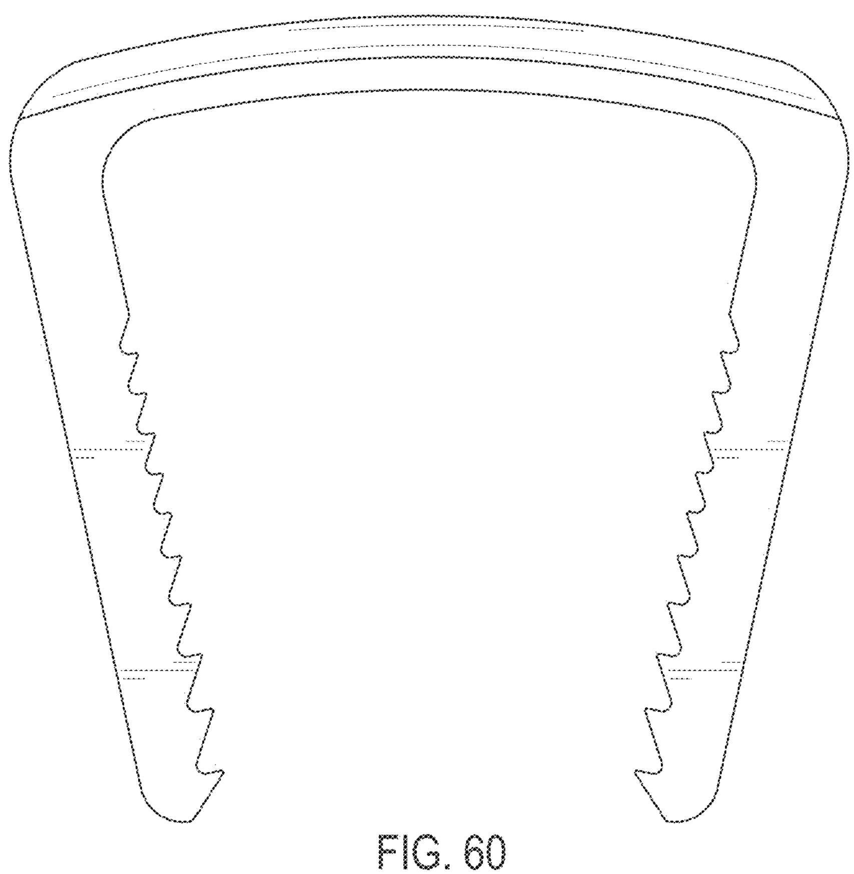
Figure 61:
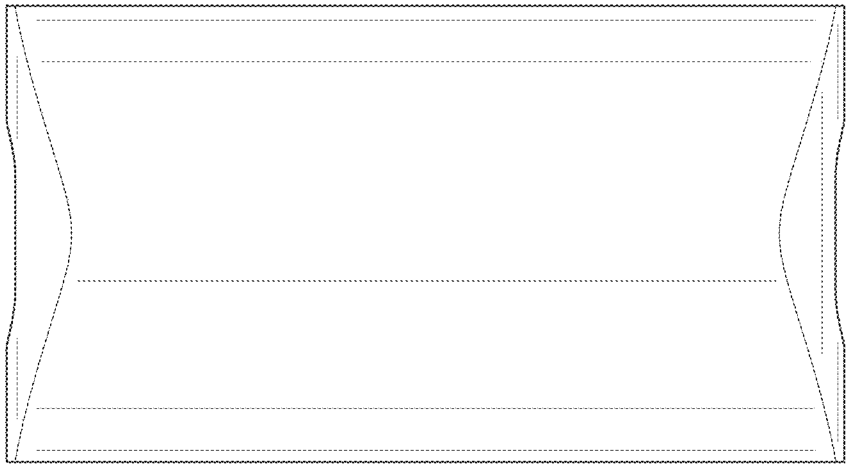
Figure 62:
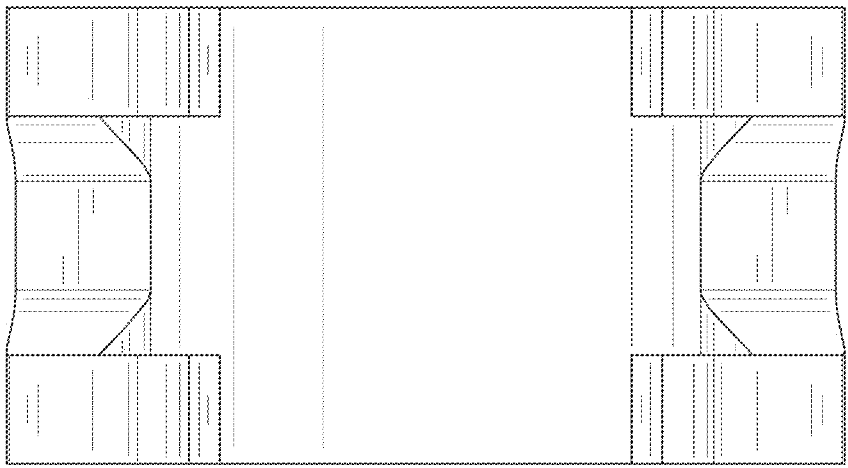
Figure 63:
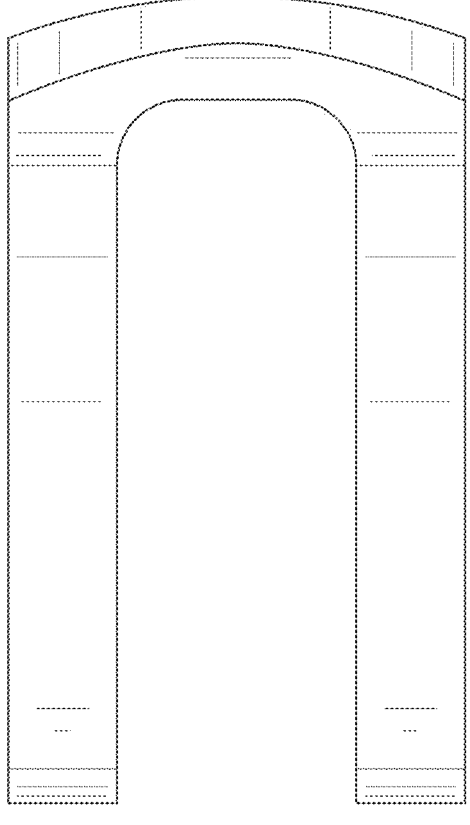
Figure 64:
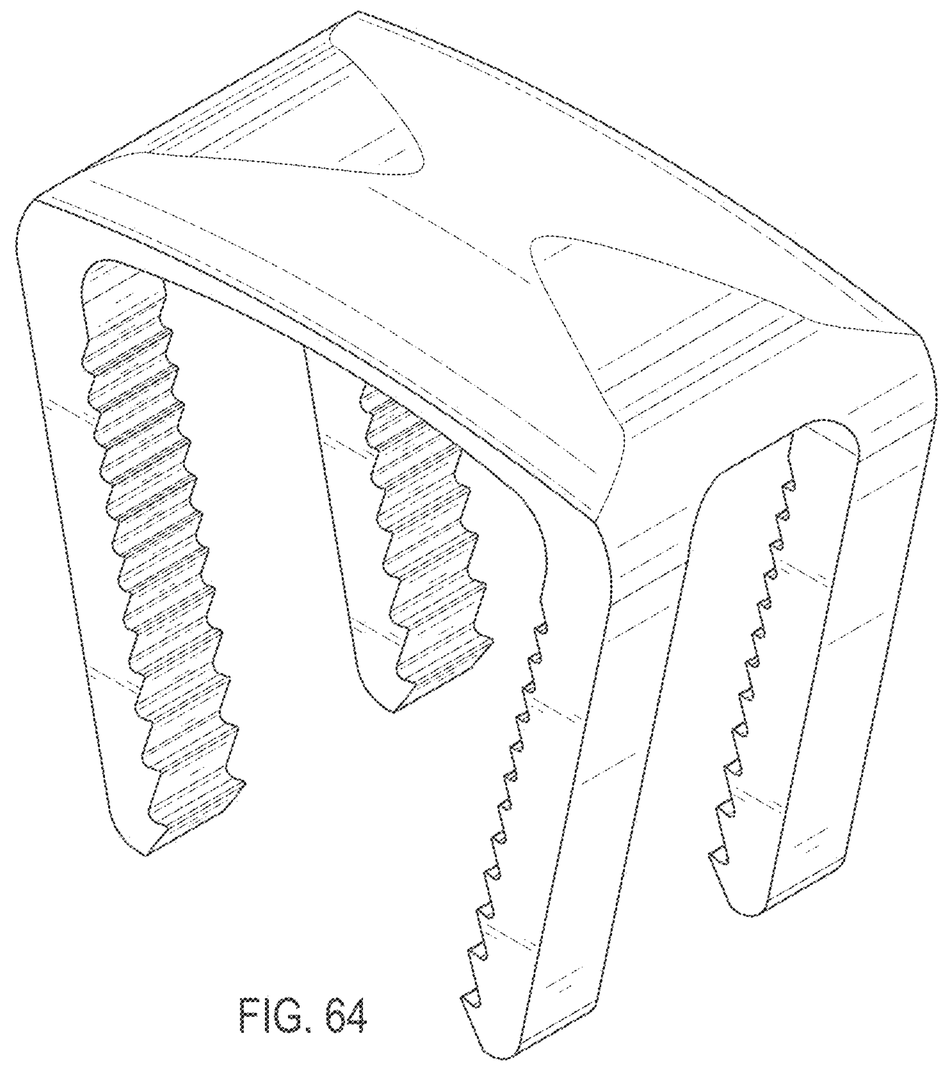
Figure 65:
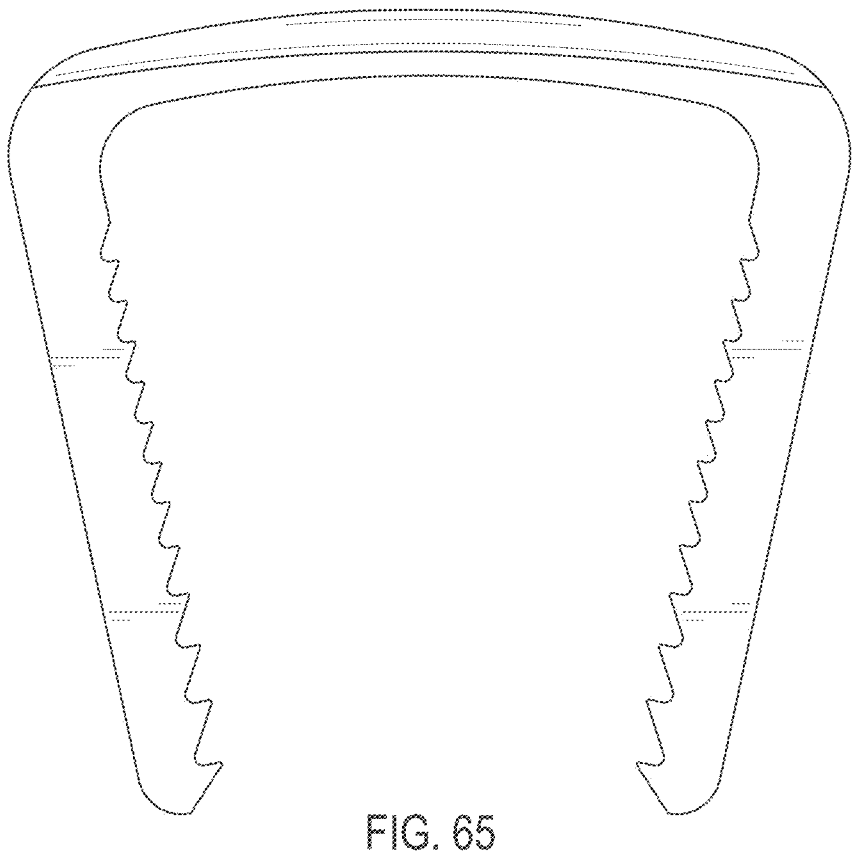
Figure 66:
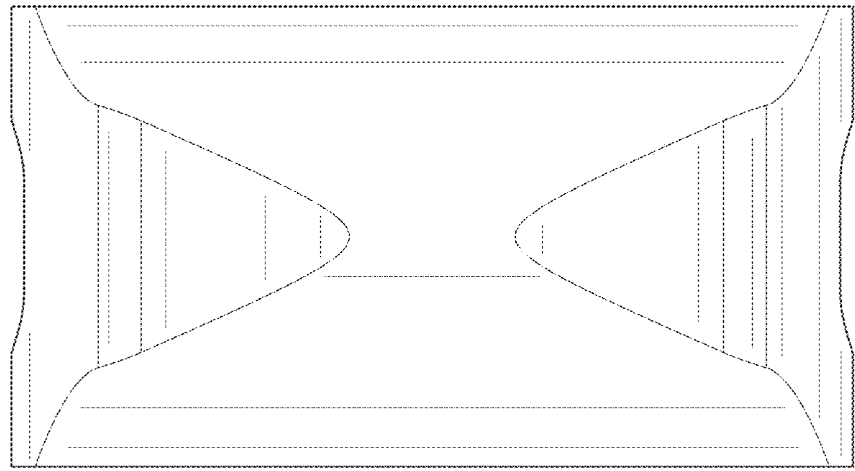
Figure 67:
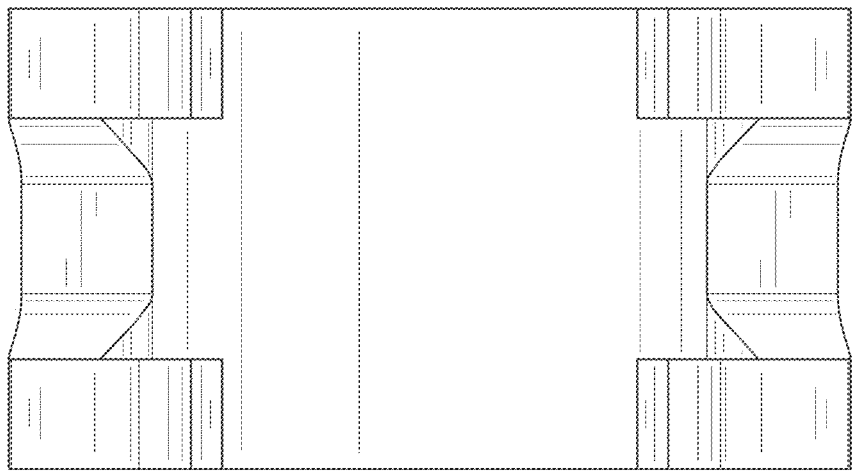
Figure 68:
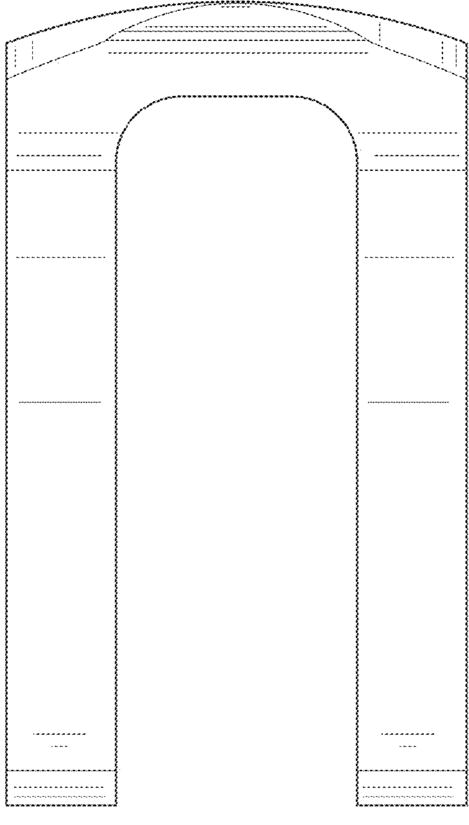
Figure 69:
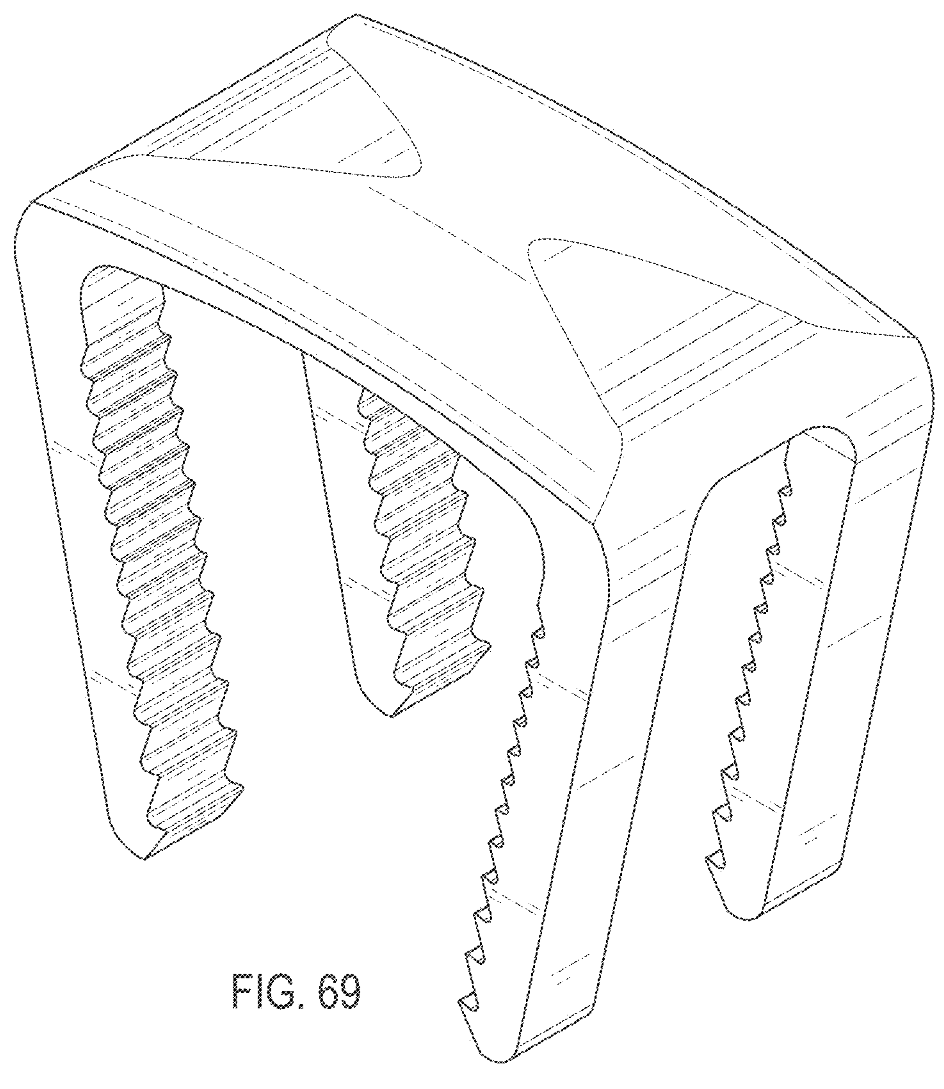
Figure 70:
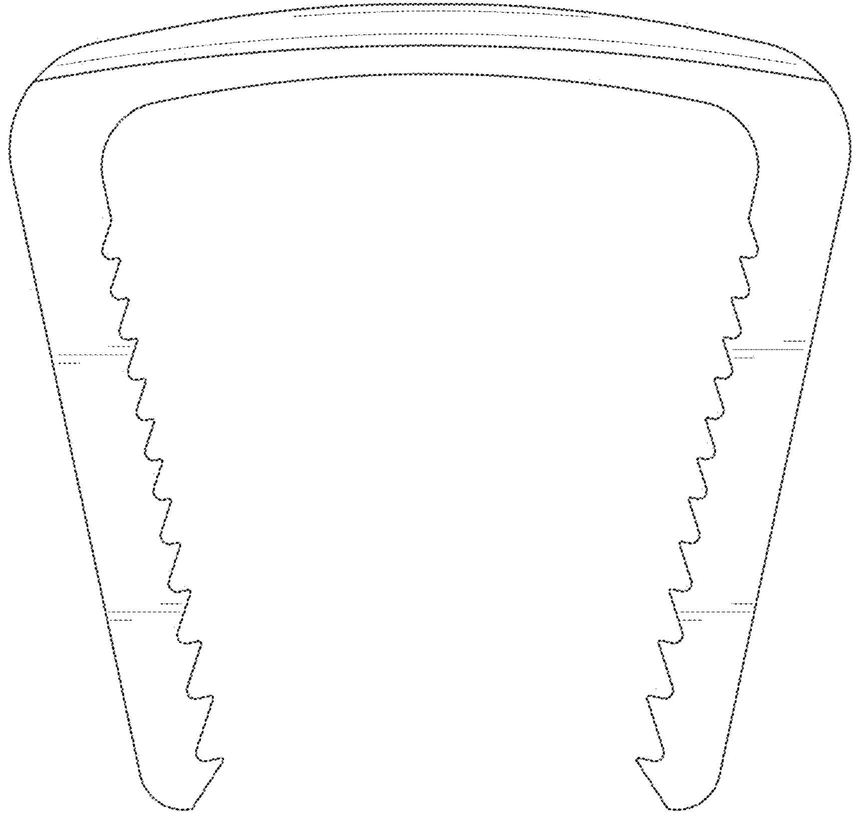
Figure 71:
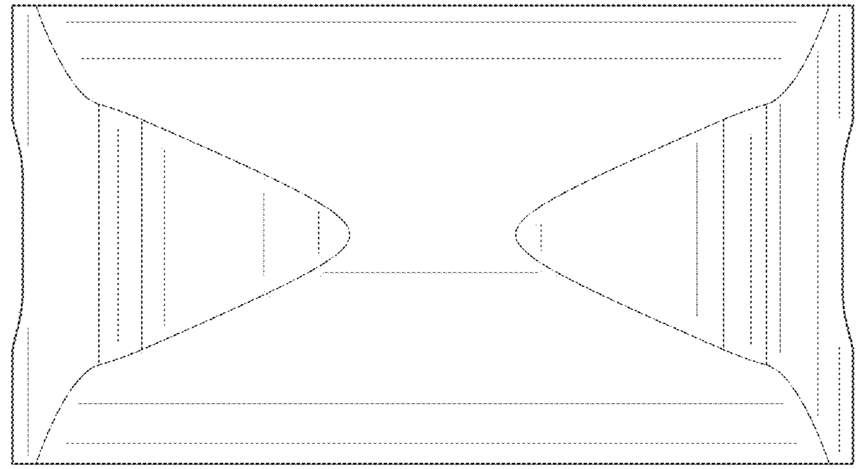
Figure 72:
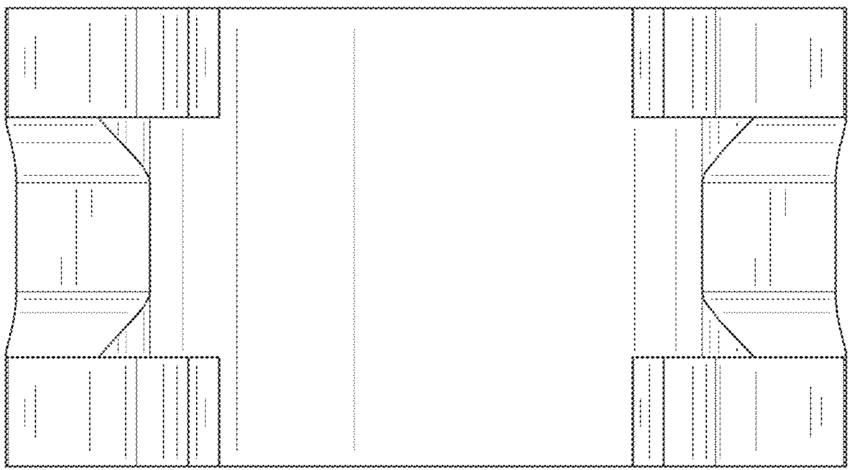
Figure 73:
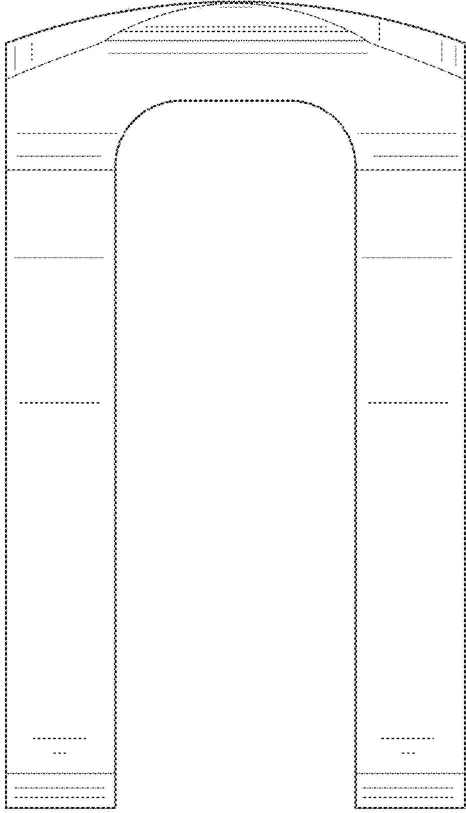
Figure 74:
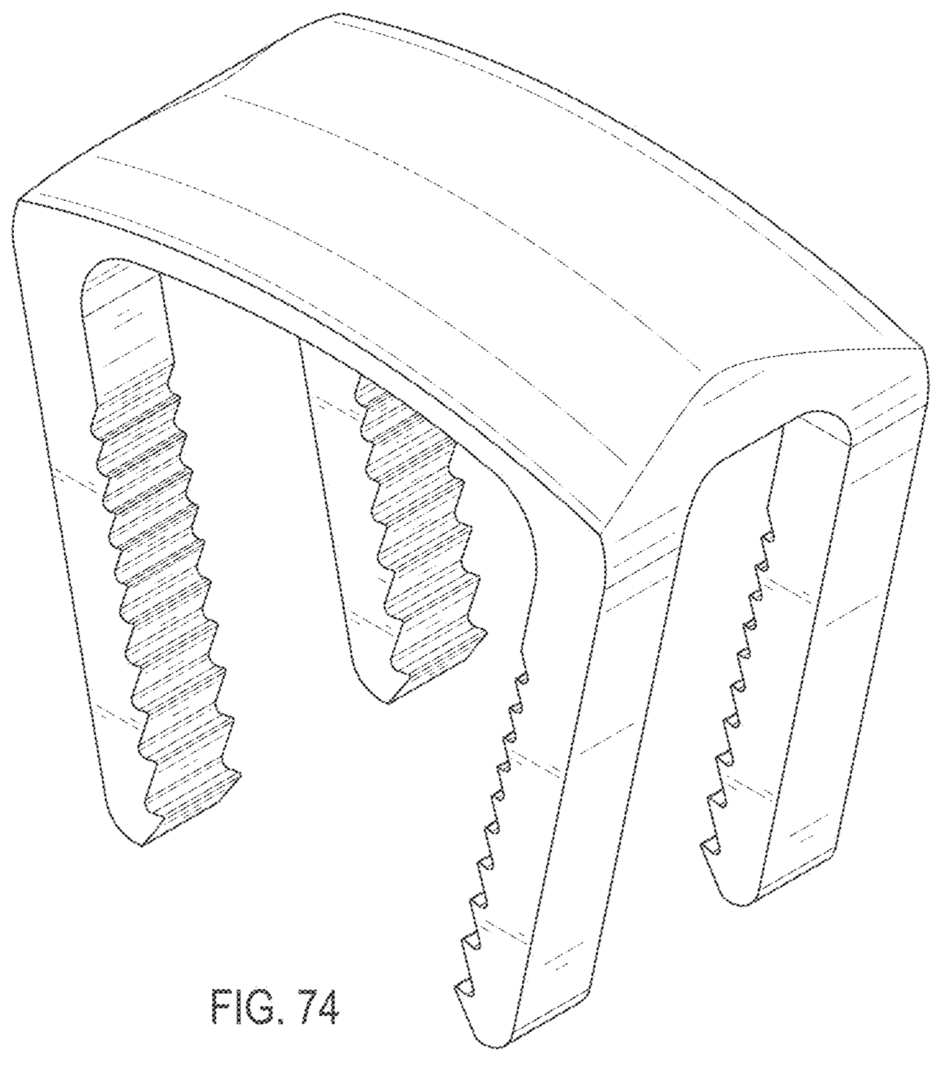
Figure 75:
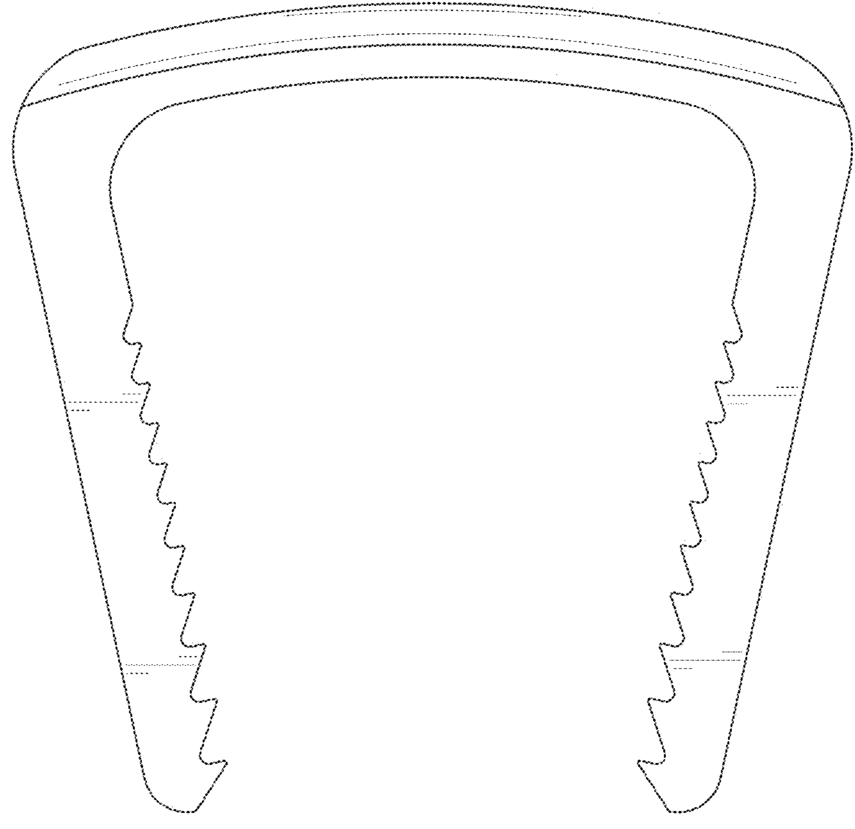
Figure 76:
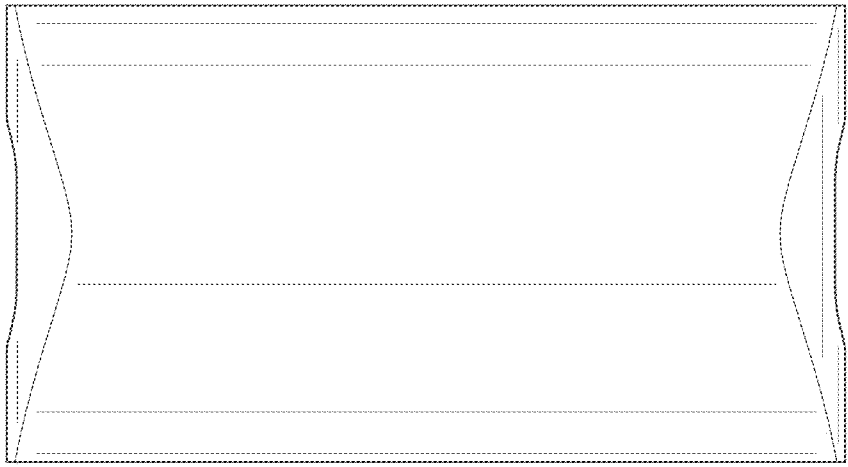
Figure 77:
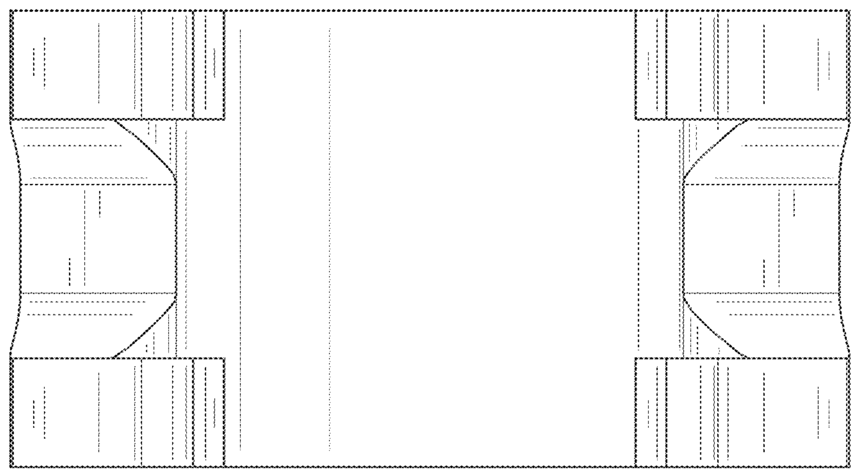
Figure 78:
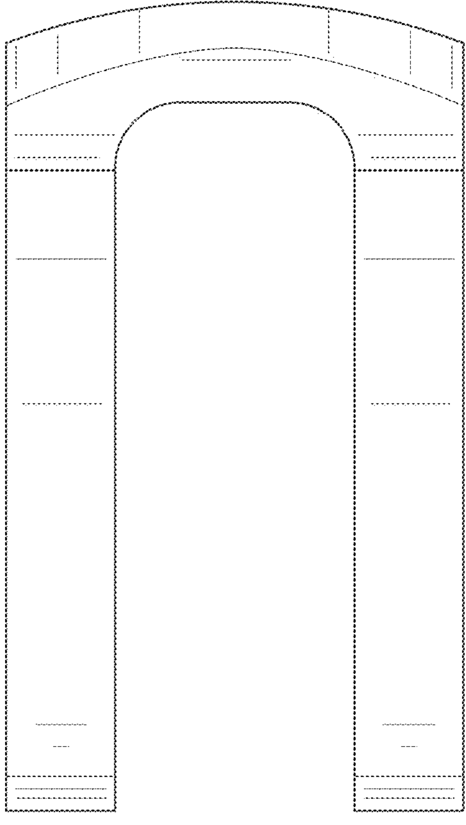
Figure 79:
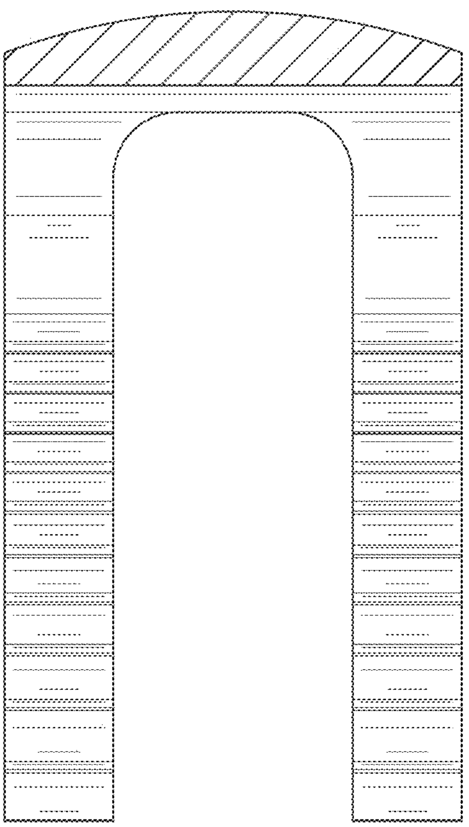
Figure 80:
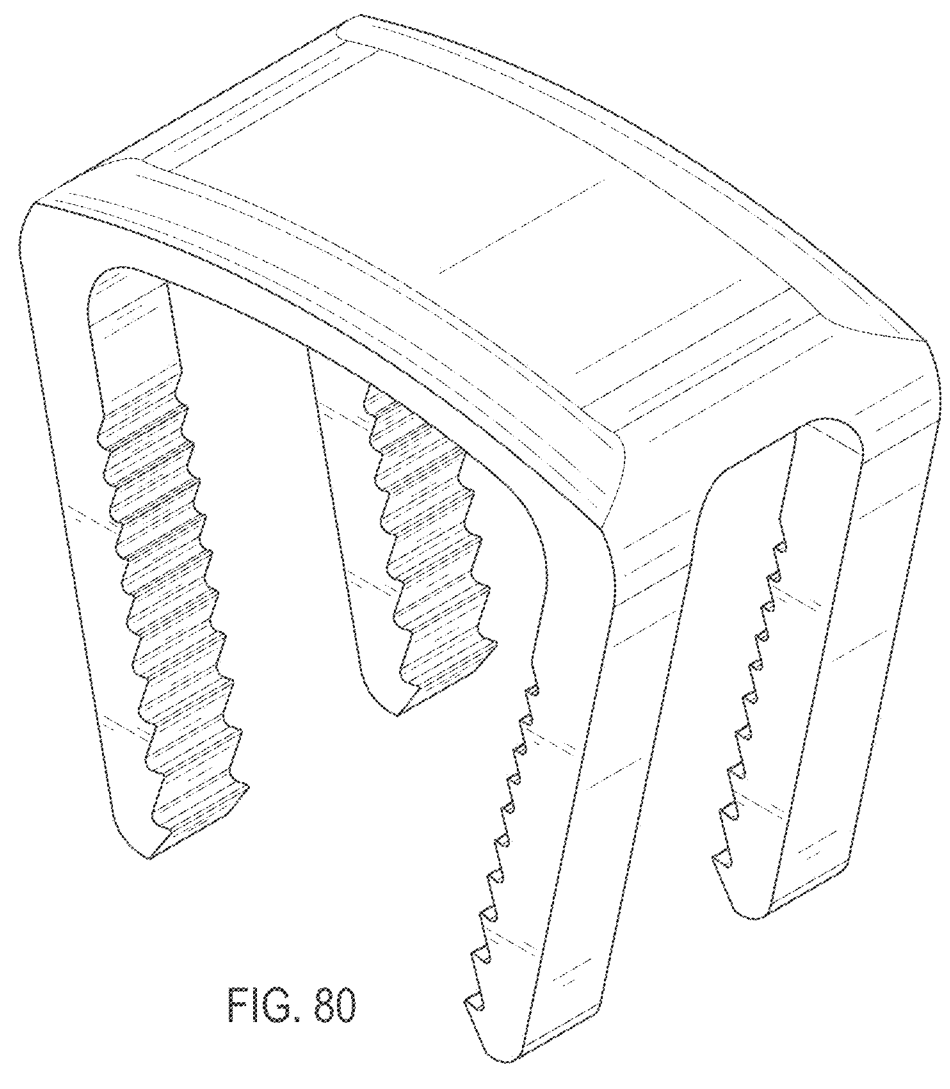
Figure 81:
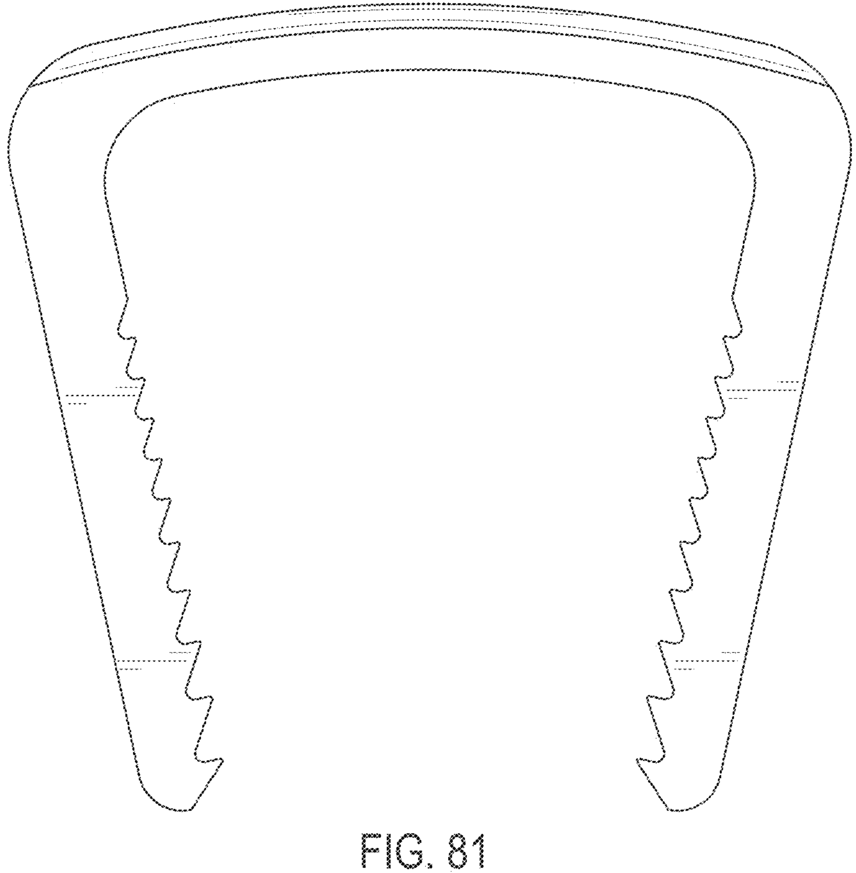
Figure 82:
Figure 83:
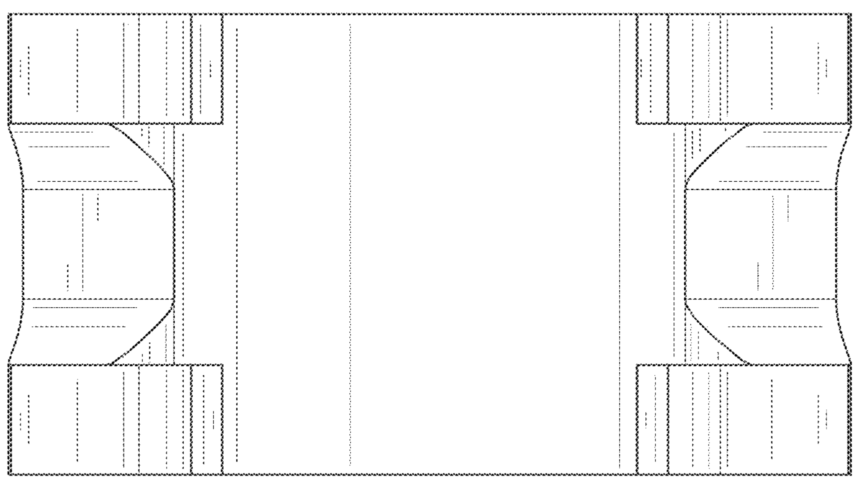
Figure 84:
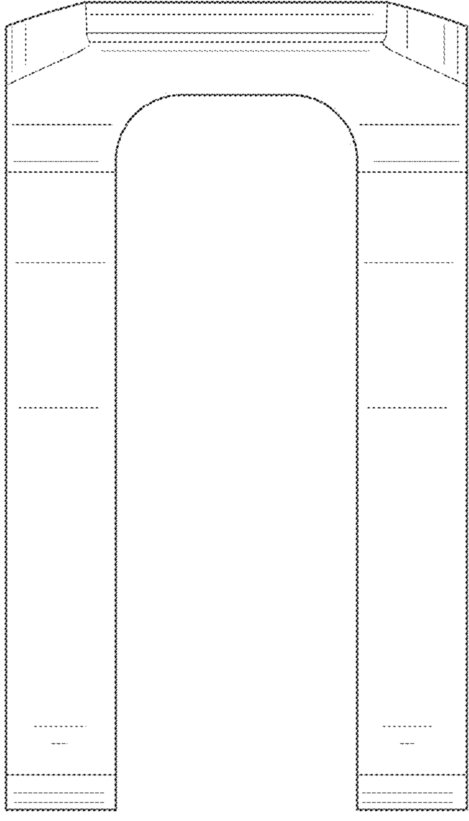
Figure 85:
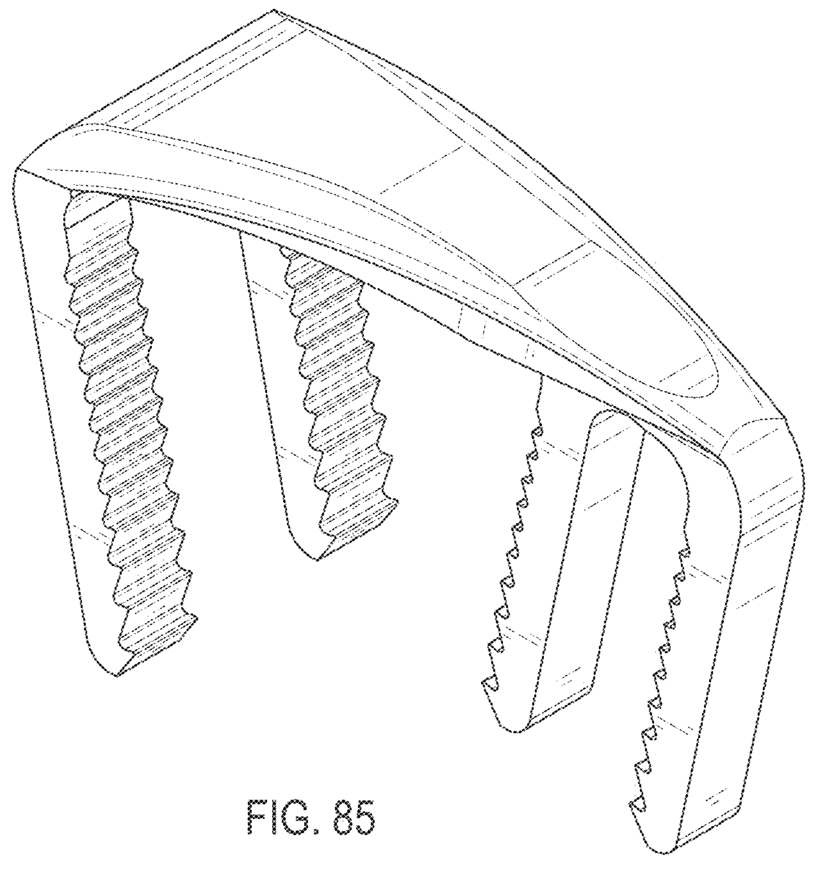
Figure 86:
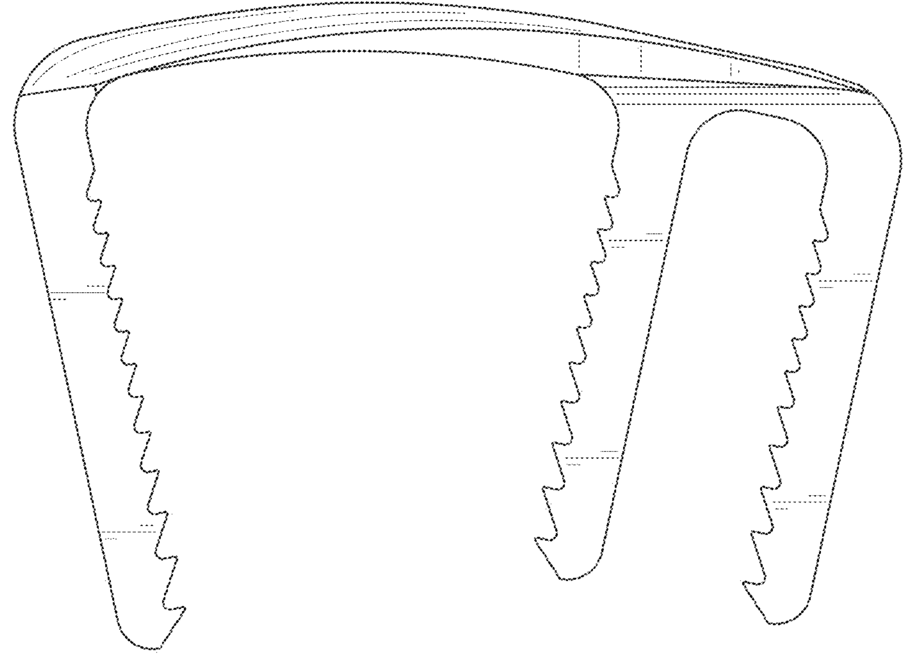
Figure 87:
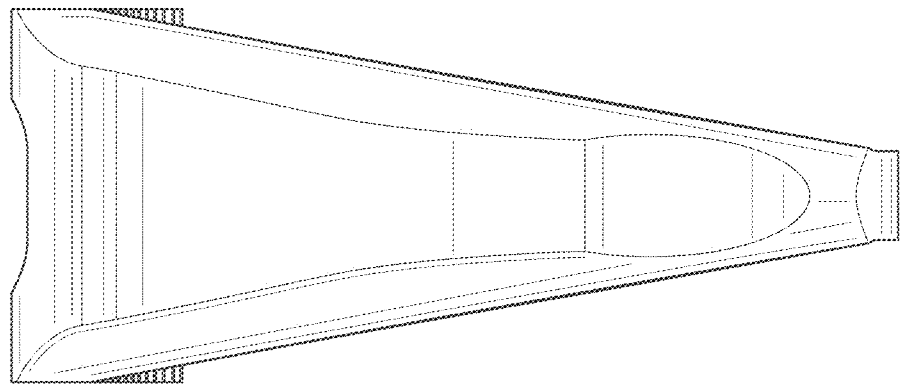
Figure 88:
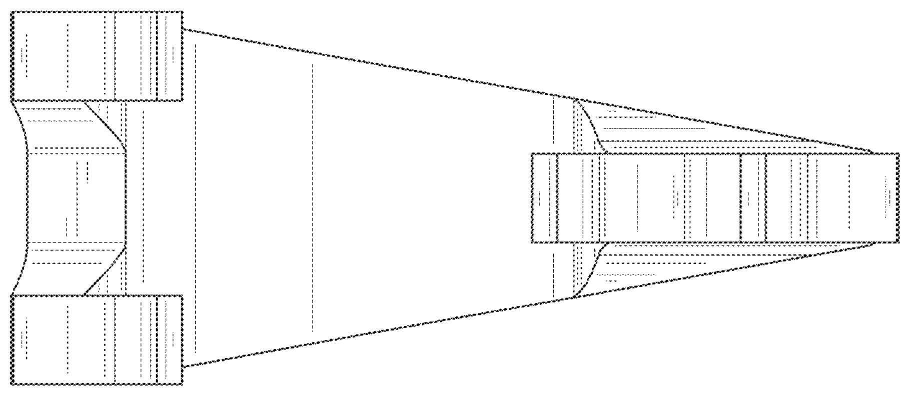
Figure 89:
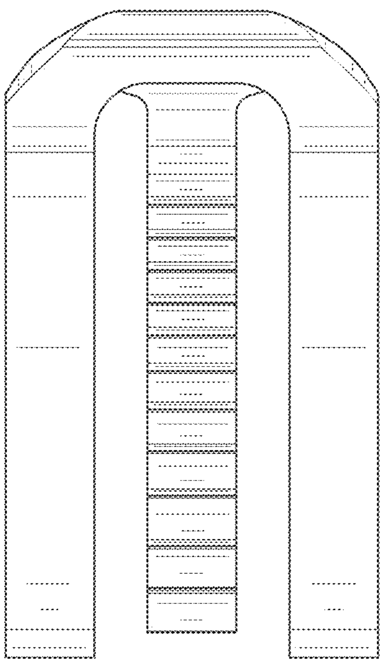
Figure 90:
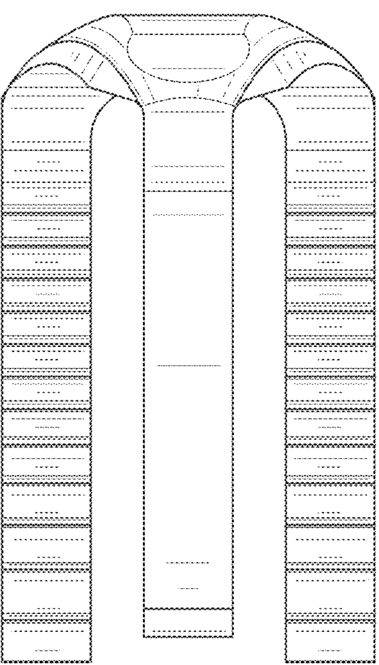
Figure 91:
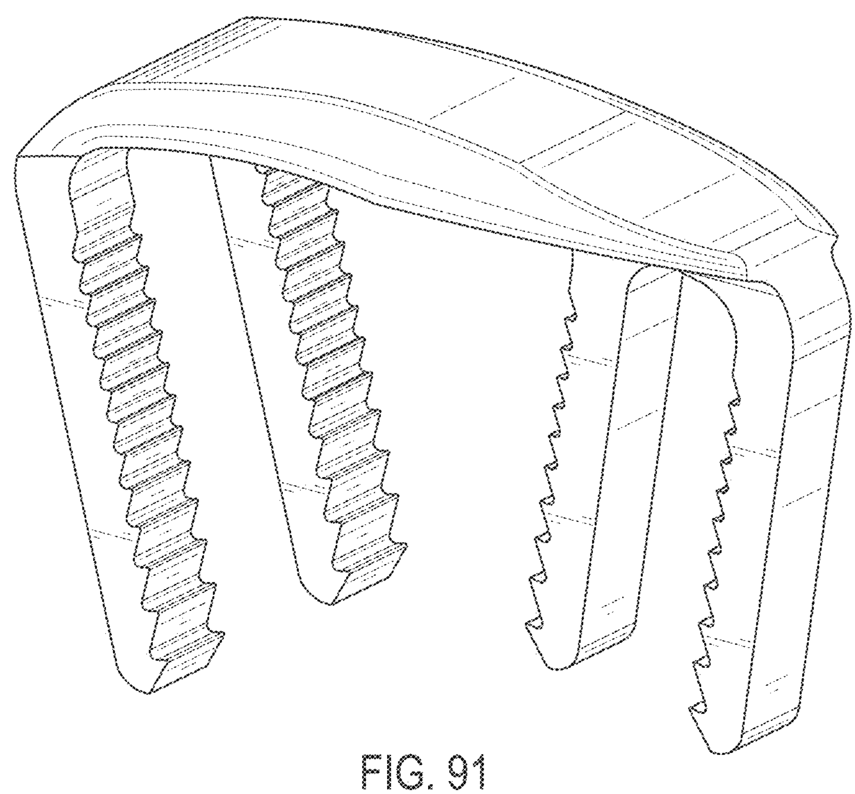
Figure 92:
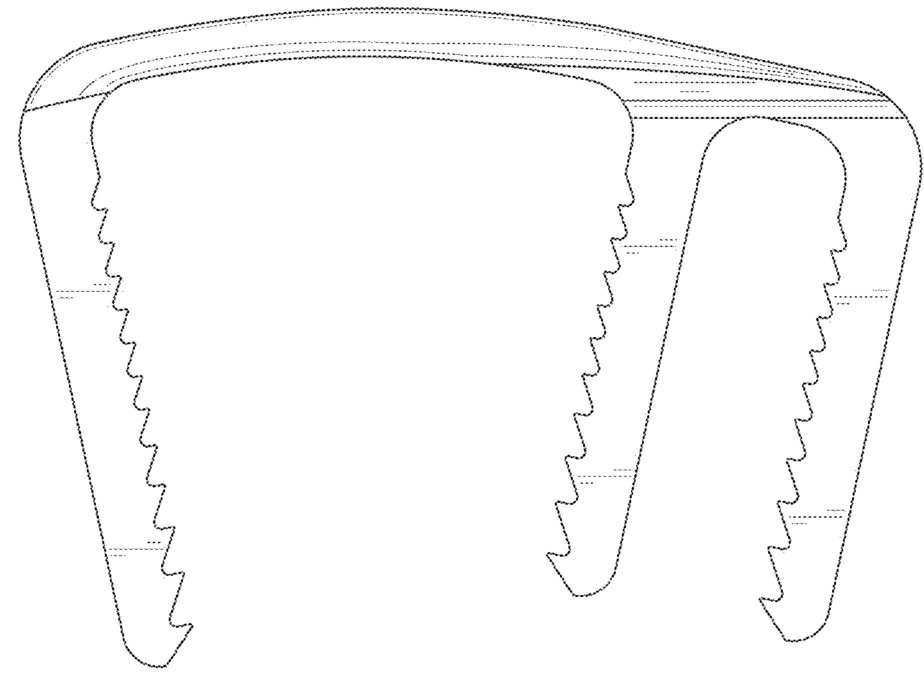
Figure 93:
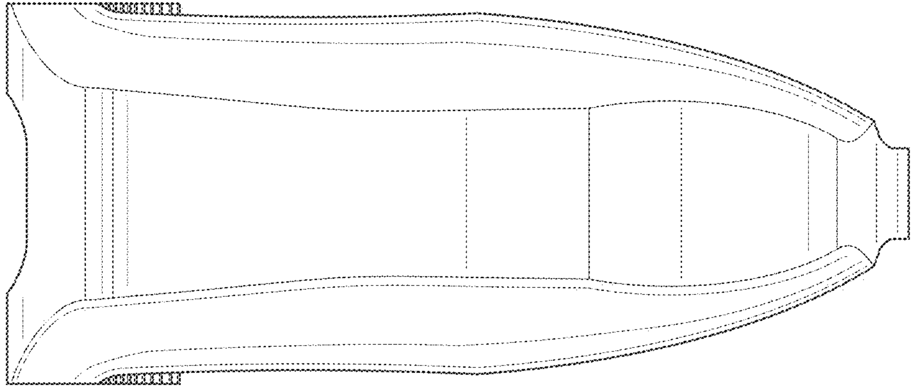
Figure 94:
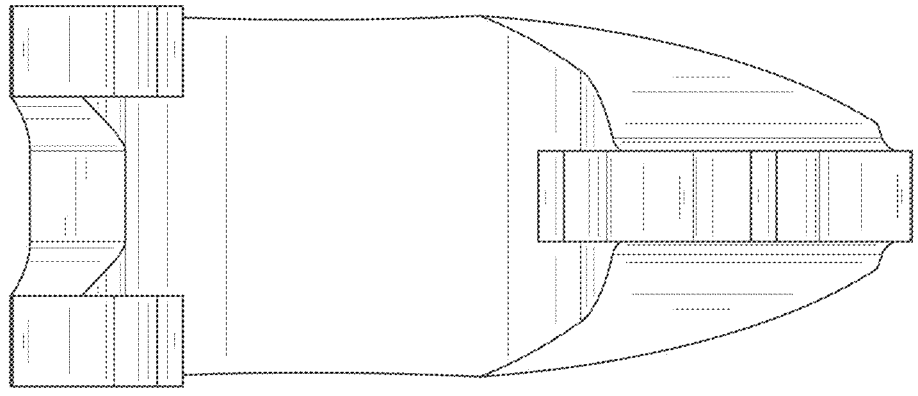
Figure 95:
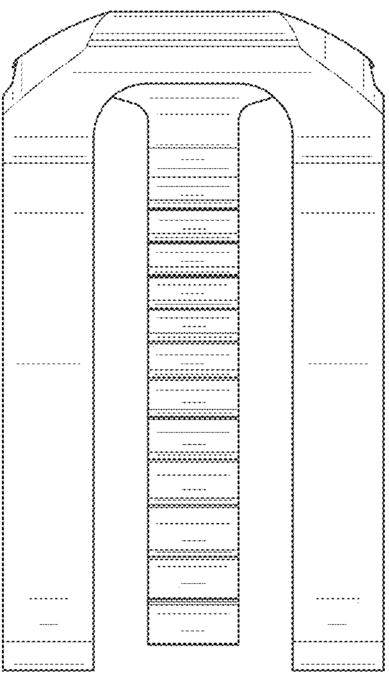
Figure 96:
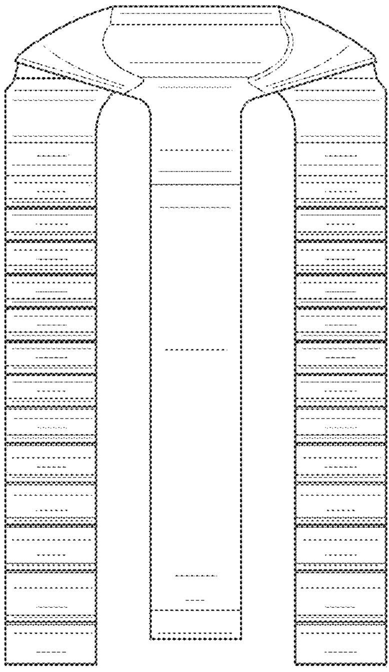
Figure 97:
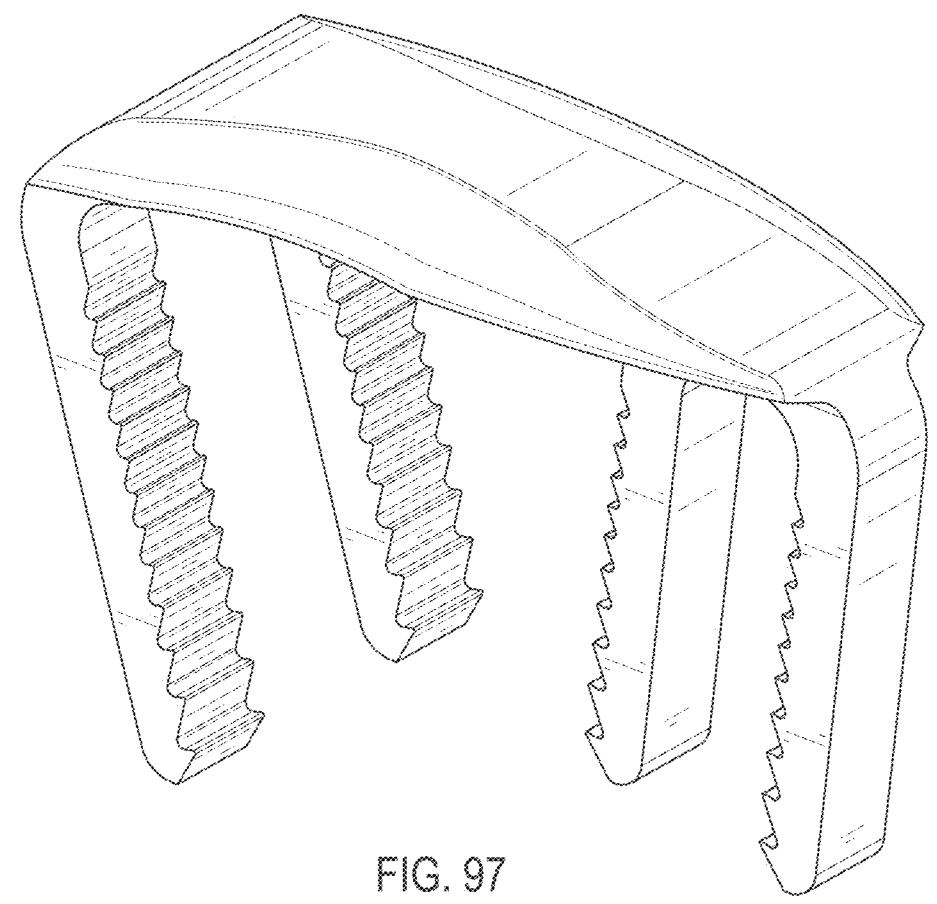
Figure 98:
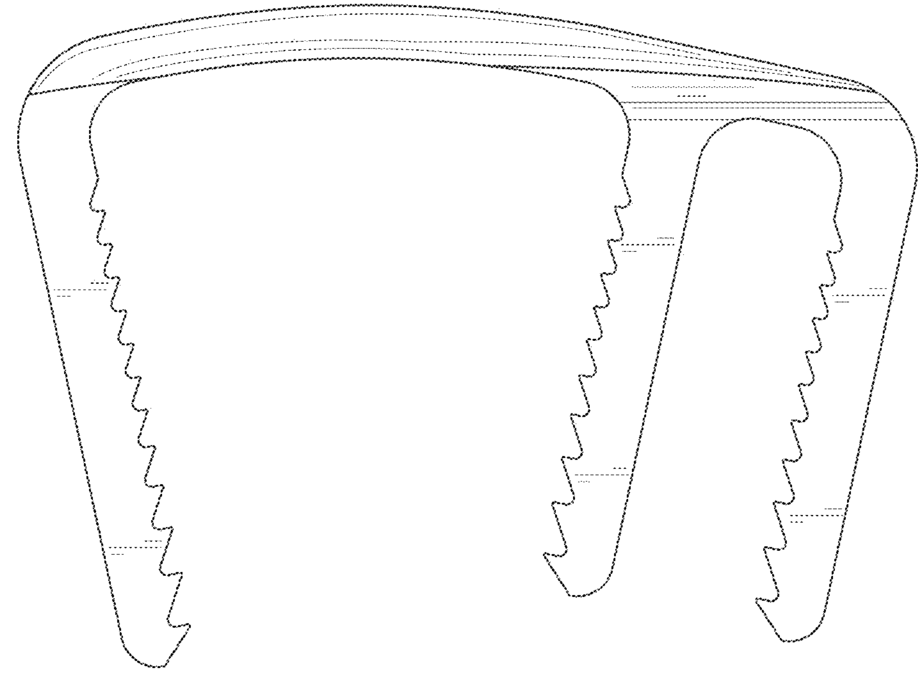
Figure 99:
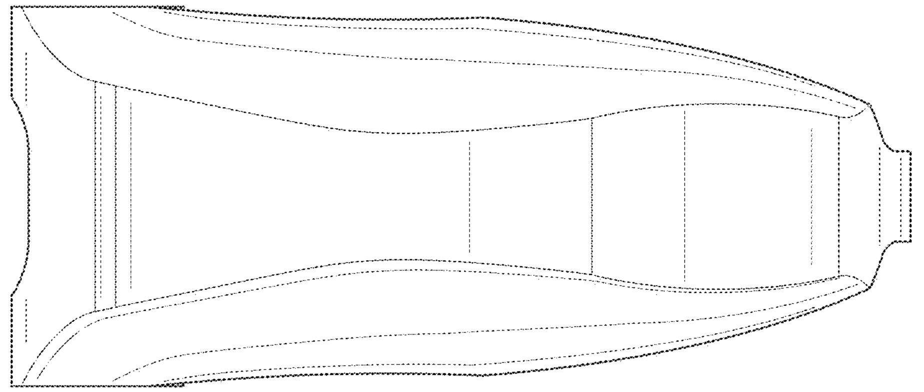
Figure 100:
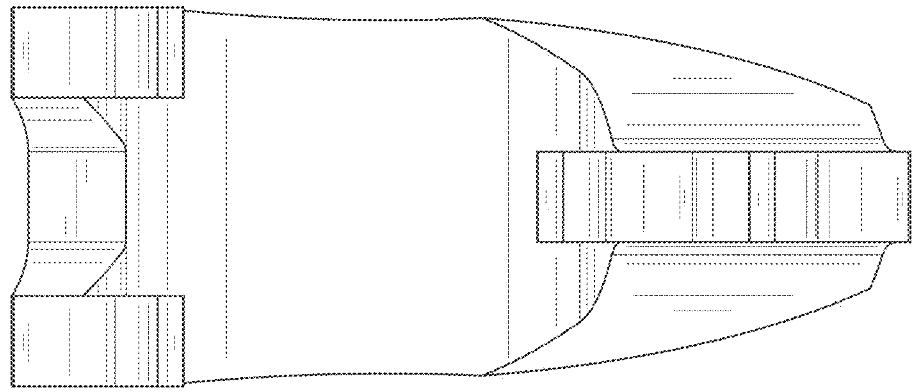
Figure 101:
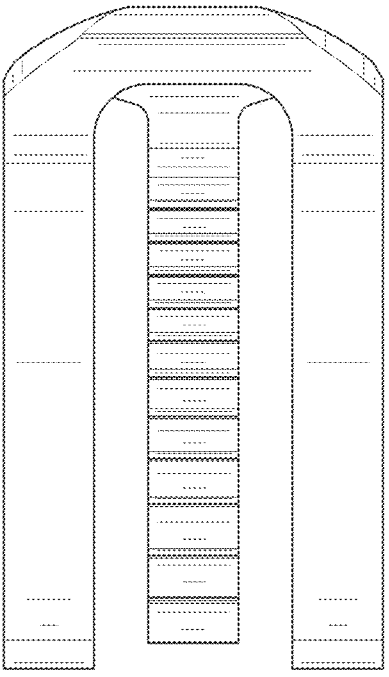
Figure 102:
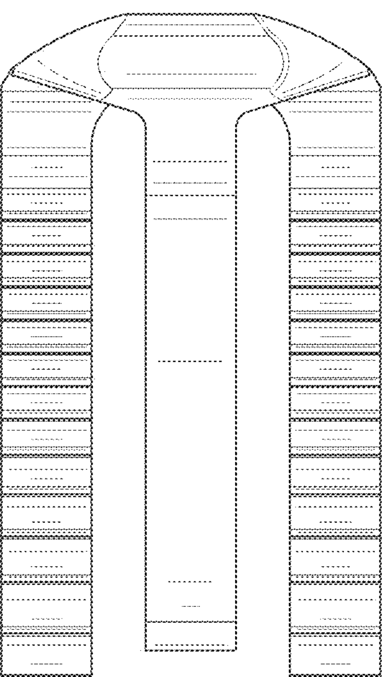
Figure 103:
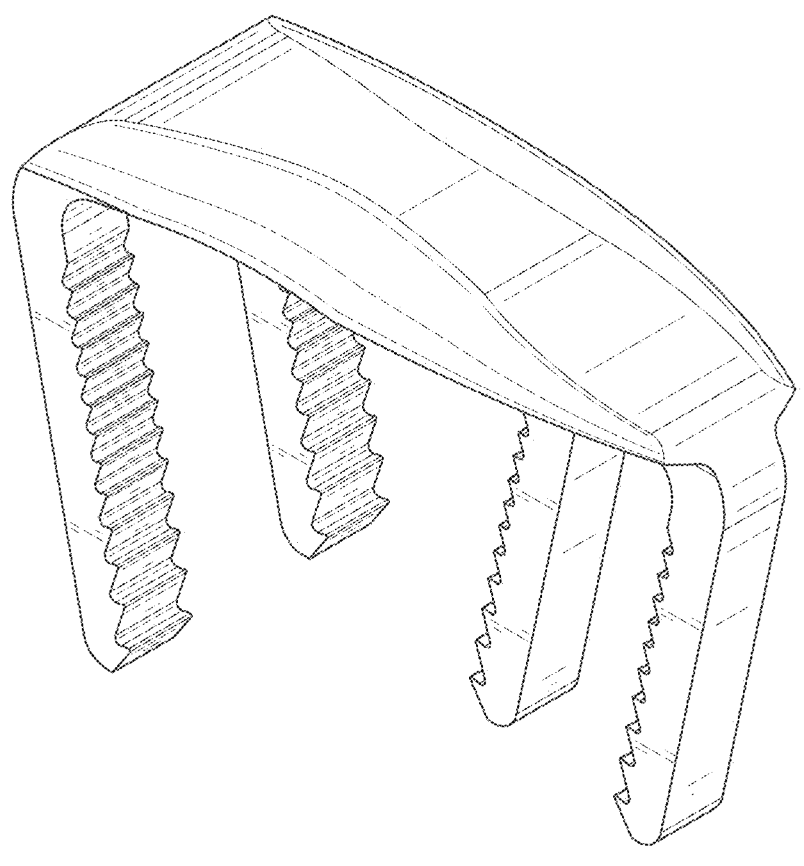
Figure 104:
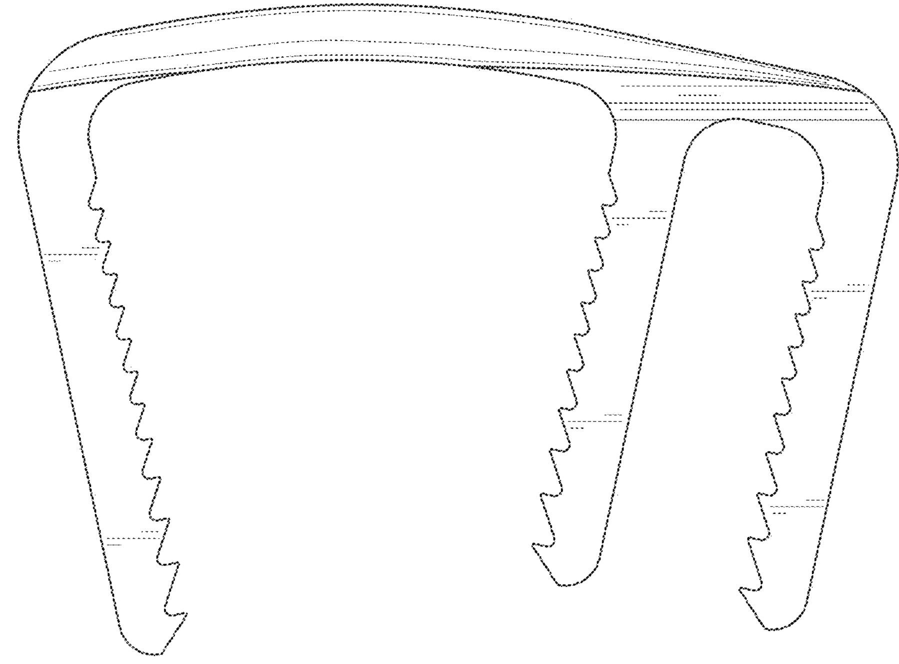
Figure 105:
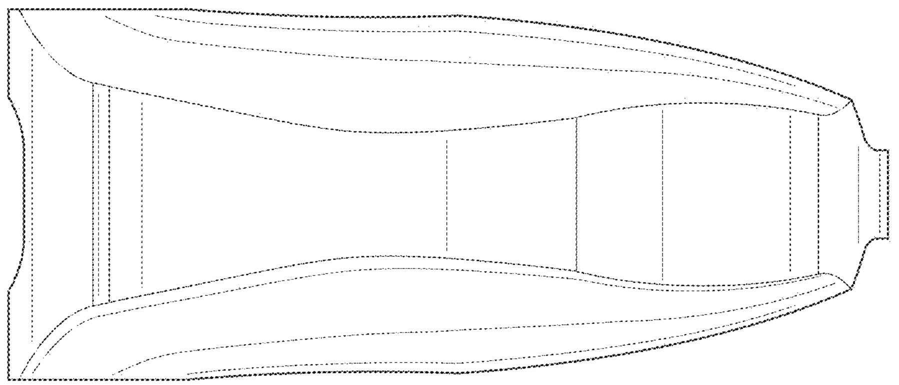
Figure 106:
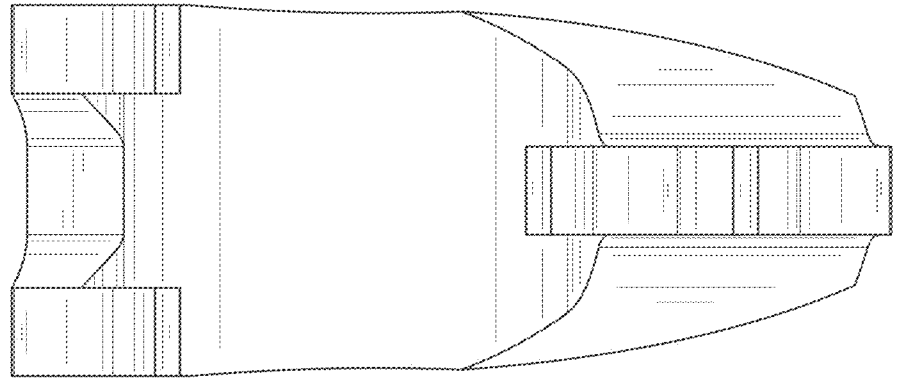
Figure 107:
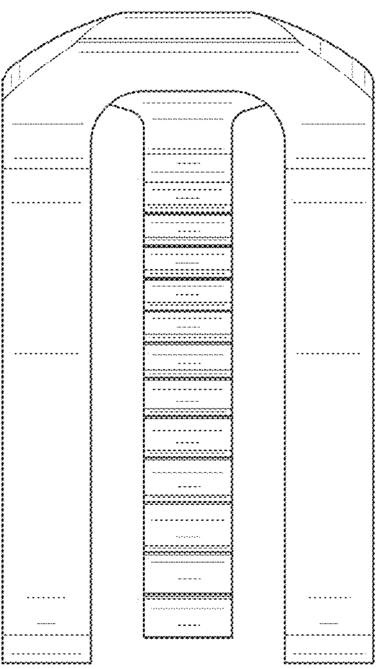
Figure 108:
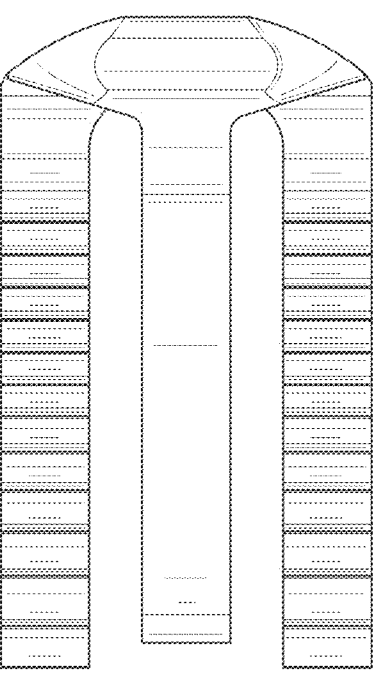
Figure 109:
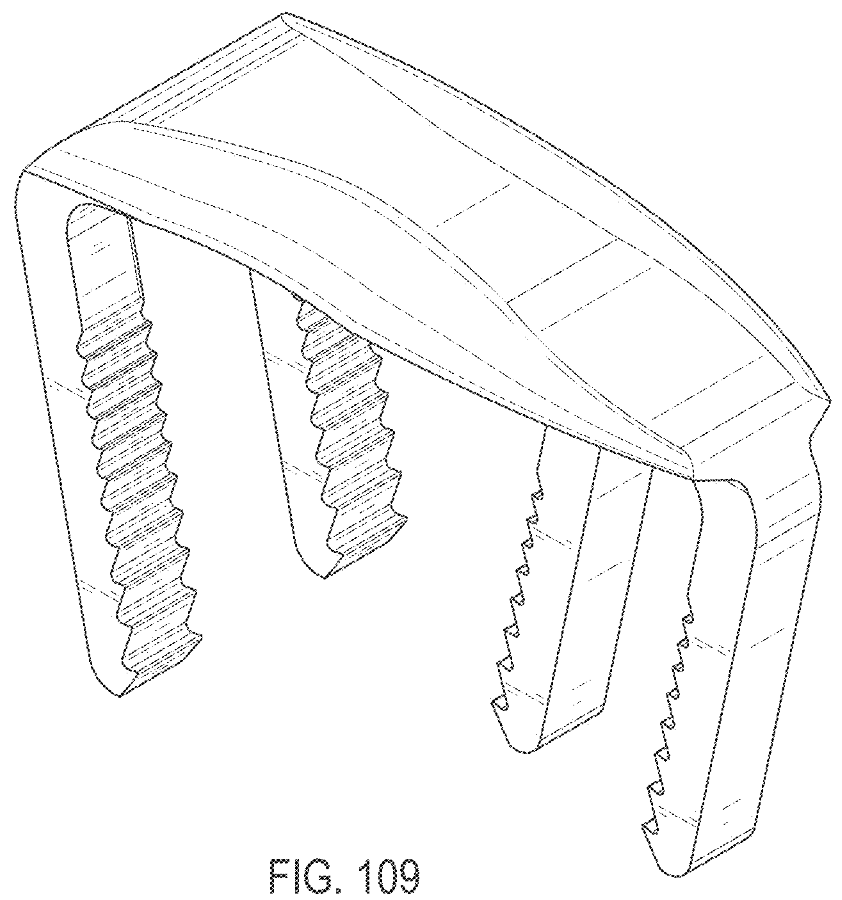
Figure 110:
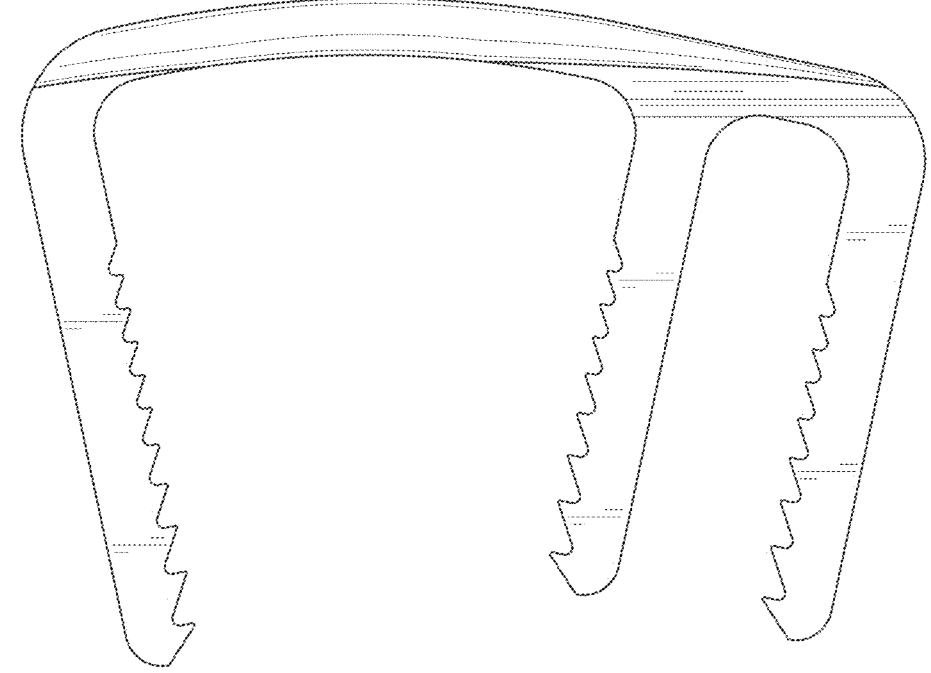
Figure 111:
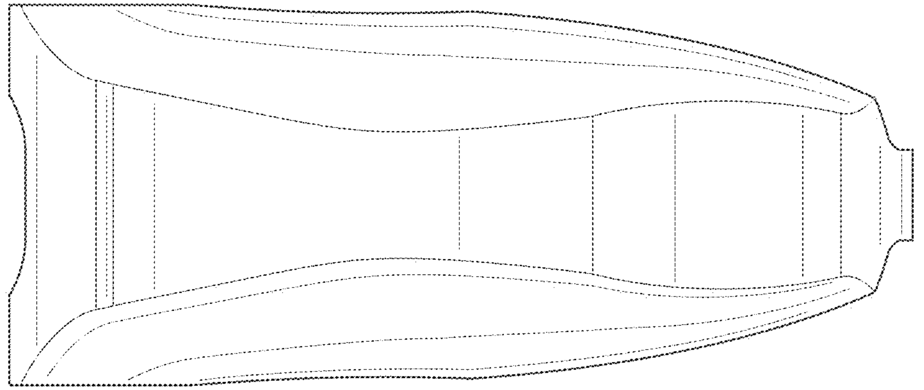
Figure 112:
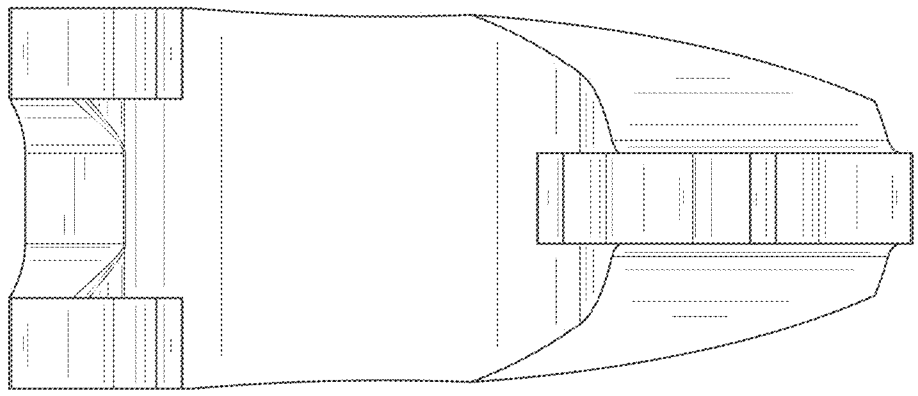
Figure 113:
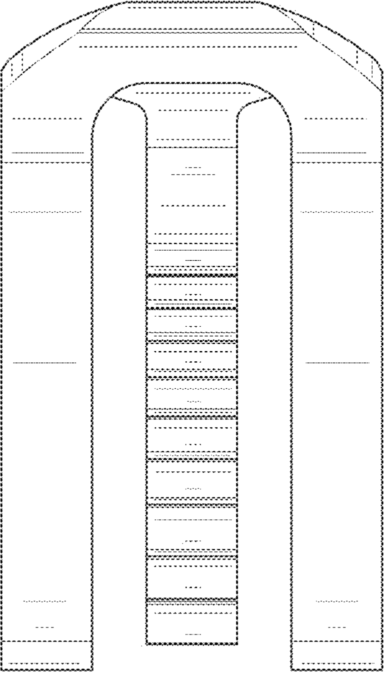
Figure 114:
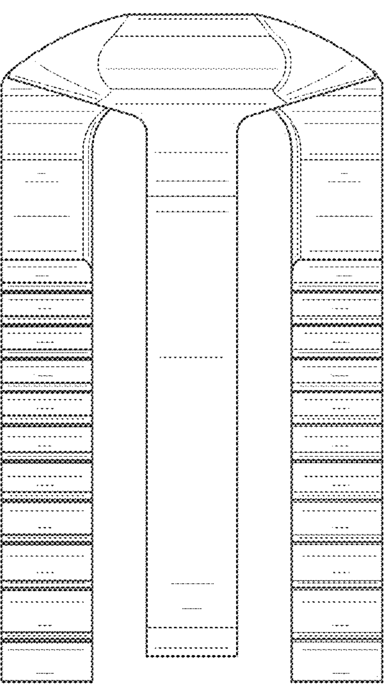
Figure 115:
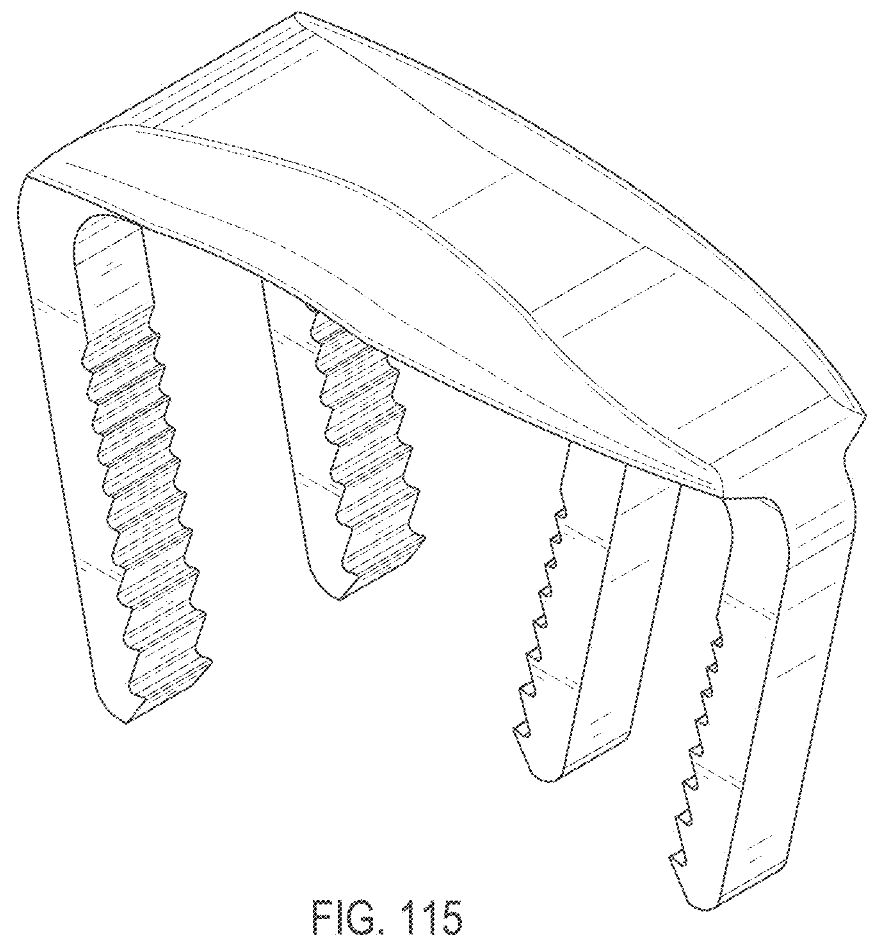
Figure 116:
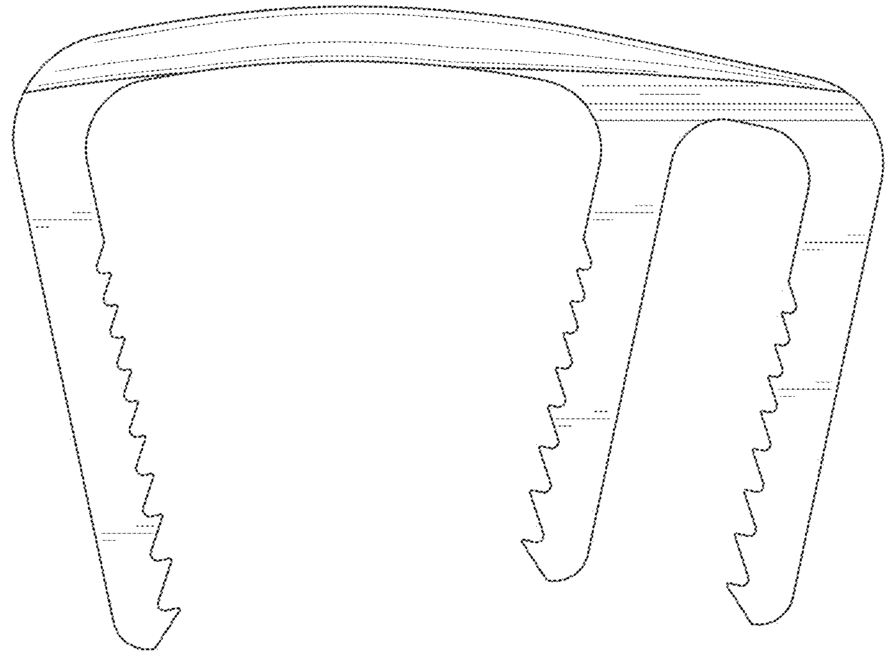
Figure 117:
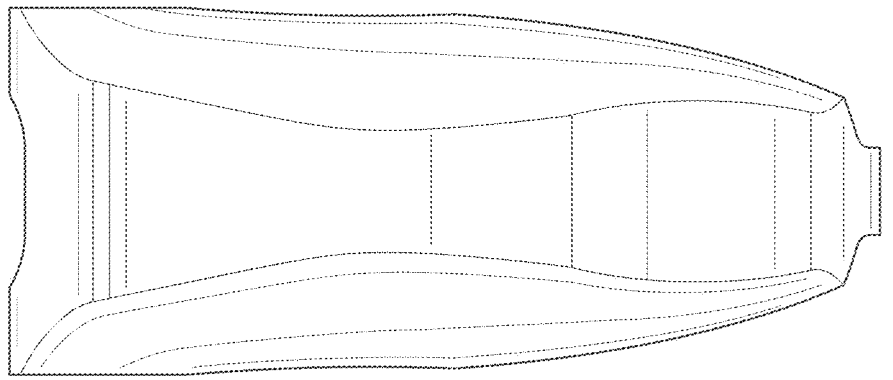
Figure 118:
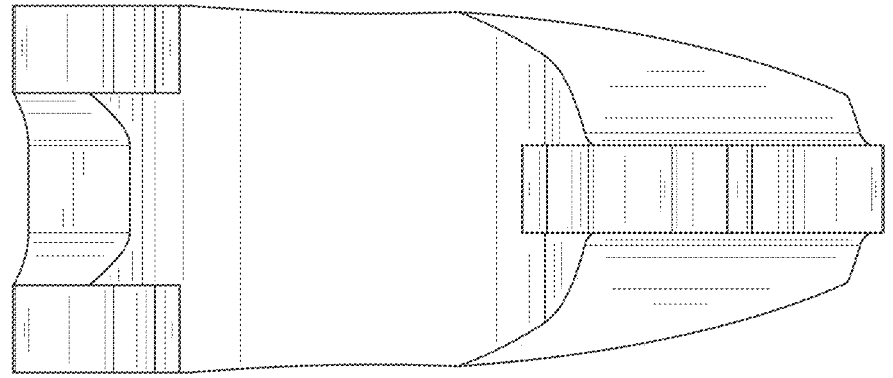
Figure 119:
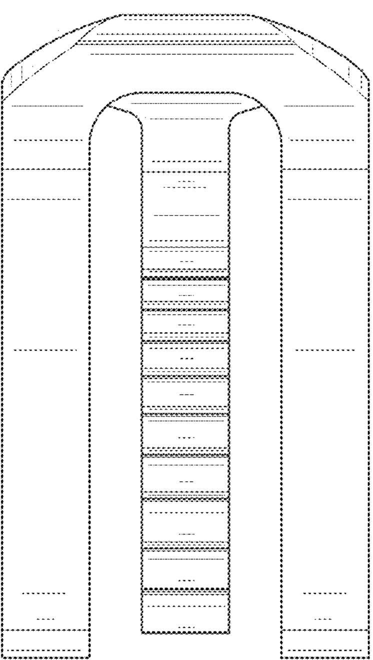
Figure 120:
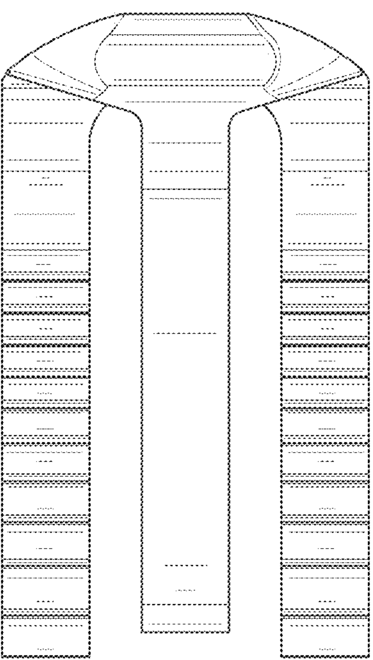

FIG. 38 shows an exemplary finite element analysis (FEA) 38000 of one embodiment of the staple 27000. In various embodiments, the FEA 38000 demonstrates the concentration of stress to and distribution of stress throughout the bridge 27001. According to one embodiment, the substantially non-breaking construction and radial transitions of a bottom surface 27011 contributes to the concentration of stress to and distribution of stress throughout the bridge 27001. In one or more embodiments, the bottom surface 27011 demonstrates a strain 37001 of less than about 0.0048 mm/mm, about 0.004 mm/mm, or at least about 0.0032 mm/mm.

Aspects, features, and benefits of the claimed systems and methods will become apparent from the information disclosed in the exhibits and the other applications as incorporated by reference. Variations and modifications to the disclosed systems and methods may be effected without departing from the spirit and scope of the novel concepts of the disclosure.

It will, nevertheless, be understood that no limitation of the scope of the disclosure is intended by the information disclosed in the exhibits or the applications incorporated by reference; any alterations and further modifications of the described or illustrated embodiments, and any further applications of the principles of the disclosure as illustrated therein are contemplated as would normally occur to one skilled in the art to which the disclosure relates.

The foregoing description of the exemplary embodiments has been presented only for the purposes of illustration and description and is not intended to be exhaustive or to limit the devices and methods for using the same to the precise forms disclosed. Many modifications and variations are possible in light of the above teaching.

The embodiments were chosen and described in order to explain the principles of the devices and methods for using the same and their practical application so as to enable others skilled in the art to utilize the devices and methods for using the same and various embodiments and with various modifications as are suited to the particular use contemplated. Alternative embodiments will become apparent to those skilled in the art to which the present devices and methods for using the same pertain without departing from their spirit and scope. Accordingly, the scope of the present devices and methods for using the same is defined by the appended claims rather than the foregoing description and the exemplary embodiments described therein.

What is claimed is:

1. A staple comprising:

a bridge between radial tangents of two opposing legs, the bridge comprising:

a non-breaking top surface between a first edge and a second edge;

an apex of the top surface;

a first curved surface between the apex and the first edge;

a second curved surface between the apex and the second edge;

a first transition area transitioning the top surface of the bridge downwardly to an outer surface of each of two legs proximate a first side of the bridge, the first transition area comprising at least a portion of the top surface of the bridge and a first side surface with each of the two legs extending therefrom, such that the two legs extend from the first side surface, the first transition area being a first non-breaking surface connecting the top surface of the bridge and each of the two legs proximate the first side of the bridge;

a second transition area transitioning the top surface of the bridge downwardly to an outer surface of at least one leg proximate a second side of the bridge, the second transition area comprising at least a portion of the top surface of the bridge and a second side surface with the at least one leg extending therefrom, such that the at least one leg extends from the second side surface, the second transition area being a second non-breaking surface connecting the top surface of the bridge and the at least one leg proximate the second side of the bridge, wherein:

the staple is deformable from a relaxed position to a deformed position; and strain in the bridge is greater than or equal to strain in the two legs or the at least one leg, thereby reducing a risk of breakage of the staple.

2. The staple of claim 1, wherein strain in a central region of the bridge is greater than strain in other portions of the bridge.

3. The staple of claim 2, wherein strain at the apex of the bridge is greater than strain in the first transition area or the second transition area.

4. The staple of claim 3, wherein each of the first side surface and the second side surface are curved, defining a radial transition between each of the two legs and the at least one leg and the bridge.

5. The staple of claim 4, wherein the bridge comprises:

a midpoint;

a first thickness at the midpoint;

a second thickness at the radial transition to the at least one leg.

6. The staple of claim 5, wherein the second thickness is greater than the first thickness.

7. The staple of claim 6, wherein a thickness of the bridge decreases linearly from the second thickness to the first thickness.

8. The staple of claim 4, wherein the two legs, at least one leg, and bridge are integrally formed and manufactured from a single piece of metal.

9. The staple of claim 8, wherein the staple comprises nitinol.

10. The staple of claim 9, wherein the first curved surface and the second curved surface form a constantly curved surface between the first edge and the second edge.

11. The staple of claim 9, wherein the apex comprises a flat portion between the first curved surface and the second curved surface.

12. A method comprising:

inserting a staple into one or more bone fragments of a patient in a deformed position, the staple comprising:

a bridge between radial tangents of two opposing legs, the bridge comprising:

a non-breaking top surface between a first edge and a second edge;

an apex of the top surface;

a first curved surface between the apex and the first edge;

a second curved surface between the apex and the second edge;

a first transition area transitioning the top surface of the bridge downwardly to an outer surface of each of two legs proximate a first side of the bridge, the first transition area comprising at least a portion of the top surface of the bridge and a first side surface with each of the two legs extending therefrom, such that the two legs extend from the first side surface, the first transition area being a first non-breaking surface connecting the top surface of the bridge and each of the two legs proximate the first side of the bridge;

a second transition area transitioning the top surface of the bridge downwardly to an outer surface of at least one leg proximate a second side of the bridge, the second transition area comprising at least a portion of the top surface of the bridge and a second side surface with the at least one leg extending therefrom, such that the at least one leg extends from the second side surface, the second transition area being a second non-breaking surface connecting the top surface of the bridge and the at least one leg proximate the second side of the bridge, and:

causing the staple to attempt to move from the deformed position to a relaxed position such that the staple compresses the one or more bone fragments of the patient and strain in the bridge is greater than or equal to strain in the two legs or the at least one leg, thereby reducing a risk of breakage of the staple.

13. The method of claim 12, wherein strain in a central region of the bridge is greater than strain in other portions of the bridge.

14. The method of claim 13, wherein strain at the apex of the bridge is greater than strain in the first transition area or second transition area.

15. The method of claim 14, wherein each of the first side surface and the second side surface are curved, defining a radial transition between each of the two legs and the at least one leg and the bridge.

16. The method of claim 15, wherein the bridge comprises:

a midpoint;

a first thickness at the midpoint;

a second thickness at the radial transition to the at least one leg.

17. The method of claim 16, wherein the second thickness is greater than the first thickness.

18. The method of claim 17, wherein a thickness of the bridge decreases linearly from the second thickness to the first thickness.

19. The method of claim 15, wherein the first curved surface and the second curved surface form a constantly curved surface between the first edge and the second edge.

20. The method of claim 15, wherein the apex comprises a flat portion between the first curved surface and the second curved surface.

* * * * *